US010640747B2

(12) United States Patent
Roach et al.

(10) Patent No.: US 10,640,747 B2
(45) **Date of Patent: *May 5, 2020**

(54) BIOMATRIX SCAFFOLDS FOR INDUSTRIAL SCALE DISPERSAL

(71) Applicant: The University of North Carolina at Chapel Hill, Chapel Hill, NC (US)

(72) Inventors: Marsha Lynn Roach, Branford, CT (US); Richard Harold Malavarca, Long Valley, NJ (US); Yunfang Wang, Beijing (CN); Lola M. Reid, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 15 days.

This patent is subject to a terminal disclaimer.

(21) Appl. No.: 15/952,094

(22) Filed: Apr. 12, 2018

(65) Prior Publication Data

US 2019/0024043 A1 Jan. 24, 2019

Related U.S. Application Data

(62) Division of application No. 14/813,993, filed on Oct. 13, 2015, now Pat. No. 9,944,896, which is a division of application No. 13/807,260, filed as application No. PCT/US2011/042825 on Jul. 1, 2011, now Pat. No. 9,102,913.

(60) Provisional application No. 61/360,939, filed on Jul. 2, 2010.

(51) Int. Cl.

| | |
|---|---|
| *C12N 5/07* | (2010.01) |
| *A61L 27/24* | (2006.01) |
| *A61L 27/36* | (2006.01) |
| *C12N 5/00* | (2006.01) |
| *C12N 5/071* | (2010.01) |
| *C12N 5/09* | (2010.01) |
| *C12N 7/00* | (2006.01) |

(52) U.S. Cl.

CPC ............ *C12N 5/0068* (2013.01); *A61L 27/24* (2013.01); *A61L 27/3604* (2013.01); *A61L 27/3683* (2013.01); *A61L 27/3691* (2013.01); *C12N 5/067* (2013.01); *C12N 5/0671* (2013.01); *C12N 5/0693* (2013.01); *C12N 7/00* (2013.01); *A61L 2430/28* (2013.01); *C12N 2500/25* (2013.01); *C12N 2500/36* (2013.01); *C12N 2501/20* (2013.01); *C12N 2501/998* (2013.01); *C12N 2506/14* (2013.01); *C12N 2533/54* (2013.01); *C12N 2533/90* (2013.01)

(58) Field of Classification Search

None

See application file for complete search history.

(56) References Cited

U.S. PATENT DOCUMENTS

| | | | |
|---|---|---|---|
| 5,866,414 | A | 2/1999 | Badylak et al. |
| 6,149,891 | A | 11/2000 | Korenstein et al. |
| 6,296,810 | B1 | 10/2001 | Ulmer |
| 2002/0115208 | A1 | 8/2002 | Mitchell et al. |
| 2002/0177551 | A1 | 11/2002 | Terman |
| 2003/0014126 | A1 | 1/2003 | Patel et al. |
| 2004/0187877 | A1 | 9/2004 | Badylak et al. |
| 2005/0058631 | A1 | 3/2005 | Kihm et al. |
| 2007/0020225 | A1 | 1/2007 | Abramson et al. |
| 2007/0154552 | A1 | 7/2007 | Siegal et al. |
| 2007/0190649 | A1 | 8/2007 | Gage |
| 2007/0269886 | A1 | 11/2007 | Qian et al. |
| 2008/0131966 | A1 | 6/2008 | Hariri |
| 2009/0012627 | A1 | 1/2009 | Claesson et al. |
| 2009/0060961 | A1 | 3/2009 | Naruse et al. |
| 2009/0118166 | A1 | 5/2009 | Badylak |
| 2010/0222882 | A1 | 9/2010 | Badylak |
| 2012/0064050 | A1 | 3/2012 | Calle et al. |
| 2012/0064537 | A1 | 3/2012 | Ross |

FOREIGN PATENT DOCUMENTS

| | | | |
|---|---|---|---|
| CN | 1777437 | A | 5/2006 |
| CN | 101182464 | A | 5/2008 |
| CN | 101237898 | A | 8/2008 |
| CN | 101238249 | A | 8/2008 |
| WO | WO-2010/039823 | A2 | 4/2010 |

OTHER PUBLICATIONS

Burgeson, et al. "Fetal Membrane Collagens: Identification of Two New Collagen Alpha Chains", Proc Natl Acad. Sci., Aug. 1976, vol. 73, No. 8, pp. 2579-2583.

Communication pursuant to Article 94(3) EPC EP Appln No. 11 801 493.5 dated Oct. 22, 2014.

Communication pursuant to Article 94(3) EPC EP Appln No. 11 801 504.9 dated Jun. 11, 2014.

First Office Action in CN Appln No. 201180042689.9 dated Apr. 30, 2014.

International Preliminary Report on Patentability and Written Opinion in PCT/US2011/042805 dated Jan. 17, 2013.

International Search Report in USSN PCT/US11/042805 dated Jan. 27, 2012.

Invitation pursuant to Article 94(3) and Rule 71(1)EPC in EP Appln No. 11 801 493.5 dated May 30, 2014.

Lin, et al. "Assessing Porcine Liver-Derived Biomatrix for Hepatic Tissue Engineering", Tissue Engineering, 2004, vol. 10, No. 7/8, pp. 1046-1053.

Linke, et al. "Engineered Liver-Like Tissue on a Capillarized Matrix for Applied Research", Tissue Engineering, Nov. 11, 2007, vol. 13, pp. 2699-2707.

Mather, et al. "Introduction to Cell and Tissue Culture: Theory and Technique", Plenum Press: New York, pp. 25-49.

(Continued)

*Primary Examiner* — Michelle F. Paguio Frising

(74) *Attorney, Agent, or Firm* — Gilberto M. Villacorta; Oyvind Dahle; Foley & Lardner LLP

(57) ABSTRACT

The present invention provides biomatrix scaffolds for industrial scale dispersal.

16 Claims, 26 Drawing Sheets

Specification includes a Sequence Listing.

(56) References Cited

OTHER PUBLICATIONS

Miller, et al. "Preparation and Characterization of the Different Types of Collagen", Methods in Enzymology, 1982, vol. 82, pp. 33-64.
Office Action dated Jan. 26, 2015 in China Application No. 201180042690.1, with translation.
Ross, et al. "Embryonic Stem Cells Proliferate and Differentiate When Seeded into Kidney Scaffolds", J Am Soc Nephrol, 2009, vol. 20, pp. 2338-2347.
Search Report dated Oct. 16, 2013 in European Application No. 11801493.5.
Shupe, et al. "Method for the decellularization of intact rat liver", Organogenesis, Apr. 1, 2010, vol. 6, No. 2, pp. 134-136.
Sigma-Aldrich, http://www.sigmaaldrich.com/life-science/metabolomics/enzyme-explorer/analytical-enzymes/trypsin/trypsin-inhibitors.html; Internet Archive Wayback Machine, captured on Jan. 12, 2010; accessed on Nov. 4, 2013.
Wang, et al. "Lineage Restriction of Human Hepatic Stem Cells to Mature Fates is Made Efficient by Tissue-Specific Biomatrix Scaffolds", Hepatology, (online publication Dec. 23, 2010), vol. 53, pp. 293-305.
Wu, et al. "The use of phospholipase A2 to prepare acellular porcine corneal stroma as a tissue engineering scaffold", Biomaterials, vol. 30, pp. 3513-3522 (2009).
Chinese Office Action in CN Appln No. 201180042689.9 dated Jul. 24, 2015.
Invitation Pursuant to Article 94(3) and Rule 71(1) EPC in EP Appln No. 11801493.5 dated May 5, 2015.
Invitation Pursuant to Article 94(3) and Rule 71(1) EPC in EP Appln No. 11801504.9 dated May 5, 2015.
Office Action dated Aug. 5, 2015 in Japanese Application No. 2013-518758.
Office Action dated Aug. 5, 2015 in Japanese Application No. 2013-518763.
Office Action dated Feb. 12, 2015 in China Application No. 201180042689.9, with translation.
Restriction Requirement in U.S. Appl. No. 13/807,260 dated Feb. 5, 2014.
U.S. Notice of Allowance dated Apr. 7, 2015 in U.S. Appl. No. 13/807,260.
U.S. Notice of Allowance on 069961-2302 dated Apr. 4, 2014.
U.S. Office Action U.S. Appl. No. 13/807,253 dated Nov. 6, 2013.
U.S. Office Action on U.S. Appl. No. 13/807,253 dated Sep. 10, 2013.
U.S. Office Action on U.S. Appl. No. 13/807,260 dated Jun. 4, 2014.
Office Action issued in corresponding Chinese application No. 201180042689.9 dated Dec. 21, 2015 with English translation.
Office Action issued in related U.S. Appl. No. 14/455,819, dated Apr. 27, 2016.
Lonza: "Phosphate Buffered Saline," TechSheet: Lonza Walkersville, Inc.: Walkersville, MD (2009).
Dong, "The study of a new detergent (octyl-glucopyranoside) for decellularizing porcine pericardium as tissue engineering scaffold," *J. Surg. Res.*, vol. 183, No. 1, pp. 56-67 (2013) [Abstract].
Wang, Method for perfusion decellularization of porcine whole liver and kidney for use as a scaffold for clinicial-scale bioengineering enfrafts, *Xenotransplantation*, vol. 22, pp. 48-61 (2015).
Xu, "Comparison of Decellularization Protocols for Preparing a Decellularized Porcine Annulus Fibrosus Scaffold," *Protocols for Decellularized Annulus Fibrosus*, e86723, pp. 1-13 (2014).
Chinese Official Action issued in related Chinese Patent Application No. 201180042689.9, dated Sep. 7, 2016.
Uygun, et al., "Organ reengineering through development of a transplantable recellularized liver graft using decellularized liver matrix," Nat Med., vol. 16, No. 7, pp. 814-820 (2010).
Japanese Office Action issued in related Japanese Patent Application No. 2013-518758, dated Jan. 18, 2017 (with English Translation).
Lodish et al., Molecular Cell Biology $4^{th}$ Ed., Section 22.4, W.H. Freeman: New York, (2000).
Murphy et al., "Effects of Extracellular Matrix Components and Dihydrotestosterone on the Structure and Function of Human prostate Cancer Cells," The Prostate, vol. 20, pp. 29-41 (1992).
Non-Final Office Action issued in co-pending U.S. Appl. No. 15/221,413, dated Apr. 5, 2018.

FIGURE 4D

| | Matrix Component | | Liver (in vivo) | Biomatrix Scaffolds |
|---|---|---|---|---|
| Collagens | Fibrillar | Type I | Glisson's capsule, portal triads and points of hepatic cords | Portal triads and mid-acinar region |
| | | Type III | Portal triads, ductal Plates, Canals of Hering, reticulin framework of the sinusoids | Throughout scaffold, especially around portal triads and remnants of muralia of parenchymal cells |
| | | Type V | Around portal triads and points of hepatic cords | Portal triads and mid-acinar region |
| | Basement membrane | Type IV | Around portal triads and central vein, between parenchyma and endothelia in Space of Disse | Portal triads and around vasculature |
| | | Type VI | Portal triads and around vasculature | Portal triads and around remnants of vasculature |
| Adhesion proteins | Basement membrane | Laminin | Portal triads | Portal triads |
| | | Nidogen | Around vasculature | Portal triads and around remnants of vasculature |
| | others | Fibronectin | Throughout liver plates as thin filaments | Throughout matrix scaffolds; especially around remnants of muralia of parenchymal cells |
| | | Elastin | Particularly evident around vasculature and Glisson's capsule | Waves of elastin near blood vessel remnants |
| | | Vimentin | Particularly evident around vasculature | Throughout matrix scaffolds, especially around remnants of vasculature |
| Proteoglycans | | Hyaluronan | Around portal triad and adjacent area | --- |
| | | CS-PG | Predominantly periportal | Predominantly Periportal |
| | | HS-PGs (glypicans, syndecans) | Distributed radial surround central vein and through out sinusoidal vasculatures. Not found around portal triads. | Throughout matrix and around vasculature |
| | | HS-PG (Perlecan) | More evident around portal triads (in spaces outside of sinusoids) | Predominantly around portal triads |
| | | HP-PG | Predominantly around central veins* | n.d. |

US 10,640,747 B2

BIOMATRIX SCAFFOLDS FOR INDUSTRIAL SCALE DISPERSAL

STATEMENT OF PRIORITY

This application is a divisional of U.S. patent application Ser. No. 14/813,993, filed Oct. 13, 2015, now U.S. Pat. No. 9,944,896, which is a divisional of U.S. patent application Ser. No. 13/807,206, filed Feb. 12, 2013, now U.S. Pat. No. 9,102,913, which is the U.S. National Stage of PCT/US2011/042825, filed Jul. 1, 2011, which claims the benefit under 35 U.S.C. § 119(e) of U.S. Provisional Patent Application No. 61/360,939, filed Jul. 2, 2010, the entire contents of which are incorporated herein by reference in their entirety.

STATEMENT OF GOVERNMENT SUPPORT

Aspects of this invention were made with government support under National Institutes of Health (NIH) Grant Nos. AA014243 and IP30-DK065933, National Institute of Diabetes and Digestive and Kidney Diseases (NIDDK) Grant No. DK34987, National Cancer Institute (NCI) Grant No. CA016086 and National Institute of Dental and Craniofacial Research No. DE019569. The United States Government has certain rights to this invention.

FIELD OF THE INVENTION

This invention concerns biomatrix scaffolds and methods of producing biomatrix scaffolds and their use in diverse applications as intact scaffolds or as scaffolds that are sectioned or pulverized and dispersed in various ways for specific experimental and clinical uses.

BACKGROUND OF THE INVENTION

The ability to use differentiated cells ex vivo or in clinical programs such as cell therapies depends on the ability to maintain the cells with an adult phenotype and fully functional or to be able to lineage restrict stem cells or progenitors ("stem/progenitors") to achieve that adult phenotype. The ongoing revolution in stem cell research has made possible the identification and isolation of stem/progenitor cell populations including those from embryonic, fetal and postnatal tissues1. The ability to identify and isolate the stem/progenitors for all adult cell types and to expand and to differentiate them greatly increases the potential for utilizing them for pharmaceutical and other industrial research programs, for academic investigations and for clinical programs such as cell based therapies, and tissue engineering2.

Current methods for maintaining differentiated cells or of lineage restricting stem cells to an adult fate ex vivo are partially successful and involve plating the cells onto or embedded into a substratum of an extracellular matrix component(s) and into a medium comprised of specific hormones, growth factors and nutrients tailored for the adult phenotype desired. For very primitive stem cells such as embryonic stem (ES) cells or induced pluripotent stem (iPS) or postnatally-derived ones that can go to multiple adult fates, such as mesenchymal stem cells (MSCs) or amniotic fluid-derived stem cells (AFSCs), the stem cells are subjected to a mix of soluble signals and/extracellular matrix components and must be treated with multiple sets of these signals over weeks of time. Typically the adult phenotype achieved is distinct with every preparation and has over or under expression of certain adult-specific genes and/or aberrant regulation of one or more of the adult tissue-specific genes.

Extracellular matrix is secreted by cells, is adjacent to them on one or more of their surfaces, and has long been understood to be the structural support for cells7. It is an extraordinarily complex scaffold composed of a variety of biologically active molecules that are highly regulated and critical for determining the morphology, growth, and differentiation of the attached cells8. Tissue-specific gene expression in cultured cells is improved by culturing the cells on matrix extracts or purified matrix components9. However, individual matrix components, alone or in combination, are unable to recapitulate a tissue's complex matrix chemistry and architecture. This is related to the fact that the matrix components are in gradients associated with natural tissue zones and with histological structures such as blood vessels. This complexity of the tissue matrix is more readily achieved by extractions that decellularize a tissue and leave behind the matrix as a residue10,11. However, current decellularization protocols result in major losses of some of the matrix components due to the use of matrix-degrading enzymes or buffers that solubilize matrix components.

The present invention provides biomatrix scaffolds and methods of making and using such biomatrix scaffolds. The methods of this invention result in the production of a tissue-specific extract enriched in a majority of the collagens of the tissue and with bound matrix components and matrix-bound hormones, growth factors and cytokines that collectively yield more reproducible and potent differentiation effects on both mature cells and in lineage restriction of stem/progenitor cell populations.

SUMMARY OF THE INVENTION

The present invention provides a method of producing a biomatrix scaffold from biological tissue for dispersal (e.g., industrial scale dispersal employing volumes as described, for example in the protocols set forth in Example 2) onto culture apparatus, comprising: a) perfusing the biological tissue or homogenizing the biological tissue with a buffer comprising a salt concentration from about 3.5M NaCl. to about 4.5M NaCl; b) perfusing the biological tissue or extracting the homogenate of step (a) with a delipidating buffer comprising lipases and/or detergents in a first medium, wherein the osmolality of said first medium is from about 250 mOsm/kg to about 350 mOsm/kg and said first medium is serum free and at neutral pH; then c) perfusing the tissue or extracting the homogenate of step (b) with a buffer at a neutral pH and comprising a salt concentration from about 2.0M NaCl. to about 5.0M NaCl, the concentration chosen to keep insoluble collagens identified in the biological tissue; then d) perfusing the tissue or extracting the homogenate of step (c) with RNase and DNase in a buffer; and then e) rinsing the tissue or homogenate of step (d) with a second medium that is at neutral pH, is serum-free and has an osomolality from about 250 mOsm/kg to about 350 mOsm/kg, thereby producing an intact or homogenized biomatrix scaffold from the biological tissue, said biomatrix scaffold comprising at least 95% of the collagens and most collagen-associated matrix components and matrix bound growth factors, hormones and cytokines of the biological tissue;

f) diluting the biomatrix scaffold in basal medium;

g) freezing the biomatrix scaffold of (f) at about −80° C.;

h) pulverizing the biomatrix scaffold of (g) by cryogenic grinding into biomatrix particles ranging in size from about 1 μm to about 100 μm;

i) thawing the biomatrix particles of (h) in suspension in basal medium; and j) dispersing the biomatrix particles of step (i) onto a culture apparatus, thereby producing a biomatrix scaffold from biological tissue for dispersal (e.g., industrial scale dispersal as described herein) onto culture apparatus.

The present invention further provides biomatrix scaffold produced by the methods of this invention.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

BRIEF DESCRIPTION OF THE DRAWINGS

FIGS. 4A-D. Pattern of ECM components from portal triad to central vein in biomatrix scaffolds. Histological comparison from portal triad (zone 1) to central vein (zone 3) of normal liver (A) and liver biomatrix scaffold (B); both are hematoxylin/eosin stained sections. (C) The model illustrating a stem cell and maturational lineage system in the liver with representative matrix components shown that form patterns associated with the liver zonation. The components are listed in order of abundance from the findings of immunohistochemistry. The known lineage stages within human livers begin periportally in zone 1 (around portal triads) and progress in maturation ending with apoptotic cells in zone 3. The known matrix chemistry identified in the liver's stem cell niche is comprised of hyaluronans, type III collagen, a form of laminin that binds to cx6134 integrin, and a weakly sulfated form of CS-PG43,44. Just outside the stem cell niche are found Type IV collagen, normally sulfated CS-PGs and HS-PGs and forms of laminin binding to cx6134 integrin. HP-PGs have been documented to be located uniquely pericentrally45,46. (D) The survey of matrix components and their location in liver versus those in biomatrix scaffolds, data summarized from immunohistochemistry findings (N/D=not tested. *Found by others to be exclusively near central veins). Most components of the cytoskeleton are lost during the washes, residues of some, but not all, cytoskeletal proteins are present. The scaffolds are devoid of detectable amounts of tubulin, desmin, and actin (phalloidin assays). However, there are trace amounts of cytokeratins scattered randomly in the scaffolds; trace amounts of a-smooth muscle actin around remnants of blood vessels at the portal triads; and low levels of vimentin throughout.

DETAILED DESCRIPTION OF THE INVENTION

Figure 1:
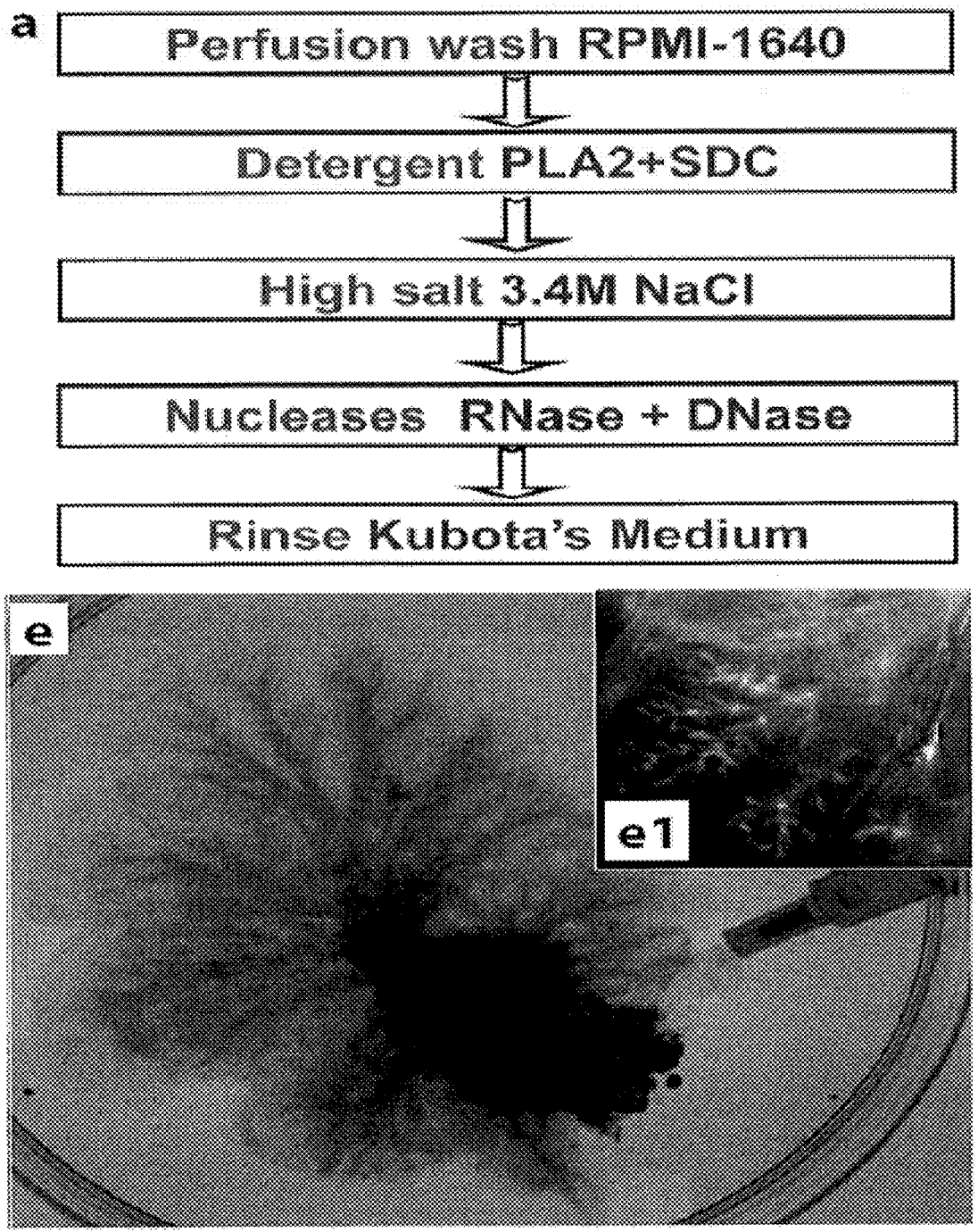
FIG. 1, Panels A-E1. Rat liver biomatrix scaffold preparation. (A) Four-step decellularization process comprised of perfusion wash, delipidation with PLA2 and SDC, high salt washes, and nuclease treatment for nucleic acid removal. (B-D) Four stages in the preparation of rat biomatrix scaffold. (B) After perfusion wash with basal medium for 10 minutes the liver becomes pale; (C) during delipidation, the liver becomes partially transparent under GC (D) final intact scaffold looks transparent at 40 minutes of perfusion; (E) biomatrix scaffold shown at low magnification. (E1) Visualization of scaffold perfused with rhodamine-labeled dextran particles demonstrates progressive flow from large vessels to the fine blood vessel branches along the channels without leakage, indicating patent vasculature in scaffolds. Corresponding hematoxylin and eosin (H&E) staining of biomatrix scaffold in different stages demonstrated that the histological structures such as blood vessels and lace-like matrix enveloping the parenchyma are preserved, whereas cells are removed. The normal rat hepatic portal triad structure consisting of the portal vein (PV), hepatic artery (HA), and bile duct (BD) (B1); the matrix fibers becoming apparent as the cells are gradually removed during the decellularization process (C1); decellularized portal triad region, compare (B1) with that in (D1), D2 and D3 show that all of the cells are removed from the matrix scaffold but mesh structures are preserved such as the blood vessels, GC, and the lace-like matrix that surrounds muralia of parenchymal cells.
Figure 1:
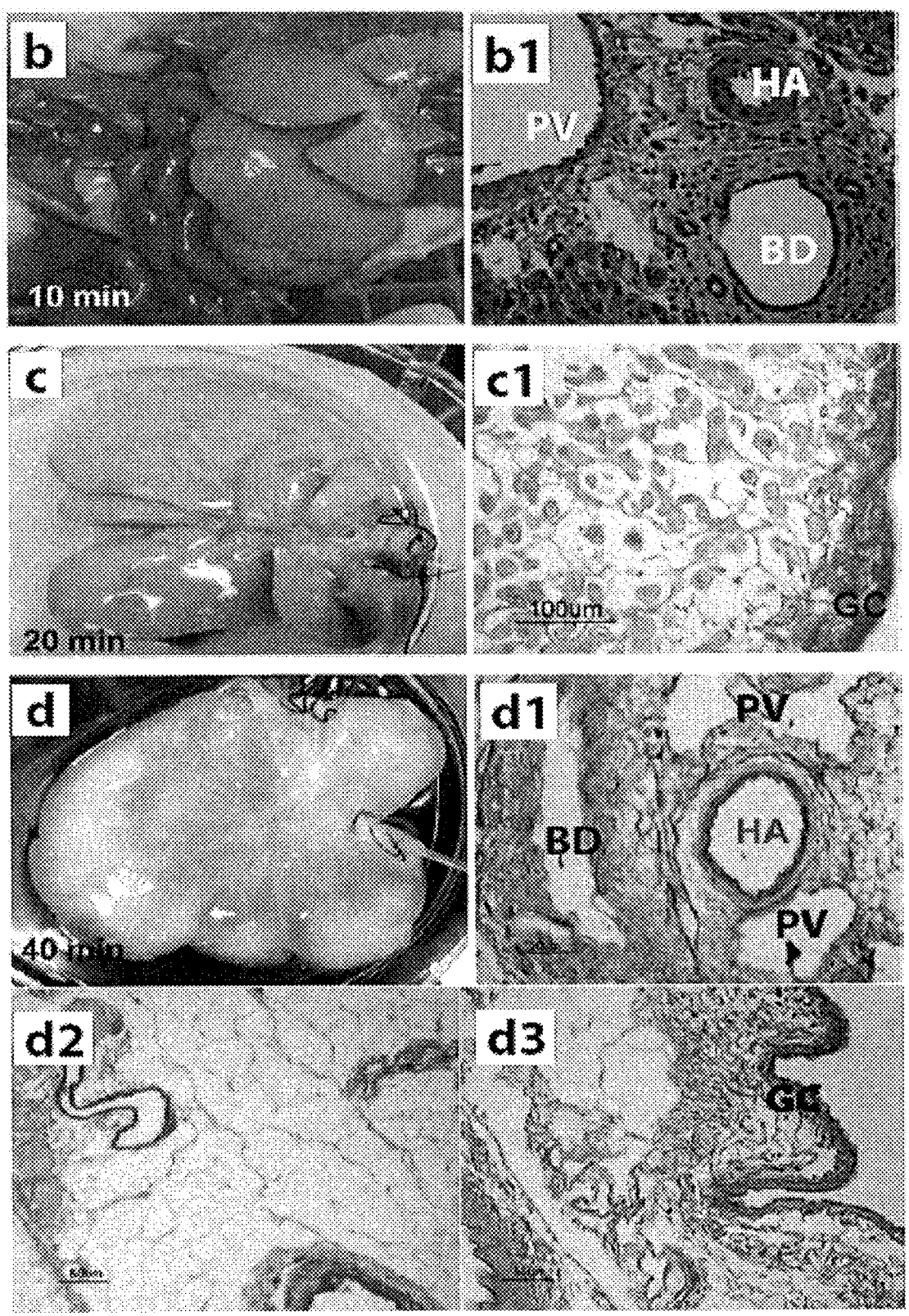

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration (e.g., the percentage of collagen in the total proteins in the biomatrix scaffold) and the like, is meant to encompass variations of 20%, 10%, 5%, 1%, 0.5%, or even 0.1% of the specified amount.

The present invention is directed to the discovery and development of a biomatrix scaffold that has unexpected improvements and advantages over decellularized tissue scaffolds now known, some examples of the improvement and advantage being the use of the biomatrix scaffold of this invention to efficiently maintain mature cells and/or to lineage restrict and/or differentiate stem cells to mature fates and/or to maintain such matured cells as functional for an extended period of time. As a further example, use of the biomatrix scaffolds of this invention reduces the time to produce cells of mature fates from about three to six weeks or more to about one to two weeks. The biomatrix scaffolds of this invention are produced using specific protocols that employ the appropriate balance of salt concentration and ionic strength (different collagens have different solubility constants (23)) for a given tissue, to allow for the retention of native collagens present in that tissue in insoluble form, resulting in a biomatrix scaffold that retains a high percent of native collagens that provide signals to drive lineage restriction and differentiation. In contrast, decellularized scaffolds produced according to known protocols do not employ such a balance of salt concentration and ionic strength to allow for retention of a high percent of these native collagens and most of these native collagens are lost when these known protocols are used. Furthermore, the biomatrix scaffolds of this invention allow for production of lineage dependent (e.g., differentiation dependent) viruses and/or pathogens in amounts sufficient for experimental and/or therapeutic use (e.g., for vaccine production).

Thus, in one embodiment, the present invention provides a method of producing a biomatrix scaffold from biological tissue, comprising the steps of: a) perfusing the biological tissue or homogenizing the biological tissue with a first medium, wherein the osmolality of said first medium is from about 250 mOsm/kg to about 350 mOsm/kg and said first medium is serum free and at neutral pH; then b) perfusing the biological tissue or extracting the homogenate of step (a) with a delipidating buffer comprising lipases and/or detergents in said first medium; then c) perfusing the tissue or extracting the homogenate of step (b) with a buffer at a neutral pH and comprising a salt concentration from about 2.0M NaCl. to about 5.0M, the concentration chosen to keep insoluble collagens identified in the biological tissue; then d) perfusing the tissue or extracting the homogenate of step (c) with RNase and DNase in a buffer; and then e) rinsing the tissue or homogenate of step (d) with a second medium that is at neutral pH, is serum-free and has an osomolality from about 250 mOsm/kg to about 350 mOsm/kg, thereby producing an intact or homogenized biomatrix scaffold from the biological tissue, said biomatrix scaffold comprising at least 95% (e.g., 80%, 85%, 90%, 95%, 98%, 99%, 100%) of the collagens and most collagen-associated matrix components and matrix bound growth factors, hormones and cytokines of the unprocessed biological tissue. Also provided herein is a biomatrix scaffold produced by any of the methods of this invention.

"Biomatrix scaffold" as used herein refers to an isolated tissue extract enriched in extracellular matrix, as described herein, which retains many or most of the collagens and collagen-bound factors found naturally in the biological tissue. In some embodiments essentially all of the collagens and collagen-bound factors are retained and in other embodiments the biomatrix scaffold comprises all of the collagens known to be in the tissue. The biomatrix scaffold may comprise at least about 50%, 60%, 70%, 75%, 80%, 85%, 90%, 95%, 97%, 98%, 99%, 99.5% or 100% of the collagens, collagen-associated matrix components, and/or matrix bound growth factors, hormones and/or cytokines, in any combination, found in the natural biological tissue. In some embodiments the biomatrix scaffold comprises at least 95% of the collagens and most of the collagen-associated matrix components and matrix bound growth factors, hormones and/or cytokines of the biological tissue. As described herein, "most of the collagen-associated matrix components and matrix bound growth factors, hormones and/or cytokines of the biological tissue" refers to the biomatrix scaffold retaining about 50%, 60%, 70%, 75%, 80%, 85%, 90%, 95%, 97%, 98%, 99%, 99.5% or 100% of the collagen-associated matrix components and matrix bound growth factors, hormones and/or cytokines found in the natural (e.g., unprocessed) biological tissue.

Exemplary collagens include all types of collagen, such as but not limited to Type I through Type XXIX collagens. The biomatrix scaffold may comprise at least about 50%, 60%, 70%, 75%, 80%, 85%, 90%, 95%, 97%, 98%, 99%, 99.5% or more of one or more of the collagens found in the natural biological tissue and/or may have one or more of the collagens present at a concentration that is at least about 50%, 60%, 70%, 75%, 80%, 85%, 90%, 95%, 97%, 98%, 99%, 99.5% or more of that found in the natural biological tissue. The amount of collagen in the biomatrix scaffold can be determined by various methods known in the art and as described herein, such as but not limited to determining the hydroxyproline content.

Exemplary collagen-associated matrix components include, but are not limited to, adhesion molecules; adhesion proteins; L- and P-selectin; heparin-binding growth-associated molecule (HB-GAM); thrombospondin type I repeat (TSR); amyloid P (AP); laminins; nidogens/entactins; fibronectins; elastins; vimentins; proteoglycans (PGs); chondroitin sulfate-PGs (CS-PGs); dermatan sulfate-PGs (DS-PGs); members of the small leucine-rich proteoglycans (SLRP) family such as biglycan and decorins; heparin-PGs (HP-PGs); heparan sulfate-PGs (HS-PGs) such as glypicans, syndecans, and perlecans; and glycosaminoglycans (GAGs) such as hyaluronans, heparan sulfates, chondroitin sulfates, keratin sulfates, and heparins. In some embodiments the biomatrix scaffold comprises, consists of, or consists essentially of collagens, fibronectins, laminins, nidogens/entactins, elastins, proteoglycans, glycosaminoglycans, growth factors, hormones, and cytokines (in any combination) bound to various matrix components. The biomatrix scaffold may comprise at least about 50%, 70%, 75%, 80%, 85%, 90%, 95%, 97%, 98%, 99%, 99.5% or more of one or more of the collagen-associated matrix components, hormones and/or cytokines found in the natural biological tissue and/or may have one or more of these components present at a concentration that is at least about 50%, 70%, 75%, 80%, 85%, 90%, 95%, 97%, 98%, 99%, 99.5% or more of that found in the natural biological tissue. In some embodiments the biomatrix scaffold comprises all or most of the collagen-associated matrix components, hormones and/or cytokines known to be in the tissue. In other embodiments the biomatrix scaffold comprises, consists essentially of or consists of one or more of the collagen-associated matrix components, hormones and/or cytokines at concentrations that are close to those found in the natural biological tissue (e.g., about 50%, 60%, 70%, 75%, 80%, 85%, 90%, 95%, 98% or 100% of the concentration found in the natural tissue).

Exemplary growth factors include, but are not limited to, fibroblast growth factors (FGFs), nerve growth factors (NGFs), epidermal growth factors (EGFs), transforming growth factors, hepatocyte growth factors (HGFs), platelet-derived growth factors (PDGFs), insulin-like growth factors (IGFs), IGF binding proteins, basic fibroblast growth factors, and vascular endothelial growth factors (VEGF). Exemplary cytokines include, but are not limited to interleukins, lymphokines, monokines, colony stimulating factors, chemokines, interferons and tumor necrosis factor (TNF). The biomatrix scaffold may comprise at least about 50%, 60%, 70%, 75%, 80%, 85%, 90%, 95%, 97%, 98%, 99%, 99.5%, 100% or more (in any combination) of one or more of the matrix bound growth factors and/or cytokines found in the natural biological tissue and/or may have one or more of these growth factors and/or cytokines (in any combination) present at a concentration that is at least about 50%, 60%, 70%, 75%, 80%, 85%, 90%, 95%, 97%, 98%, 99%, 99.5%, 100% or more of that found in the natural biological tissue. In some embodiments the biomatrix scaffold comprises physiological levels or near-physiological levels of many or most of the matrix bound growth factors, hormones and/or cytokines known to be in the natural tissue and/or detected in the tissue and in other embodiments the biomatrix scaffold comprises one or more of the matrix bound growth factors, hormones and/or cytokines at concentrations that are close to those physiological concentrations found in the natural biological tissue (e.g., differing by no more than about 30%, 25%, 20%, 25%, 20%, 15%, 10%, 5%, 4%, 3%, 2%, 1%, 0.5% in comparison). The amount or concentration of growth factors or cytokines present in the biomatrix scaffold can be determined by various methods known in the art and as described herein, such as but not limited to various antibody assays and growth factor assays.

"Biological tissue" as used herein refers to any tissue of a living or deceased organism or any tissue derived from a living or deceased organism. The term "natural biological tissue" and variations thereof as used herein refer to the biological tissue as it exists in its natural or unmodified state in the organism. The biomatrix scaffolds of the present invention can be prepared from any biological tissue. The biological tissue may include any single tissue (e.g., a collection of cells that may be interconnected) or a group of tissues making up an organ or part or region of the body of an organism. The tissue may comprise a homogeneous cellular material or it may be a composite structure such as that found in regions of the body including the thorax which for instance can include lung tissue, skeletal tissue, and/or muscle tissue.

Exemplary biological tissues of this invention include, but are not limited to liver, lung, thyroid, skin, pancreas, blood vessels, bladder, kidneys, brain, biliary tree, duodenum, abdominal aorta, iliac vein, heart and intestines, including any combination thereof. The organism (i.e., subject) from which the biological tissue is associated with or derived from may be any animal, including mammals and non-mammals such as invertebrates.

Exemplary subjects include, but are not limited to mammals, such as but not limited to, humans, mice, rats, ferrets, hamsters, rabbits, guinea pigs, pigs, porcine, dogs, cats, horses, cows, sheep, monkeys, and chimpanzees, and non-mammals, such as but not limited to birds, reptiles, and invertebrate animals. The subject may be any age and/or size. The biological tissue may be healthy, diseased, and/or have genetic mutations. In some embodiments the biomatrix scaffolds of the present invention are tissue specific in their chemistry and functionality, i.e., the biomatrix scaffolds are representative or comparable to the biological tissue from which they were created in terms of their chemistry and functionality.

In some embodiments the native histology and patent vasculatures are maintained in the biomatrix scaffolds. This may include the recognizable remnants of major histological entities of the biological tissue, such as but not limited to blood vessels and other vasculature for any tissue; bile ducts and Glisson's capsule (GC) of the liver; pancreatic ducts, islets and acini of the pancreas; bronchi, trachea, and alveoli of the lungs, etc. In other embodiments the biomatrix scaffold's chemistry is matched to the histology (e.g., matrix around blood vessels is distinct from that around hepatocytes). In some embodiments the chemistry of the biomatrix scaffold is in a gradient that is correlated with the histology. For example, when the biological tissue is the liver, the biomatrix scaffold may retain the gradient in the matrix chemistry correlating with the hepatic acinar zones 1-3 from portal triad to central vein and with histological entities such as vascular channels and Glisson's capsule (GC). Further examples include, but are not limited to, blood vessels where the chemistry of the matrix around the blood vessels is replete with high levels of network collagens (e.g., type IV and type VI), elastins, and forms of HS-PGs; around the hepatocytes in the periportal zone (zone 1), where laminins are high in concentration along with a mix of CS-PGs and HS-PGs, whereas around the pericentral zone (zone 3), are hepatocytes surrounded by a mix of HS-PGs and HP-PGs; associated with the bile ducts where there are high levels of type I collagen, fibronectins and forms of CS-PGs and DS-PGs. There are parallel gradients in matrix chemistry in every tissue.

There are a number of rinse media, such as the first and second medium, and buffers that may be utilized in the present invention. In particular, any rinse medium or buffer may be used that maintains the collagens and bound factors (e.g., matrix components, growth factors, and cytokines) in an insoluble state. When choosing a medium or buffer, the salt concentration, pH, and ionic strength should be suitable to maintain the collagens and/or most or many of the collagen-bound matrix components and other factors (e.g., by virtue of their chemical connections directly or indirectly with the collagens) in an insoluble state. Table 1 provides molar concentration ranges of sodium chloride for various types of collagen to aid one of ordinary skill in the art in providing media and buffers that ensure the collagens, collagen-associated matrix components, and matrix bound growth factors and cytokines remain insoluble. Deyl et al. ("Preparative procedures and purity assessment of collagen proteins" *Journal of Chromatography B* 790 (2003) 245-275) additionally provides information on collagen chemistry that can facilitate identification of the optimal conditions for maintaining collagens and bound factors in an insoluble state and is incorporated herein by reference in its entirety.

Table 1 demonstrates that pH is a variable working in conjunction with salt concentration to define solubility. By having high salt concentrations, the pH can be neutral. In some embodiments of the present invention, the salt concentration chosen is one that maintains all the collagens of the tissue in an insoluble state, not just one of the collagens of the tissue in an insoluble state. For example, the known collagens in fetal liver are ones that are insoluble in salt concentrations of about 4.5M NaCl. and those in adult liver tissue that are insoluble in salt concentrations of about 3.4M-3.5M NaCl.

The osmolality of any of the rinse media and/or buffers may be, for example, from about 200 mOsm/kg to about 400 mOsm/kg, from about 250 mOsm/kg to about 350 mOsm/kg, from about 275 mOsm/kg to about 325 mOsm/kg, or from about 300 mOsm/kg to about 325 mOsm/kg, including without limitation any values within these ranges not explicitly recited herein. Distilled water and dilute buffers (e.g., with osmolality <100 mOsm/kg) will result in the loss of significant amounts of collagen, collagen-associated matrix components and matrix bound growth factors and cytokdnes. Thus, in some embodiments of the methods of this invention, distilled water and dilute buffers are not included.

As one of ordinary skill in the art would recognize, osmolality is an expression of solute osmotic concentration per mass, whereas osmolarity is per volume of solvent. Thus, conversion from osmolarity to osmolality can be made by multiplying by the mass density. Osmolality can be measured using an osmometer which measures colligative properties, such as freezing-point depression, vapor pressure, and boiling-point elevation.

Osmolarity is the measure of solute concentration, defined as the number of osmoles (Osm) of solute per liter (L) of solution (osmol/L or Osm/L). The osmolarity of a solution is usually expressed as Osm/L. Whereas molarity measures the number of moles of solute per unit volume of solution, osmolarity measures the number of osmoles of solute particles per unit volume of solution. Osmolality is a measure of the osmoles of solute per kilogram of solvent (osmol/kg or Osm/kg).

Molarity and osmolarity are not commonly used in osmometry because they are temperature dependent. This is because water changes its volume with temperature. However, if the concentration of solutes is very low, osmolarity and osmolality are considered equivalent.

The osmolarity of a solution can be calculated from the following expression:

$$\text{osmol}/L = \sum_i \varphi_i n_i C_i$$

where $\varphi$ is the osmotic coefficient, which accounts for the degree of non-ideality of the solution; n is the number of particles (e.g. ions) into which a molecule dissociates; C is the molar concentration of the solute; and the index i represents the identity of a particular solute. In the simplest case $\varphi$ is the degree of dissociation of the solute. Then, $\varphi$ is between 0 and 1 where 1 indicates 100% dissociation. However, $\varphi$ can also be larger than 1 (e.g., for sucrose). For salts, electrostatic effects cause $\varphi$ to be smaller than 1 even if 100% dissociation occurs.

Perfusion of the biological tissue with any medium or buffer may be accomplished by forcing the medium or buffer through the relevant vasculature of the biological tissue. For example, if the biological tissue is the liver, then the medium or buffer may be perfused through the portal vein of the liver. Alternatively, the medium or buffer may be poured over the biological tissue and/or allowed to diffuse through the biological tissue. For example, the biological tissue may be submerged and/or dialyzed in the medium or buffer allowing the medium or buffer to diffuse through the biological tissue. While submerged and/or dialyzed in the medium or buffer the solution and biological tissue may be shaken, such as on a rocker, and/or stirred. In some embodiments the media and buffers are perfused through the relevant vasculature of the biological tissue.

Alternatively, the tissue may be homogenized in the initial medium and the buffers and media used thereafter being for extraction of the homogenate. The homogenized versions of the biomatrix scaffolds are prepared from large organs (e.g., from cow or pig tissues), are then pulverized into powder at liquid nitrogen temperatures, and the powder used on dishes for culture studies.

In some embodiments the first medium and/or the second medium is a basal medium, such as but not limited to RPMI 1640, DME/F12, DME, F12, BME, DMEM, Waymouth's, or William's medium. Other exemplary basal media are known in the art and are commercially available. The first medium and/or second medium can comprise, consist essentially of or consist of components that are combined to keep most collagens insoluble and as native molecules, as described herein (e.g., by the particular combination of osmolality and ionic strength as well as the absence of serum). The first medium and/or second medium may comprise, consist of, or consist essentially of constituents present or similar to or mimicking those present in the interstitial fluid such as but not limited to water; salts such as but not limited to inorganic salts; vitamins; minerals; amino acids such as but not limited to glycine, serine, threonine, cysteine, asparagine, and/or glutamine; sugars; fatty acids; coenzymes; hormones; and neurotransmitters. In certain embodiments where the first medium and/or second medium comprises constituents present or similar to or mimicking those present in the interstitial fluid, the constituents can yield an osmolality approximately equivalent to the osmolality of commercially available basal medium or yield an osmolality from about 250 mOsm/kg to about 350 mOsm/kg. In some embodiments the first medium and/or second medium includes media that are serum free, comprise constituents present in interstitial fluid, and/or have an osmolality from about 250 mOsm/kg to about 350 mOsm/kg. Such media can also be at neutral pH. The specific composition of the first medium and/or second medium is determined, in particular embodiments, by the insolubility constants of the collagens of the biological tissue used to make the biomatrix scaffold, as would be known to one of ordinary skill in the art.

The delipidating buffer of the present invention should be effective and yet gentle. The delipidating buffer may comprise, consist of, or consist essentially of detergents or surfactants, basal medium, salts, and/or lipases. When choosing components for the delipidating buffer, harsh detergents (e.g., sodium dodecyl sulfate; TritonX-100) should be avoided to minimize loss of matrix components. Exemplary detergents of this invention include but are not limited to anionic detergents, such as salts of deoxycholic acid, 1-heptanesulfonic acid, N-laurylsarcosine, lauryl sulfate, 1-octane sulfonic acid and taurocholic acid; cationic detergents such as benzalkonium chloride, cetylpyridinium, methylbenzethonium chloride, and decamethonium bromide; zwitterionic detergents such as alkyl betaines, alkyl amidoalkyl betaines, N-dodecyl-N, N-dimethyl-3-ammonio-1-propanesulfonate, and phosphatidylcholine; and non-ionic detergents such as n-decyl a-D-glucopyranoside, n-decyl 13-D-maltopyranoside, n-dodecyl 13-D-maltoside, n-octyl 13-D-glucopyranoside, sorbitan esters, n-tetradecyl 13-D-maltoside, tritons, Nonidet-P-40, Poloxamer 188, and any of the Tween group of detergents; sodium lauryl sulfate; and sodium deoxycholate. In some embodiments the delipidating buffer comprises sodium deoxycholate.

Exemplary lipases include, but are not limited to, phospholipases such as phospholipase A2, human pancreatic lipase, sphingomyelinases, lysosomal lipase, endothelial lipase, and hepatic lipase. In some embodiments the delipidating buffer comprises phospholipase A2. In other embodiments the delipidating buffer comprises sodium deoxycholate and phospholipase A2. This combination, in some embodiments, can comprise from about 20 to about 50 units/L phospholipase A2 and about 1% sodium deoxycholate prepared in a basal medium of neutral pH and serum-free, which can be for example, the first medium. The combination of sodium deoxycholate and phospholipase A2 rapidly degrades the phosphoglyceride located on the cytoplasm membrane and mitochondrial membrane into lysolecithin, a powerful surfactant, which can induce necrosis and cytolysis. As one of ordinary skill in the art would recognize, the amount and type of lipase and/or detergent may depend on the biological tissue.

The step of perfusing the biological tissue with the delipidating buffer is carried out, in some embodiments, until the tissue becomes transparent. In other embodiments the step of perfusing the biological tissue with the delipidating buffer is carried out until the effusion becomes clear. In some embodiments the delipidating step is carried out until the tissue becomes transparent and the effusion becomes clear.

In some embodiments prolonged exposure of the biomatrix scaffolds to enzymes from the disrupted cells is avoided since it can greatly decrease the content of elastin and the content of glycosaminoglycans such as heparan sulfates, chondroitin sulfates, dermatan sulfates and heparins, which are sites at which cytokines and growth factors bind. Exposure to the enzymes from the disrupted cells may be avoided, for instance, during delipidation and/or the subsequent washes after delipidation. In some embodiments, use of a protease inhibitor and/or careful control of the pH, temperature, and/or time can be employed to limit the activity of the proteases and/or other enzymes from disrupted cells.

Exemplary protease inhibitors include but are not limited to serine protease inhibitors such as but not limited to antipain, aprotinin, chymostatin, elastatinal, phenylmethylsulfonyl fluoride (PMSF), APMSF, TLCK, TPCK, leupeptin and soybean trypsin inhibitor; cysteine proteases such as but not limited to IAA (indoleacetic acid) and E-64; aspartic protease inhibitors such as but not limited to pepstatin and VdLPFFVdL; metalloproteases such as but not limited to EDTA, 1,10-phenanthroline and phosphoramodon; exopeptidases such as but not limited to amastatin, bestatin, diprotin A and diprotin B; thiol proteases; a-2-macroglobulin, soybean or lima bean trypsin inhibitor; pancreatic protease inhibitor; egg white ovostatin; egg white cystatin; and combinations of protease inhibitors, commonly referred to as a "protease inhibition cocktail" by commercial suppliers of such inhibitors.

The pH of the biomatrix scaffold, buffers, and/or media can be maintained at from about 6.0 to about 9.0, from about 6.5 to about 8.5, from about 7.0 to about 8.0, or from about 7.5 to about 8.0. In some embodiments, the biomatrix scaffold, buffers, and/or media are maintained at a pH of from about 7.5 to about 8.0 or are maintained at a pH of about 7.3 to about 7.5, including without limitation, any value encompassed within these ranges but not explicitly recited herein. In other embodiments the biomatrix scaffold, buffers, and/or media are maintained at neutral pH. The temperature of the biomatrix scaffold (e.g., during and/or after preparation), buffers, and/or media can be from about 0° C. to about 30° C., from about 5° C. to about 25° C., or from about 10° C. to about 20° C., including without limitation, any value encompassed within these ranges but not explicitly recited herein. In some embodiments the temperature is maintained at about 20° C. The time for perfusing the biological tissue with any medium or buffer can be from about 5 hours or less, about 3 hours or less, about 1 hour or less, about 30 minutes or less, or about 15 minutes or less. In some embodiments the step of perfusing the biological tissue with the delipidating buffer is about 30 minutes or less. In some embodiments where acidic pHs are used, the salt concentrations for maintaining the collagens and collagen-associated components insoluble can be different; the concentrations can be determined by the extant literature on collagen chemistry by choosing salt concentrations that maintain insolubility of the collagens.

Exemplary buffers include but are not limited to sodium chloride, sodium lactate, sodium acetate, sodium phosphate, sodium citrate, sodium borate, sodium gluconate, citrate buffers, bis\tris buffers, phosphate buffers, potassium phosphate, citrate/dextrose, sodium bicarbonate, ammonium chloride, 3-{[tris(hydroxymethyl)methyl]amino}propanesulfonic acid, tris(hydroxymethyl)methylamine, N-tris(hydroxymethyl)methylglycine, 4-2-hydroxyethyl-1-piperazineethanesulfonic acid, and 3-(N-morpholino)propanesulfonic acid.

In some embodiments the buffer of this invention (e.g., the buffer used in step (c) described herein) can comprise a salt in a concentration from about 2.0M or more. For example, in some embodiments the salt may be in a concentration from about 2.0M to about 5.0M, from about 2.5M to about 5.0M, from about 3.0M to about 4.5M, or from about 3.0M to about 4.0M, including without limitation, any value encompassed within these ranges but not explicitly recited herein. For instance, in some embodiments the buffer utilized in the methods of the present invention can comprise a salt such as sodium chloride in a concentration from about 2.0M NaCl to about 4.5M NaCl. In other embodiments, such as those for adult livers, the buffer utilized can comprise from about 3.4M to about 3.5M NaCl. In embodiments such as those for fetal liver, the buffer utilized can comprise a salt such as sodium chloride in a concentration from about 4.0M to about 4.50M. In some embodiments the perfusion of the biological tissue with a salt wash, such as that of step (c) of the exemplary methods described herein, is carried out until the perfusate (i.e., the fluid used for the perfusion, such as the fluid that has been forced through the vasculature) is negative for proteins by optical density (OD) at 280 nm.

Any of the media and/or buffers of the present invention may comprise a protease inhibitor. Exemplary protease inhibitors are described above. In some embodiments the buffer such as that in step (c) of the exemplary methods described herein comprises a protease inhibitor, such as soybean trypsin inhibitor. In other embodiments the buffer of step (d) comprises one or more protease inhibitors, such as soybean trypsin inhibitor.

The media and/or buffers of the present invention may comprise one or more nucleases, which in some embodiments can be prepared in the standard buffers recommended by the commercial suppliers of these enzymes. For instance, in some embodiments the buffer of step (d) comprises one or more nucleases, such as but not limited to RNase and DNase. Perfusion with nucleases eliminates residues of nucleic acids. In other embodiments the buffer of step (d) comprises RNase, DNase, and one or more protease inhibitors. In some embodiments the perfusion of the biological tissue with one or more nucleases is carried out until the perfusate (i.e., the fluid used for the perfusion, such as the fluid that has been forced through the vasculature) is negative for nucleic acids by optical density (OD) at 260 nm. In some embodiments, the nucleases eliminate 75%, 80%, 85%, 90%, 95%, 98%, or 100% of nucleic acids in the biological tissue.

The second medium (e.g., final rinse medium) can be any medium that ensures that the collagens and bound factors (e.g., matrix components, growth factors, and cytokines) will remain insoluble, as described above. Exemplary final rinse media are described above in reference to the first medium and are serum-free, at neutral pH, and with an osmolality of 250-350 mOsm/kg. For instance, in some embodiments the second medium comprises a basal medium. In some embodiments the second medium is a serum-free basal medium. In other embodiments, the second medium is a serum-free, hormonally defined medium (HDM) comprising hormones, growth factors, lipids, and serum albumin and is tailored to the need of the cells to be cultured. An exemplary second medium is Kubota's medium (Kubota and Reid, PNAS 97:12132-12137, 2000), which is designed for hepatic stem cells, hepatoblasts and other progenitors. In certain embodiments the second medium may or may not comprise supplementation with serum or a factor derived from serum, such as but not limited to human serum albumin. In some embodiments, rinsing the tissue with the second medium eliminates residues of the delipidating buffer and the nucleases. In other embodiments the wash with the second medium and/or any subsequent buffer or medium equilibrates the biomatrix scaffold with the medium or buffer. In some embodiments the first medium and second medium can be the same and in some embodiments, the first medium and second medium can be different thereby producing a biomatrix scaffold from the biological tissue.

In some embodiments one or more of the media and/or buffers utilized in the preparation of the biomatrix scaffold are free of (i.e., do not contain a detectable amount of) one or more enzymes that degrade extracellular matrix components. In other embodiments all of the media and buffers utilized in the preparation of the biomatrix scaffold are free of (i.e., do not contain a detectable amount of) one or more enzymes that degrade extracellular matrix components. Exemplary enzymes include, but are not limited to collagenases; proteases; glycosidases such as heparinase, heparitinase, chondroitinase, and hyaluronidase; and elastases.

Sterilization of the biological tissue, homogenate and/or biomatrix scaffold of this invention can be accomplished by any method known in the art, with the caveat that methods using a factor that can bind to the biomatrix scaffold (e.g., ethylene oxide) should be avoided. Exemplary methods of sterilization include but are not limited to gamma irradiation, radio frequency glow discharges (RFGD) plasma sterilization, electron beam sterilization, and super critical carbon dioxide sterilization. In some embodiments sterilization of the tissue, homogenate and/or biomatrix scaffold is accomplished with gamma irradiation at about 5,000 rads. If the scaffolds are to be used immediately for recellularization, and if sterile procedures were used in the decellularization process (especially after the high salt extraction), then sterilization may not be required.

Storage of the biomatrix scaffold can be accomplished by any method known in the art. In some embodiments (e.g., when the scaffold is to be used intact), the biomatrix scaffold can be stored at about 4° C. and in other embodiments (e.g., when the scaffold is to be dispersed into sect the biomatrix scaffold is frozen, for example, at about −80° C.

In some embodiments the biomatrix scaffold comprises, consists of, or consists essentially of collagens, fibronectins, laminins, nidogen/entactin, elastin, proteogylcans, glycosaminoglycans and any combination thereof, all being part of the biomatrix scaffold (e.g., bound to the biomatrix scaffold). In some embodiments, the biomatrix scaffold lacks a detectable amount of a collagen, fibronectin, laminin, nidogen/entactin, elastin, proteogylcan, glycosaminoglycan and any combination thereof.

The biomatrix scaffolds of the present invention have proven to be potent differentiation substrata for cells and may be used for many cell types, such as but not limited to any mature cell or for various stem cell populations. These include, e.g., embryonic stem (ES) cells, induced pluripotent stem (iPS) cells, germ layer stem cells (e.g., definitive endodermal stem cells), determined stem cells (e.g., hepatic, lung, pancreatic or intestinal stem cells), human hepatic stem cells (hHpSCs), perinatal stem cells (e.g., amniotic fluid-derived stem cells (AFSCs)), mesenchymal stem cells (MSCs) such as from bone marrow or from adipose tissue, committed progenitors, adult cells of any tissue type, diseased cells, tumor cells, mature cells, parenchymal cells, stellate cells, cholangiocytes, biliary tree cells such as those that are not cholangiocytes, hepatocytes, kidney cells, urothelial cells, mesenchymal cells, smooth or skeletal muscle cells, myocytes (muscle stem cells), fibroblasts, chondrocytes, adipocytes, fibromyoblasts, endothelial cells, ectodermal cells, including ductile and skin cells, neural cells, islet cells, cells present in the intestine, osteoblasts, other cells forming bone or cartilage, and any combination thereof. These cells may be normal or diseased.

In some embodiments the biomatrix scaffolds are used for biological, pharmaceutical, genetic, molecular, and/or virological studies of cells, whether freshly isolated from tissue or from lineage-restricted stem cells. In other embodiments the biomatrix scaffolds are used for implantable, vascularized engineered organs, such as but not limited to the liver. Other exemplary uses for the biomatrix scaffolds include, but are not limited to, protein manufacturing, drug toxicity testing, drug development, antibody screening, and/or virus production for vaccine preparations of viruses. Virus production of lineage-dependent viruses (e.g., papilloma virus and hepatitis C) can be achieved by plating stem cell populations on a tissue-specific biomatrix scaffold and then culturing in a medium that works in combination with the biomatrix scaffold to fully induce differentiation of the cells. The mature virions will be produced when the cells fully mature. As long as the virus itself does not affect cell viability, the mature cells infected with the virus can be maintained for at least eight weeks offering a means of generating large amounts of virus with a stable culture system.

The biomatrix scaffolds can be used intact, such as but not limited to use for 2-D and/or 3-D cultures for cells. In some embodiments, the biomatrix scaffolds can be used in combination with specific medium for differentiation in 2-D and/or 3-D cultures for cell lines, such as but not limited to, normal or diseased cells from any maturational lineage stage from stem cells to late stage cells.

Alternatively, the biomatrix scaffolds can be frozen. These frozen sections can be prepared and used as substrata. The biomatrix scaffolds can be quickly frozen on dry ice and frozen sections prepared with a Cryostat, placed onto culture apparati (e.g., dishes, flasks, cloth, transwells, etc.), sterilized and rehydrated in medium before seeding cells. In some embodiments, the frozen biomatrix scaffold of this invention can be sectioned.

In some embodiments a cell culture is produced, comprising: a) producing a biomatrix scaffold according to the methods of this invention; b) contacting the biomatrix scaffold of step (a) with cell culture medium in a culture apparatus; and c) seeding the biomatrix scaffold of step (b) with cells, thereby producing a cell culture.

In some embodiments a cell culture is produced, comprising: a) producing a biomatrix scaffold of the present invention; b) freezing the biomatrix scaffold of step (a); c) preparing a frozen section from the biomatrix scaffold of step (b) as a cell culture substratum; d) contacting the cell culture substratum of step (c) with cell culture medium in a culture apparatus; and e) seeding the cell culture substratum of step (d) with cells, thereby producing a cell culture.

In other embodiments the biomatrix scaffolds can be ground to a powder. One method of grinding the biomatrix scaffold to a powder comprises grinding the biomatrix scaffold to a powder in a freezer mill at temperatures at or near liquid nitrogen temperatures. Other apparatus for grinding at liquid nitrogen or equivalent temperatures (e.g., freezing with dry ice) are known in the art. The powder can be brought to room temperature at which it acquires the consistency of a paint that can be coated onto culture apparati using a sterilized paint brush or equivalent apparatus. The powder or the plates can be sterilized.

Thus, in some embodiments a cell culture is produced comprising: a) producing a biomatrix scaffold of the present invention; b) grinding the biomatrix scaffold of step (a) to a powder; c) coating a culture apparatus with the powder of step (b) to produce a cell culture substratum; d) contacting the cell culture substratum of (c) with cell culture medium in the culture apparatus; and e) seeding the cell culture substratum of (d) with cells, thereby producing a cell culture. In some embodiments of this method, the grinding of the biomatrix can be carried out in a freezer mill (e.g., cryogenic grinding) at or near liquid nitrogen temperature.

In some embodiments before seeding the cells for the cell culture, a portion of the medium is added to the culture apparatus since the cells may attach within seconds. The cells, in some embodiments attach within seconds to minutes for normal adult cells and within minutes to a few hours for various types of stem cells. In some embodiments the attachment of the cells may depend on how the biomatrix scaffolds are dispersed for use in cultures. The cell medium can be any medium that is suitable for producing a cell culture. In some embodiments the cell culture medium comprises at least one constituent present in interstitial fluid, wherein the osmolality of said medium is from about 250 mOsm/kg to about 350 mOsm/kg, wherein said medium is serum free and wherein the pH is neutral. In other embodiments the cell culture medium can be a basal medium, such as but not limited to RPMI-1640, DME/F12, Ham's medium, Kubota's medium, etc.

The cell cultures produced with the biomatrix scaffolds, in some embodiments, comprise, consist essentially of or consist of, the same type of cells as the cells of the biological tissue that was used to make the biomatrix scaffold. Nonlimiting examples of the cells of this invention include embryonic stem (ES) cells, induced pluripotent stem (iPS) cells, determined stem cells, perinatal stem cells, amniotic fluid-derived stem cells (AFSCs), mesenchymal stem cells (MSCs) from any source, committed progenitors or adult cells of any tissue type, mature cells, normal cells, diseased cells, tumor cells and any combination thereof. Additional nonlimiting examples include liver cells, parenchymal cells, stellate cells, endothelial cells, hepatocytes, cholangiocytes, biliary tree cells that are not cholangiocytes and pancreatic cells.

In some embodiments, the primitive stem cells (whether ES, iPS, MSC or AFSC) will lineage-restrict the cells, at least partially, to the tissue type used to make the biomatrix scaffold. Determined stem cells of a given germ layer will lineage restrict to the tissue type used to make the biomatrix scaffold when the scaffold is prepared from a tissue derived from that germ layer and may partially differentiate to the adult fate if on a scaffold from a tissue derived from a different germ layer. Thus, the ability of adult cells to fully differentiate may be dictated by the tissue type of the biomatrix scaffold. In parallel, the fate of stem cells may be partially or fully dictated by the tissue type of the biomatrix scaffold or the fate of stems cells may be fully dictated by the tissue type of the biomatrix scaffold. In some embodiments, the cells of the cell culture are of a different type than the cells of the biological tissue used to make the biomatrix scaffold. As described in detail above, exemplary types of cells that may be used in producing a cell culture include but are not limited to embryonic stem cells, induced pluripotent stem cells, mesenchymal stem cells, amniotic fluid derived stem cells, determined stem cells, mature cells, normal cells, diseased cells, tumor cells and any combination thereof. These cells may be from any biological tissue as described herein.

In some embodiments the biomatrix scaffolds induce slow growth or growth arrest correlated with differentiation of the normal cells, whether stem cells or mature cells. The mature cells, in some embodiments, become fully differentiated within hours and remain stably differentiated for at least eight weeks thereafter. In some embodiments adult cells (i.e., fully mature cells) attach to the scaffolds within minutes and retain their full differentiation thereafter for more than eight weeks. Stem cells, in some embodiments, undergo a few divisions and then go into growth arrest and fully differentiate. The stem cells remain stably in growth arrest, viable and fully differentiated for at least eight weeks. In some embodiments, stem cells seeded onto biomatrix scaffolds go into growth arrest or slowed growth, lose stem cell markers and differentiate to mature, functional cells in approximately one week, retaining stable phenotypes and viabilities for at least eight weeks or more (e.g., 40%, 50%, 60%, 70%, 80%, 90%, 95%, or 100% viability for an extended period of time (e.g., at least one week, at least two weeks, at least three weeks, at least four weeks, at least five weeks, at least six weeks, at least seven weeks, at least eight weeks, at least nine weeks, at least ten weeks, at least 11 weeks, at least 12 weeks, at least 13 weeks, at least 14 weeks, at least 15 weeks, at least 16 weeks, at least one month, at least two months, at least three months, at least four months, at least five months, at least six months, at least seven months, at least eight months, at least nine months, at least ten months, at least 11 months, at least one year, etc.)

In other embodiments the biomatrix scaffold is used to differentiate embryonic stem (ES) cells and/or induce pluripotent stem (IPS) cells to a specific fate. For instance, in some embodiments a tissue-specific biomatrix scaffold is used to facilitate differentiating embryonic stem cells or induced pluripotent cells towards a specific fate.

In certain embodiments of the present invention the biomatrix scaffold is used to differentiate amniotic fluid-derived stem cells (AFSCs) or mesenchymal stem cells (MSCs) from bone marrow or from adipose tissue or from any fetal or postnatal tissue or any determined stem cells (e.g., lung, intestine, biliary tree, kidney, skin, heart, etc.) towards a specific adult fate. In some embodiments the biomatrix scaffolds of the present invention are used to enhance and accelerate differentiation of stem cells to mature cells by producing a cell culture.

In other embodiments the present invention provides a method of enhancing and/or accelerating differentiation of stem cells and/or progenitors to mature cells, comprising producing a cell culture according to the methods of this invention, wherein the cells are stem cells and the cell culture medium is formulated for mature cells, thereby enhancing and/or accelerating differentiation of stem cells and/or progenitors to mature cells. The cell culture medium can be any medium that is formulated for mature cells. The constituents in the medium are distinct for each cell type. Differentiation means that the conditions cause the cells to mature to adult cell types that produce adult specific gene products. Cells employed in these methods can be adult cells of any type or stem cells or progenitors, nonlimiting examples of which include embryonic stem cells, induced pluripotent stem cells, germ layer stem cells, determined stem cells, perinatal stem cells, amniotic fluid-derived stem cells, mesenchymal stem cells, transit amplifying cells or committed progenitors of any tissue type.

Cells seeded onto the biomatrix scaffolds (e.g., intact biomatrix scaffolds, sections of scaffolds or powdered biomatrix scaffolds mixed into/onto other implantable materials) can be transplanted into animals or humans as a method of grafting cells in vivo. In some embodiments a method of delivering cells to a subject is provided comprising contacting the subject with the biomatrix scaffold of the present invention, where the biomatrix scaffold comprises cells. In other embodiments a method of delivering cells to a subject is provided that comprises seeding the biomatrix scaffold of the present invention with cells and then transplanting the biomatrix scaffold seeded with the cells into the subject. In some embodiments, a biomatrix scaffold that has not been seeded with any cells can be transplanted into a subject.

In some embodiments, the biomatrix scaffold can be used as a graft that can be used to regenerate the tissue or organ in the subject.

The biomatrix scaffolds of the present invention may be used for establishing bioartificial organs, which may be useful for analytical and/or clinical programs. The biomatrix scaffolds may also be used for identifying specific gene products or facets of disease states. In some embodiments the biomatrix scaffolds are prepared from tissues of mutant animals and subsequently used to define relevant factor(s) associated with the mutation(s). In other embodiments the biomatrix scaffolds are prepared from diseased tissues and used to define changes in the matrix relevant to the disease.

Additional nonlimiting examples of uses of the biomatrix scaffolds of this invention include: 1) use of the scaffold for culturing malignant cells to define metastatic potential (the ability of tumor cells to form growing colonies of cells on a given type of biomatrix scaffold is predictive of the ability of the cells to metastasize to the tissue from which that scaffold was prepared; 2) putting grafts of tissue on the scaffold to be used for transplantation into a subject); 3) production of organoids formed by recellularization of scaffolds to be used as assist devices, such as, for example, a liver organoid that is then connected to a subject with liver failure; 4) use of the scaffold for protein manufacturing (cells on the scaffold produce a factor that can be isolated from the medium and/or from the cells and then purified; and 5) use of the scaffold for production of lineage dependent virnses; e.g., for production of viruses that require differentiated cells to yield sufficient particles for use as a vaccine.

Thus, the present invention provides a method of identifying the metastatic potential of tumor cells in a tissue type, comprising a) producing a biomatrix scaffold according to the methods of this invention; b) contacting the biomatrix scaffold of (a) with cell culture medium in a culture apparatus; c) seeding the biomatrix scaffold of (b) with tumor cells; d) maintaining the biomatrix scaffold of (c) under culture conditions; and e) monitoring growth of the tumor cells on the biomatrix scaffold of (d), wherein growth of tumor cells on the biomatrix scaffold identifies that the tumor cells can colonize in vivo the type of tissue from which the biomatrix scaffold was produced, thereby identifying the metastatic potential of the tumor cells in the tissue type.

Also provided herein is a method of identifying a tumor cell as responsive to an anti-tumor treatment, comprising: a) producing a biomatrix scaffold according to the methods of this invention; b) contacting the biomatrix scaffold of (a) with cell culture medium in a culture apparatus; c) seeding the biomatrix scaffold of (b) with tumor cells; d) maintaining the biomatrix scaffold of (c) under culture conditions; e) applying the anti-tumor treatment to the tumor cells on the biomatrix scaffold; and f) monitoring growth of the tumor cells on the biomatrix scaffold of (e), wherein lack of growth of tumor cells and/or death of tumor cells on the biomatrix scaffold of (e) identifies the tumor cells as responsive to the anti-tumor treatment. Nonlimiting examples of anti-tumor treatment include chemotherapeutic agents, antibodies, radiation therapy, immunotherapy, hormonal therapy etc., as would be well known in the art. In some embodiments, tumor cells from a subject can be seeded unto different biomatrix scaffolds of this invention and exposed to respective anti-tumor treatments. Pursuant to the results of these respective analysis of different anti-tumor treatments, an anti-tumor treatment that is effective against the subject's tumor cells can be selected and that anti-tumor treatment can be administered to the subject to treat the subject's tumor.

In further embodiments, the present invention provides a method of producing a tumor graft for transplantation into a host animal, comprising: a) producing a biomatrix scaffold according to the methods of this invention; b) contacting the biomatrix scaffold of (a) with cell culture medium in a culture apparatus; c) seeding the biomatrix scaffold of (b) with tumor cells; d) maintaining the biomatrix scaffold of (c) under culture conditions; and e) establishing a population of the tumor cells on the biomatrix scaffold of (d), thereby producing a tumor graft for transplantation into the host animal. In some embodiments, this method can further comprise the step of transplanting the tumor graft into the host animal. In various embodiments, the tumor graft can be syngeneic, allogeneic or xenogeneic to the host animal.

Also provided herein is a method of producing virus particles of a lineage dependent virus, comprising: a) producing a biomatrix scaffold according to the methods of this invention; b) contacting the biomatrix scaffold of (a) with cell culture medium in a culture apparatus; c) seeding the biomatrix scaffold of (b) with cells of a type and lineage stage that can be infected with the lineage dependent virus; d) infecting the cells of (c) with the lineage dependent virus; e) maintaining the infected cells on the biomatrix scaffold under culture conditions; and f) collecting virus particles produced in the infected cells, thereby producing virus particles of the lineage dependent virus.

Nonlimiting examples of a lineage dependent virus of this invention include hepatitis C virus, hepatitis B virus, norovirus human papilloma virus and any other virus now known or later identified to be lineage dependent. By lineage dependent is meant that the cell in which the virus is present must mature or differentiate to a particular stage before the virus can successfully replicate in the cell and produce virus particles, as is known in the art.

Furthermore, the present invention provides a method of producing an organoid formed by recellularization of a biomatrix scaffold, comprising: a) producing a biomatrix scaffold according to the methods of this invention; b) contacting the biomatrix scaffold of (a) with cell culture medium in a culture apparatus; c) seeding the biomatrix scaffold of (b) with cells of the same tissue type as the biological tissue used to prepare the biomatrix scaffold; and d) maintaining the cells on the biomatrix scaffold under culture conditions, whereby organoids form from the cells, thereby producing an organoid formed by recellularization of the biomatrix scaffold. This method can further comprise the step of contacting the organoid produced by steps (a) through (d) with a subject, for use as an assist device, as is known in the art. Any cell type that can be used to produce the biomatrix scaffold of this invention can be used in this method. In some embodiments, the cells are liver cells.

The present invention additionally provides a method of producing a protein of interest in cells cultured on a biomatrix scaffold, comprising: a) producing a biomatrix scaffold according to the methods of this invention; b) contacting the biomatrix scaffold of (a) with cell culture medium in a culture apparatus; c) seeding the biomatrix scaffold of (b) with cells that produce the protein of interest; d) maintaining the cells of (c) on the biomatrix scaffold under culture conditions; and e) collecting the protein of interest produced by the cells of (d), thereby producing a protein of interest in cells cultured on a biomatrix scaffold. This method can comprise the further step of purifying the protein of interest collected in step (f). The protein of interest of this invention can be any protein produced by a cell, either from an endogenous gene and/or as a recombinant protein, in an amount that can be collected from the cells in culture and/or the culture medium. Numerous examples of such proteins of interest are known in the art.

The present invention is explained in greater detail in the following non-limiting examples.

EXAMPLES

Example 1. Lineage Restriction of Human Hepatic Stem Cells to Mature Fates is Made Efficient by Tissue-Specific Biomatrix Scaffolds Abstract.

Current protocols for differentiation of stem cells make use of multiple treatments of soluble signals and/or matrix factors and result typically in partial differentiation to mature cells with under- or overexpression of adult tissue-specific genes. In the present invention, a strategy was developed for rapid and efficient differentiation of stem cells using substrata of biomatrix scaffolds, tissue-specific extracts enriched in extracellular matrix, and associated growth factors and cytokines, in combination with a serum-free, hormonally defined medium (HDM) tailored for the adult cell type of interest. The studies described herein demonstrate the efficacy of the biomatrix scaffolds of this invention in differentiating human hepatic stem cells (hHpSCs) to mature fates and in maintaining mature parenchymal cells as fully functional for long periods of time. Biomatrix scaffolds were prepared by a novel four-step perfusion decellularization protocol using conditions designed to keep all collagen types insoluble. The scaffolds maintained native histology, patent vasculatures and approximately 1% of the tissue proteins but >95% of its collagens, most of the tissue's collagen-associated matrix components, and physiological levels of matrix bound growth factors and cytokines. Collagens increased from almost undetectable levels to >15% of the scaffold's proteins with the remainder including laminins, fibronectins, elastin, nidogen/entactin, proteoglycans, and matrix-bound cytokines and growth factors in patterns that correlated with histology. Human hepatic stem cells (hHpSCs), seeded onto liver biomatrix scaffolds and in an HDM tailored for adult liver cells, lost stem cell markers and differentiated to mature, functional parenchymal cells in approximately one week, remaining viable and with stable mature cell phenotypes for more than eight weeks. Thus, the biomatrix scaffolds of this invention can be used for biological and pharmaceutical studies of lineage-restricted stem cells, for maintenance of mature cells, and for implantable, vascularized engineered tissues or organs.

Procedures for Decellularization.

After anesthesia with ketamine-xylazine, the rat abdominal cavity was opened and a sleevelet with a cannula was inserted into the portal vein to perfuse the entire liver. (1) Perfusion is done with RPMI 1640 for 10 mins; followed by (2) delipidation with a lipase (e.g., 20-50 units of phospholipase A2-PLA2) combined with a gentle detergent such as 1% sodium deoxycholate (SDC) for about 30-60 mins until the tissue becomes transparent and the effusion becomes clear; (3) perfusion with high salt washes (for fetal livers: 4.5M NaCl. and for adult livers 3.4M-3.5M NaCl) is done until the perfusate is negative for proteins by optical density (OD) at 280 nm; (4) perfusion with nucleases (DNase, RNase) in RPMI 1640 until the perfusate is negative for nucleic acids by OD 260; and (5) final rinse with RPMI 1640 for 2 hours or more.

The biomatrix scaffolds are quickly frozen on dry ice and frozen sections prepared with a Cryostat, placed onto 24-well cell culture plates, sterilized by gamma irradiation (5000 rads) and rehydrated in medium (KM) for 30 min before seeding cells. The sections of biomatrix scaffolds covered 95% of well surface in the 24-well plate.

An alternative method for distributing the biomatrix scaffolds onto culture dishes consisted of pulverizing it to a powder using a freezer mill filled with liquid nitrogen. The pulverized powder, when brought to room temperature, acquires the consistency of paint, and can be coated onto any surface, such as dishes, slides, cloth, filters or other surfaces used for attaching cells and/or cell culture. Pulverizing the scaffolds eliminates the gradients of matrix components and signals, but the mix of components present still elicits potent differentiation effects. The scaffolds also can be used intact and reseeded with cells in preparation of engineered organs for transplantation in vivo or for 3-D cultures.

Alternate methods were developed for use with porcine and bovine livers. Pig and bovine livers were obtained from a USDA certified meat processing facility (CT). See Example 3 for an outline of a representative protocol. Each liver was USDA inspected and received the USDA stamp prior to leaving the facility. Livers were transported in ESP-Gro medium (Gigacyte, Branford, Conn.; catalog #1101-250). Livers received in the laboratory were weighed, photo-documented and prepared for perfusion. After grinding, the mixture was thawed and diluted to a media:biomatrix ratio of 1:48. This biomatrix slurry was then used for coating plates. After drying, the biomatrix was washed three times and then cells were applied. Adult liver cells attached within 10 minutes to the plates. Stem/progenitors can take longer (a few hours). However, for both stem/progenitors and adult liver cells, essentially 100% of the viable cells attach.

Media and Solutions.

All media were sterile-filtered (0.22-μm filter) and kept in the dark at 4° C. before use. To keep collagens stable in the biomatrix, the pH of the perfusion media for biomatrix scaffold preparation was kept at 7.5-8.0. RPMI-1640 (Gibco/Invitrogen, Carlsbad, Calif.) was used as the basal medium for preparation of biomatrix scaffolds and for hepatocyte or hepatic stem cell cultures. All reagents except those noted were obtained from Sigma (St. Louis, Mo.).

Perfusion Media for Biomatrix Scaffold Preparation.

(1). Perfusion wash and perfusion rinse: serum-free basal medium (e.g., RPMI-1640);
(2). Perfusion with detergent: 36 units/L PLA2 plus 1% SDC;
(3). Perfusion with high salt: 3.4M NaCl. with 0.1 mg/ml Soybean trypsin inhibitor;
(4). Perfusion with nucleases: 5 mg/100 ml RNase, 1 mg/100 ml DNase and 0.1 mg/ml soybean trypsin inhibitor (e.g., prepared in RPMI 1640).

Kuhota's Medium;

KM was designed originally for hepatoblasts[47] and now has been found effective for human hepatic progenitors[48] and for other endodermal progenitors including ones from biliary tree (Wang et al. "Multipotent stem/progenitor cells in human biliary tree give rise to hepatocytes, cholangiocytes and pancreatic islets" *Hepatology*, 2011, in press) and pancreas (Wang, Y and Reid L, unpublished data). It consists of any basal medium (here being RPMI 1640) with no copper, low calcium (0.3 mM), 10-9 M Selenium, 0.1% BSA, 4.5 mM Nicotinamide, 0.1 nM Zinc Sulfate heptahydrate (from Specpure, Johnson Matthew Chemicals, Royston, England), $10^{-8}$M hydrocortisone, 5 μg/ml transferrin/Fe, 5 μg/ml insulin, 10 μg/ml high density lipoprotein, and a mixture of free fatty acids that are added bound to purified human serum albumin.

To differentiate cells to an adult fate, a serum-free, hormonally defined medium (HDM) tailored to the adult cell type desired can be used. For example, we used an HDM for the adult liver fate consisting of KM supplemented further with calcium to achieve a 0.6 mM concentration, $10^{-12}$M copper, 1 nM tri-iodothyronine (T3), 7 ng/ml glucagon, 20 ng/ml of FGF, 2 g/L galactose, 10 ng/ml Oncostatin M (OSM), 10 ng/ml epidermal growth factor (EGF), 20 ng/ml hepatocyte growth factor (HGF), and $10^{-8}$M hydrocortisone.

The cells were seeded in this HDM serum-free if plating on the scaffolds; in circumstances in which enzymes were used for processing cells or tissues, then we supplemented the HDM with 5% FBS (HyClone, Waltham, Mass.) for a few hours and then switched to serum-free HDM thereafter. In parallel, control experiments, cultures were kept in the HDM with 5% FBS throughout, but we found that the presence of serum caused cells to lose differentiated functions with time. The soluble factors requirements are less than normal for cultures on other substrata given that so many of the factors are bound to the biomatrix scaffolds. The soluble factors requirements are less than normal for cultures on other substrata given that so many of the factors are bound to the biomatrix scaffolds.

Characterization of Intact Vascular Trees in the Liver Biomatrix Scaffolds.

The branching and ramifying matrix remnants of the vasculature including the network of capillaries in the rat liver biomatrix scaffold have been visualized by light and fluorescence microscopy, respectively. Rhodamine-labeled 250 kDa dextran particles were injected into the liver biomatrix scaffold through the remnant of the portal vein to check the integrity of the matrix remnants of the vasculature system in the biomatrix scaffolds. A movie was prepared using a Leica MZ16FA fluorescence dissecting microscope (motorized).

Human Fetal Liver Processing.

Fetal liver tissues were provided by an accredited agency (Advanced Biological Resources, San Francisco, Calif.) from fetuses between 16-20 weeks gestational age obtained by elective pregnancy terminations. The research protocol was reviewed and approved by the Institutional Review Board for Human Research Studies at the University of North Carolina at Chapel Hill. Suspensions of fetal human liver cells were prepared as described previously[48,49]. Briefly, processing was conducted in RPMI 1640 supplemented with 0.1% bovine serum albumin, 1 nM selenium and antibiotics. Enzymatic processing buffer contained 300 U/ml type IV collagenase and 0.3 mg/ml deoxyribonuclease at 32° C. with frequent agitation for 15-20 min. Enriched suspensions were pressed through a 75 gauge mesh and spun at 1200 RPM for 5 min before resuspension. Estimated cell viability by trypan blue exclusion was routinely higher than 95%.

Enrichment of hHpSCs and Culture on Biomatrix Scaffolds.

We used two methods for the hHpSCs purification or enrichment:

1) Culture selection. Approximately $3 \times 10^5$ cells were plated on a 10 cm tissue culture dish and in KM. Medium was changed every 3 days. Colonies formed within 5-7 days and were observed for up to 3 months. We picked colonies by hand after 14-18 days using an inverted microscope (IX-FLAIII; Olympus, Japan and Melville, N.Y.).

2) Magnetic immunoselection of multipotent hepatic progenitor subpopulations (hHpSCs and hHBs) was achieved by selection of cells positive for epithelial cell adhesion molecule (EpCAM, CD326) using magnetic bead immunoselection technologies with the Miltenyi Biotech MACS system (Bergisch Gladbach, Germany) following the manufacturer's instructions[50]. Briefly, the dissociated cells were incubated with EpCAM antibody bound to magnetic microbeads for 30 min at 4 C, and were separated using a magnetic column separation system from Miltenyi following the manufacturer's recommended procedures.

Cultures were seeded with either 250 hHpSC colonies, or $5 \times 10^5$ enriched hHpSCs or $2.5 \times 10^5$ primary adult hepatocytes. Medium was replaced daily and collected medium was stored at $-20°$ C. for further analysis. Cells cultured on Collagen type I coating 24-well plates served as control.

Adult Rat Hepatocyte Isolation.

Freshly isolated suspensions of rat hepatocytes were obtained from 3-month old adult male Lewis rats (Charles River Laboratories, Wilmington, Mass.) weighing 200-250 g. An improved two-step perfusion method as previously described[49] was used for rat hepatocyte isolation and purification. The liver was perfused for 10-15 minutes with a calcium-free buffer containing EGTA and then collagenase in a calcium-containing buffer for 10-15 minutes. The liver was then mechanically dissociated by pressing the digested liver through cheese cloth and then sequentially filtering the cell suspension through sieves of narrowing mesh size. The cells were washed twice and then pelleted at 50 g. Viability was defined by counting the cells after trypan blue staining. Routinely, 200-300 million cells per rat were isolated with 89-96% viability and >99% purity.

Human Adult Liver Cell Isolation and Culture.

Fresh human liver cell suspensions were obtained from CellzDirect. (now a part of Invitrogen, RTP, NC). Suspensions were processed per CellzDirect methods then resuspended in HeptoMAIN medium (Catalog #1103-250; Giga-Cyte, Branford, Conn.) plated at $1.88 \times 10^5$ cells/cm2 into multi-well plates coated with liver biomatrix scaffolds or onto type I collagen (1 µg/ml; Meridian Catalog #A33704H).

Collagen chemistry analysis. The amount of collagen in biomatrix scaffolds was evaluated based on the hydroxyproline (hyp) content. Samples of whole livers and of biomatrix scaffolds were pulverized, washed and lyophilized. Aliquots were then hydrolyzed and subjected to amino acid analysis[51], and the collagen content per total protein was estimated based on the hyp value of 300 residues/collagen.

Quantitative Analysis of DNA and RNA Content.

To assess total DNA remaining in the decellularized liver biomatrix, both fresh rat liver tissue and decellularized biomatrix were weighed, cut and digested with Proteinase K and total cellular DNA was isolated[52]. To assess total RNA remaining in the decellularized liver biomatrix, both fresh rat liver tissue and decellularized rat liver biomatrix were weighed and then homogenized in TRizol solution (Invitrogen), and total cellular RNA was isolated.

Growth Factor Assays.

Samples of rat livers, rat liver biomatrix scaffolds, human bile duct tissue and human bile duct biomatrix scaffolds (two samples each) were sent to RayBiotech, Inc (Norcross, Ga.) for analysis of growth factors. The samples were homogenized, prepared as lysates, and then assayed with 1 mg/ml protein, yielding fluorescence, defined in fluorescent intensity units (FIUs). Semi-quantitative growth factor assays were done using the RayBio® Human Growth Factor Arrays, G Series 1. The FIUs were reduced by that from negative controls for non-specific binding and normalized to protein concentration. The data from the duplicates were averaged. Four arrays were used enabling the survey for 40 growth factors. Although the assay was developed for human growth factors, there is sufficient overlap in cross-reaction to rat growth factors to permit use for both the rat and human samples.

Transmission and Scanning Electron Microscopy (TEM and SEM).

For TEM, the biomatrix scaffolds were rinsed with phosphate buffered saline (PBS) and fixed in 3% glutaraldehyde/0.1 sodium cacodylate, pH 7.4 overnight. Following three rinses with sodium cacodylate buffer, the biomatrix scaffolds were postfixed for 1 hour in 1% osmium tetroxide/0.1 sodium cacodylate buffer. After rinsing in deionized water, it was dehydrated and embedded in Polybed 812 epoxy resin (Polysciences, Niles, Ill.). The biomatrix scaffolds were sectioned perpendicular to the substrate at 70 nm using a diamond knife. Ultrathin sections were collected on 200 mesh copper grids and stained with 4% aqueous uranyl acetate for 15 minutes, followed by Reynolds' lead citrate for 7 minutes. Samples were viewed using a LEO EM910 transmission electron microscope operating at 80 kV (LEO Electron Microscopy, Oberkochen, Germany). Digital images were acquired using a Gatan Orius SC1000 CCD Digital Camera and Digital Micrograph 3.11.0 (Gatan, Pleasanton, Calif.).

For SEM, after fixation and rinses, the biomatrix scaffolds were dehydrated and transferred in 100% ethanol to the Balzers CPD-020 critical point dryer (Bal-Tee AG, Balzers, Switzerland), and dried using carbon dioxide as the transition solvent. The matrix was mounted on aluminum specimen supports with carbon adhesive tabs, and coated with a 10 nm thickness of gold-palladium metal (60:40 alloy) using a Hummer X sputter coater (Anatech, Worcester Mass.). Samples were examined using a Zeiss Supra 55 FESEM at an acceleration voltage of 5 kV and digital images were acquired using Zeiss SmartSEM software (Carl Zeiss SMT, Germany and Thornwood, N.Y.).

Immunocytochemistry and Immunohistology.

For the fluorescent staining of cultured cells on biomatrix scaffolds, cells were fixed with 4% paraformaldehyde (PFA) for 20 min at room temperature, rinsed with HBSS, blocking with 10% goat serum in HBSS for 2 h, and rinsed. Fixed cells were incubated with primary antibodies at 4° C. overnight, washed, incubated for 1 h with labeled isotype-specific secondary antibodies, washed, counterstained with 4',6-diamidino-2-phenylindole (DAPI) for visualization of cell nuclei and viewed using a Leica DMIRB inverted microscope (Leica, Houston, Tex.).

For immunohistochemistry, the biomatrix scaffolds were fixed in 4% PFA overnight and stored in 70% ethanol. They were embedded in paraffin and cut into 5-μm sections. Sections were deparaffinized, and the antigens were retrieved. Endogenous peroxidases were blocked by incubation for 30 min in 0.3% H202 solution. After blocking with 10% horse serum, primary antibody was applied at 4° C. overnight; secondary antibody and ABC staining were performed using the RTU Vectastain kit (Vector Laboratories, Burlingame, Calif.). Vector Nova RED was used as substrate. Sections were dehydrated, fixed and embedded in Eukitt Mounting Media (Electron Microscopy Sciences, Hatfield, Pa.), and were analyzed using an inverted microscope. Antibodies used for liver sections and for cultures are listed in Table 4.

Reverse-Transcription Polymerase Chain Reaction (RT-PCR) Analysis.

The hHpSCs are cultured on cell culture plates, and the colonies were transferred onto biomatrix scaffold. After further culture for 7 days, the colonies were lysed for RT-PCR. Total RNA was extracted using an RNeasy Plus Mini Kit (Qiagen GmbH, Valencia Calif.) as per the manufacturer's instructions. Reverse transcription was carried out with the SuperScript First-Strand Synthesis System for RT-PCR (Invitrogen, Carlsbad, Calif.). HotStarTaq Master Mix Kit (Qiagen) was used for PCR. PCR primers were listed in Table 5.

LIVE/DEAD Assay and Cell Viability Assay.

A LIVE/DEAD viability assay kit (Molecular Probes/Invitrogen, Carlsbad, Calif.) was used for the adhesion and proliferation assays. The hHpSCs or hepatocytes were incubated with two probes, calcein-AM (Live, light grey) and ethidium homodimer-1 (EtdD-1, Dead), for intracellular esterase activity and plasma membrane integrity, respectively. Specimens were observed under a fluorescence Olympus SZX12 stereomicroscope (OLYMPUS, Japan and Melville, N.Y.). A resazurin cell viability assay kit (Biotium, Hayward, Calif.) was used following the manufacturer's manual. Briefly, 10% of resazurin solution was added into culture medium and incubated at 37° C. overnight. Absorbance $OD_{570}$-$OD_{600}$ was obtained using a Biotek Synergy HT multi-detection microplate reader (Winooski, Vt.) and the viability curve plotted. All experiments were carried out three times using a minimum of three samples per experimental condition.

Hepatic Specific Functional Assays.

CYP450 3A4 activity was detected using a P450-Glo™ Screening System (Promega, Madison, Wis.). Briefly, the cultured cells were incubated with medium containing the luminogenic CYP3A4 substrate, luciferin-PPXE for CYP, for 4 hours at 37° C. The luciferin detection and analysis was performed per the manufacturer's instructions with a Wallace Victor2 Multilabel Counter (now part of Perkins/Elmer in Waltham, Mass.). Quantitative albumin secretion was done using a human albumin ELISA quantitation kit (Bethyl Laboratories, Montgomery, Tex.). For urea synthesis assays, the cells were incubated with 2 mM ammonium for 24 hours and the supernatant was collected and assayed with the Quantichrom urea assay kit (Bioassay Systems, Hayward, Calif.). The supernatant from one sample for each culture condition was assayed in triplicate and the experiment was repeated 3 times.

Statistical Analysis.

Experiments were repeated at least 2-3 times with duplicate or triplicate samples for each condition. Data from representative experiments are presented, whereas similar trends were seen in multiple trials. All error bars represent S.E.M.

Biomatrix Scaffolds are Prepared with a Novel Four-Step Protocol.

Biomatrix scaffolds were prepared using a protocol comprised of delipidation followed by high salt extractions and using perfusion methods (FIG. 1). A detailed presentation of the protocol is given in the methods. This is achieved by a novel four step protocol: 1) gentle delipidation; 2) washes with buffers with salt concentrations from about 2.0M to about 5.0M (e.g., 2.0M-2.5M, 2.6M-3.0M; 3.1M-3.5M, 3.6M-4.0M, 4.1M-4.5M; 4.6M-5.0M), salt concentrations known to maintain the collagens in an insoluble state[23] (the exact concentration and the pH of the buffers is dictated by 2.5 the collagen types in the tissue), concentrations known to maintain collagens in an insoluble state[23]; 3) nuclease treatment to eliminate residual nucleic acids; and 4) rinses with a basal medium to eliminate the detergent, salt and nuclease residues as well as to equilibrate the matrix components with the medium (FIG. 1A).

Figure 8:
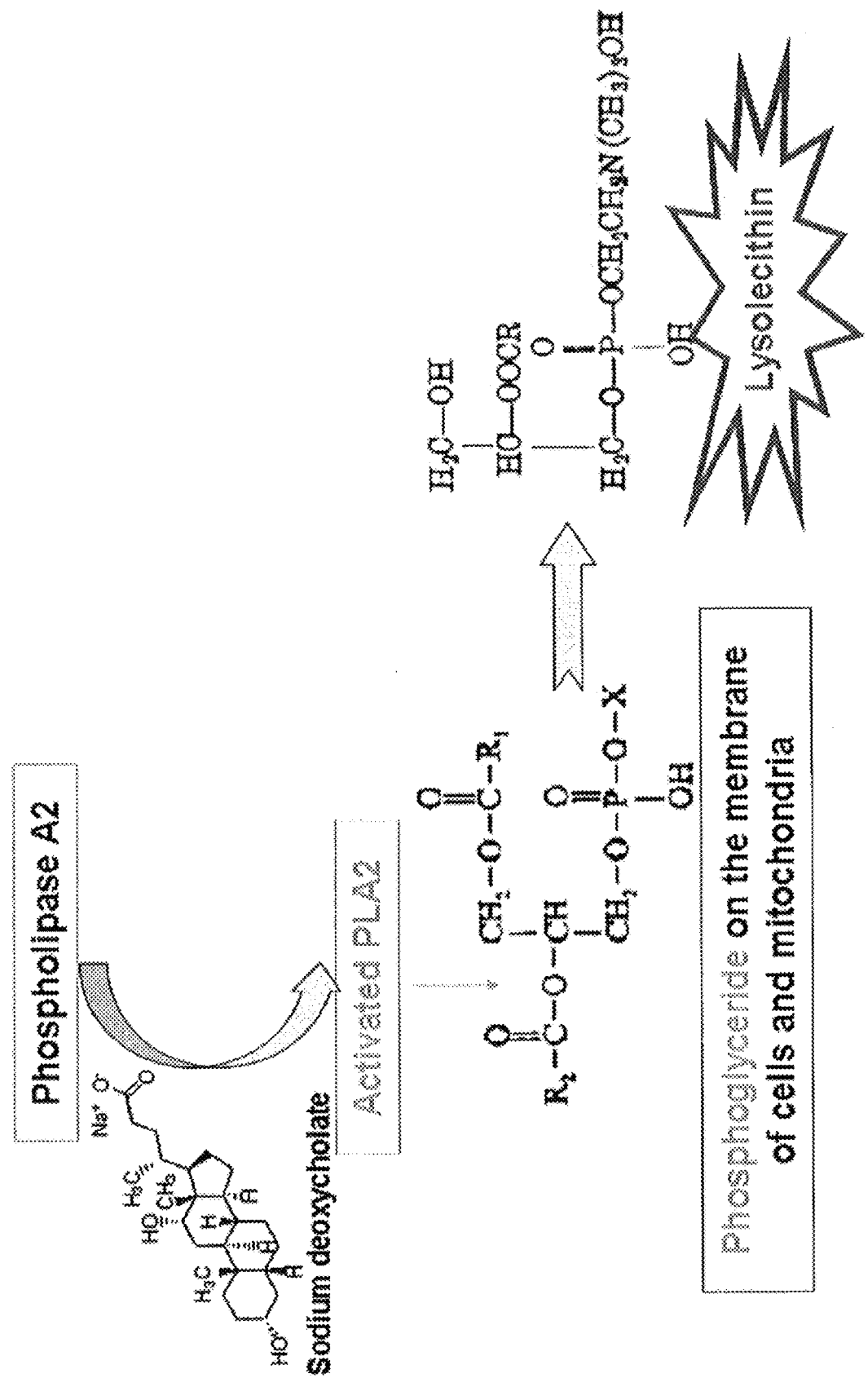
FIG. 8. Activation of phospholipase A2 by sodium deoxycholate to produce lysolecithin. Principle of the protocol: Phospholipase A2 (PLA2) activated by sodium deoxycholate will degrade the phosphoglyceride located on the cytoplasmic membrane and mitochondrial membrane into lysolecithin, a powerful surfactant, which induces cell necrosis.

The choices of the rinse media or the buffers for the nucleases can be any of a number of options as long as the salt concentration and ionic strength are such as to maintain the matrix components in an insoluble state. The choice of the delipidation method is critical to be effective and yet gentle. We chose a combination of sodium deoxycholate (SDC) and Phospholipase A2 (PLA2) to rapidly degrade the phosphoglyceride located on the cytoplasm membrane and mitochondrial membrane into lysolecithin, a powerful surfactant, which can induce necrosis and cytolysis. The reactive formula is shown in FIG. 8. We avoided harsh detergents, such as sodium dodecyl sulfate (SDS) or Triton-X 100, which might dissolve some matrix components such as the glycosaminoglycans (See review by Gilbert et al. "Decellularization of tissues and organs" *Biomaterials* 27:3675-3683 (2006)).

We avoided prolonged exposure of the scaffolds to the enzymes from the disrupted cells during delipidation and the high salt washes, because they can greatly decrease the content of elastin and the content of glycosaminoglycans (GAGs) such as heparan sulfates (HS), chondroitin sulfates (CS), dermatan sulfates (DS) and heparins (HP), which are sites at which cytokines and growth factors bind[24]. We used soybean trypsin inhibitor and careful control of the pH (7.5-8.0), temperature (20° C.), and time (30-60 mins) to limit the activity of the proteases derived from disrupted cells.

We perfused the whole tissue through relevant vasculature (e.g., portal vein in the liver), enabling us to rapidly isolate (within a few hours) a biomatrix scaffold with minimal loss of matrix components. The rapidity of the isolation is due to the initial step with detergent that delipidates the tissue within approximately 30-60 minutes (not hours or days as in protocols used by others). The resulting biomatrix scaffolds are translucent or white (FIG. 1). Moreover, using this perfusion method, we maintained the primary vasculature channels, portal and hepatic vein and most of the vascular branches in the liver, which increased the decellularization efficiency. Fluorescent rhodamine-labeled dextran particles perfused through the biomatrix scaffolds remained within the remnants of the vasculature demonstrating that they are patent (FIG. 1E) There is a progressive flow of the dye from large vessels to the fine blood vessel branches along the channels without leakage. This fact will be helpful in revascularization of the scaffolds as a means of preparing engineered tissues for either three-dimensional culture and/or for implantation ex vivo.

Figure 2:
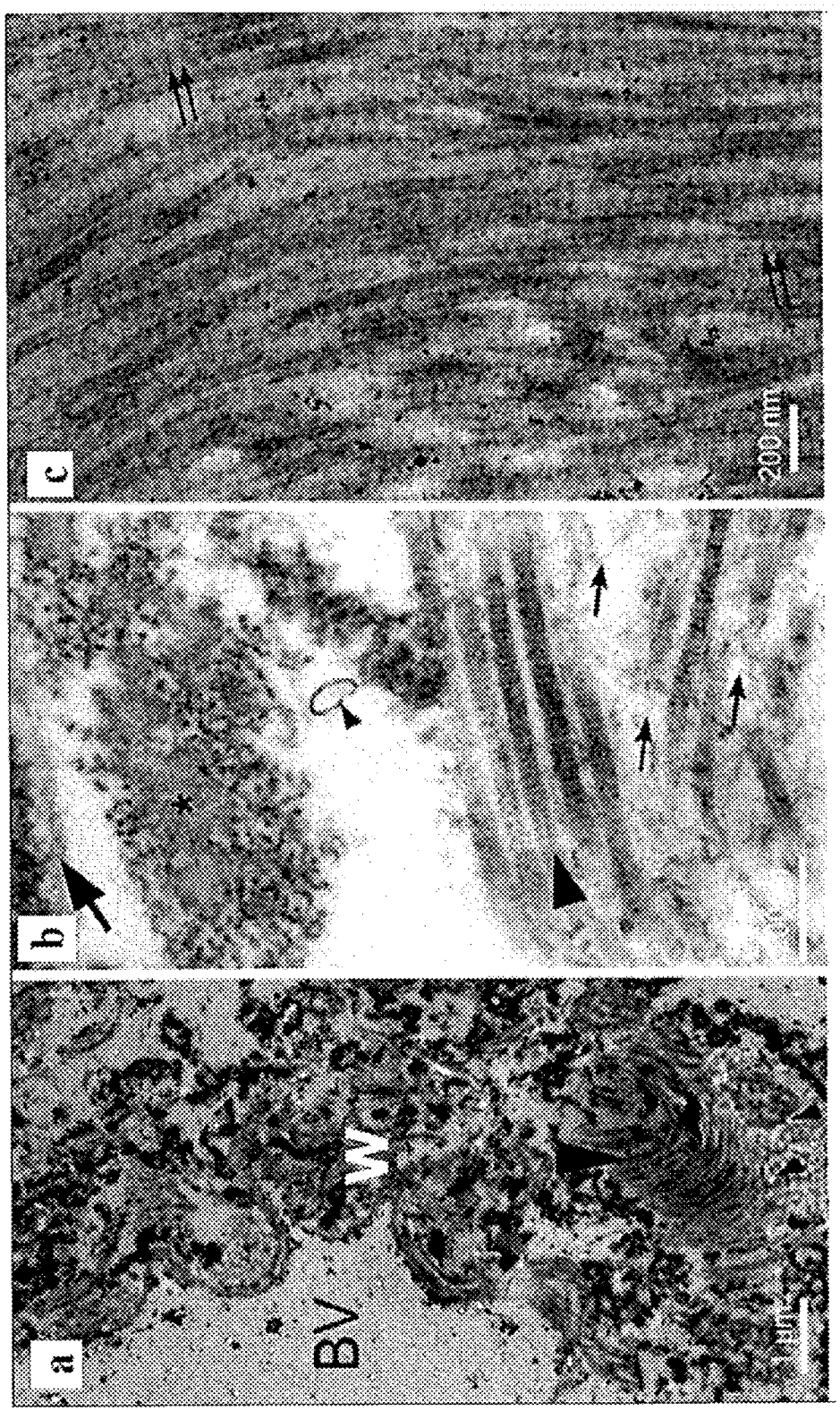
FIG. 2, Panels A-H. TEM (A-C) and SEM (D-H) images of rat liver biomatrix scaffolds. (A) Low magnification of blood vessel (BV) with a thick wall (W). Collagen Type I (large arrowhead) is numerous and contains cross-sections of individual fibers that do not take up heavy metal stains (white dots, small arrowheads). (B) Higher magnification of a vessel wall shows basement membrane (large arrow), amorphous elastin (*) and associated elastic fibers, a rare membrane vesicle remnant (small arrowhead), a collagen Type I banded fiber (arrowhead) and small fibrils (small arrows). The small fibrils are probably fibrillin (Type VI collagen) that associates closely with and helps organize Type I collagen. (C) High magnification of Type I collagen with 64 nm banding pattern (arrows). (D) Low magnification of a vessel with thin wall (BV) and the wall of a larger vessel (W). (E) At higher magnification, the large vessel wall (W) is scalloped, consistent with hepatic artery of a portal triad, see (A). Beneath the wall are numerous Type I collagen bundles (large arrow) linked by long branching thin, reticular (Type III) collagen fibrils (small arrows). (F) A large bundle of Type I collagen has characteristic parallel fibers (large arrow) associated with a variety of smaller fibers (arrow) and nodular or beaded fibers (arrowhead). (G) 3D-meshwork of large/small fibers interlinked in a plane that firms a boundary such as to a liver sinusoid. (H) Higher magnification of the meshwork showing a variety of fibers (arrows): Type III collagen (larger diameter straight), elastic fibers or Type VI collagen.
Figure 2:
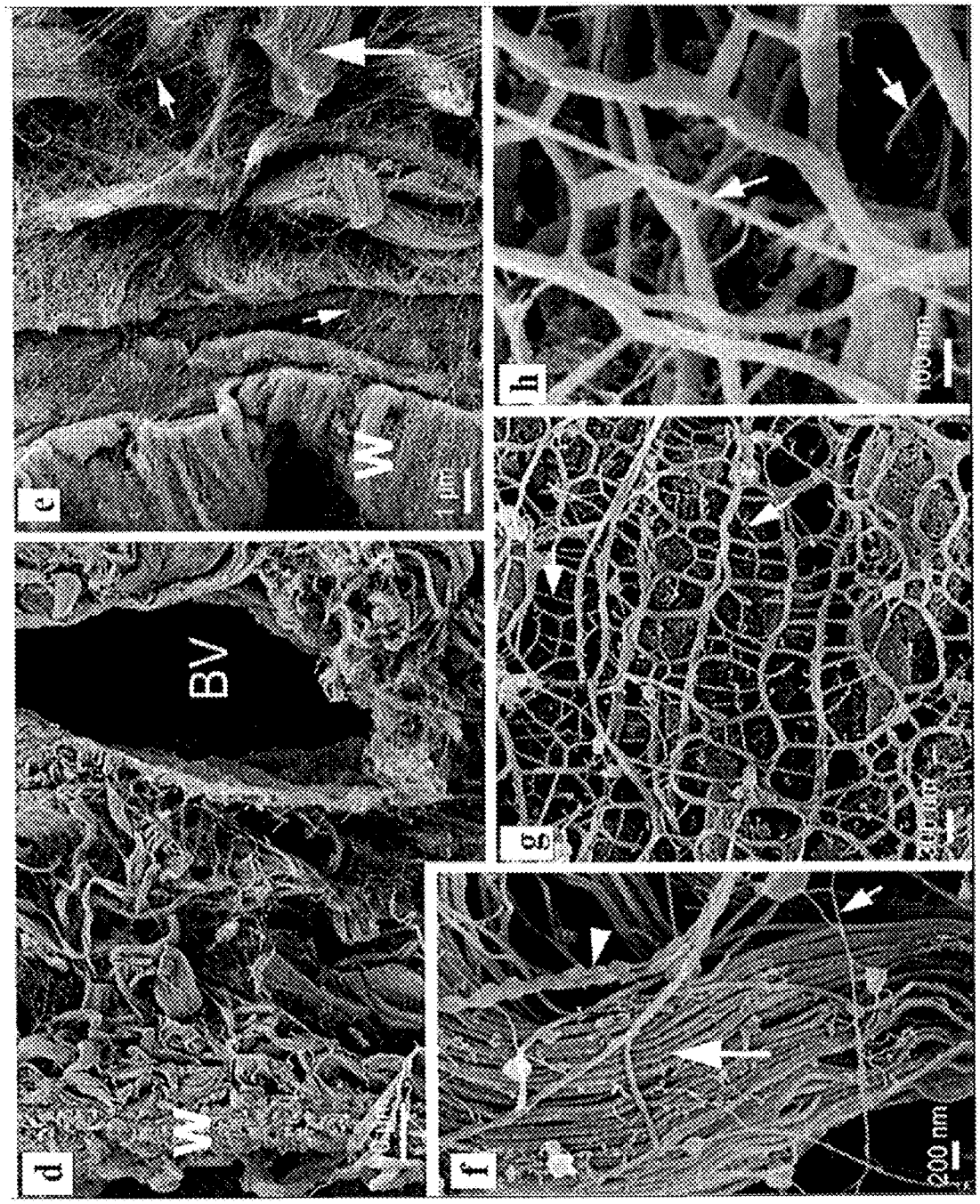
Figure 3:
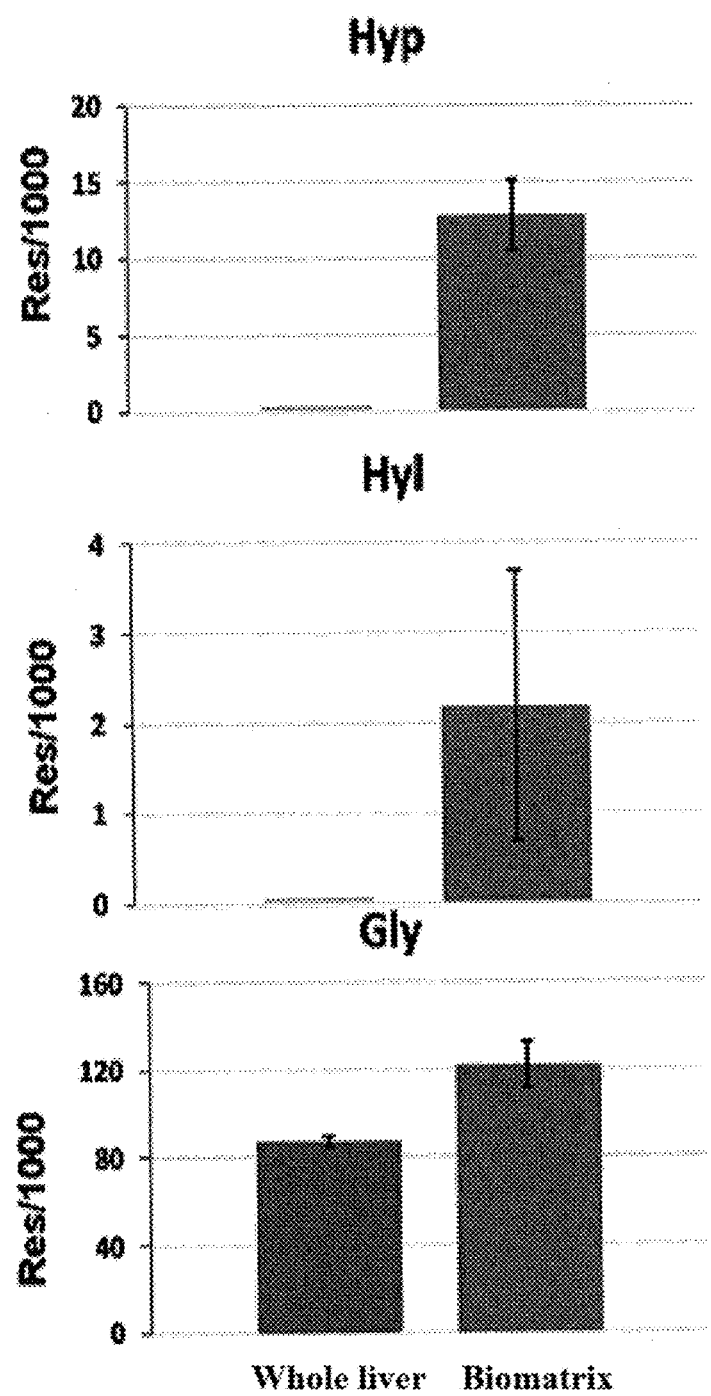
FIG. 3, Panels A-B. Chemical analysis of collagens and expression of extracellular matrix (ECM) components in biomatrix scaffolds. (A) The content of three amino acids, all found in collagens: hydroxyproline (Hyp), hydroxylysine (Hyl), and glycine (Gly). The numbers represent the residues of each amino acid/1,000 amino acids. The data indicate the dramatic increase in the collagen content in the decellularization process going from <0.2% in liver to more than 15% in the biomatrix scaffolds. (B) Immunohistochemical staining of matrix molecules in biomatrix scaffolds, shows distribution in liver biomatrix scaffolds of laminin (LAM), heparan sulfate (HS), collagen type III (COL3) and fibronectin (FN) and typical basement membrane proteins in association with remnants of blood vessels. At higher magnification, one can observe main members of basement membrane, including type IV collagen (COL4), entactin (Ent; also called nidogen), laminin (LAM) and perlecan (Per), a form of HS-PG in the portion of the scaffolds near the portal triads.
Figure 3:
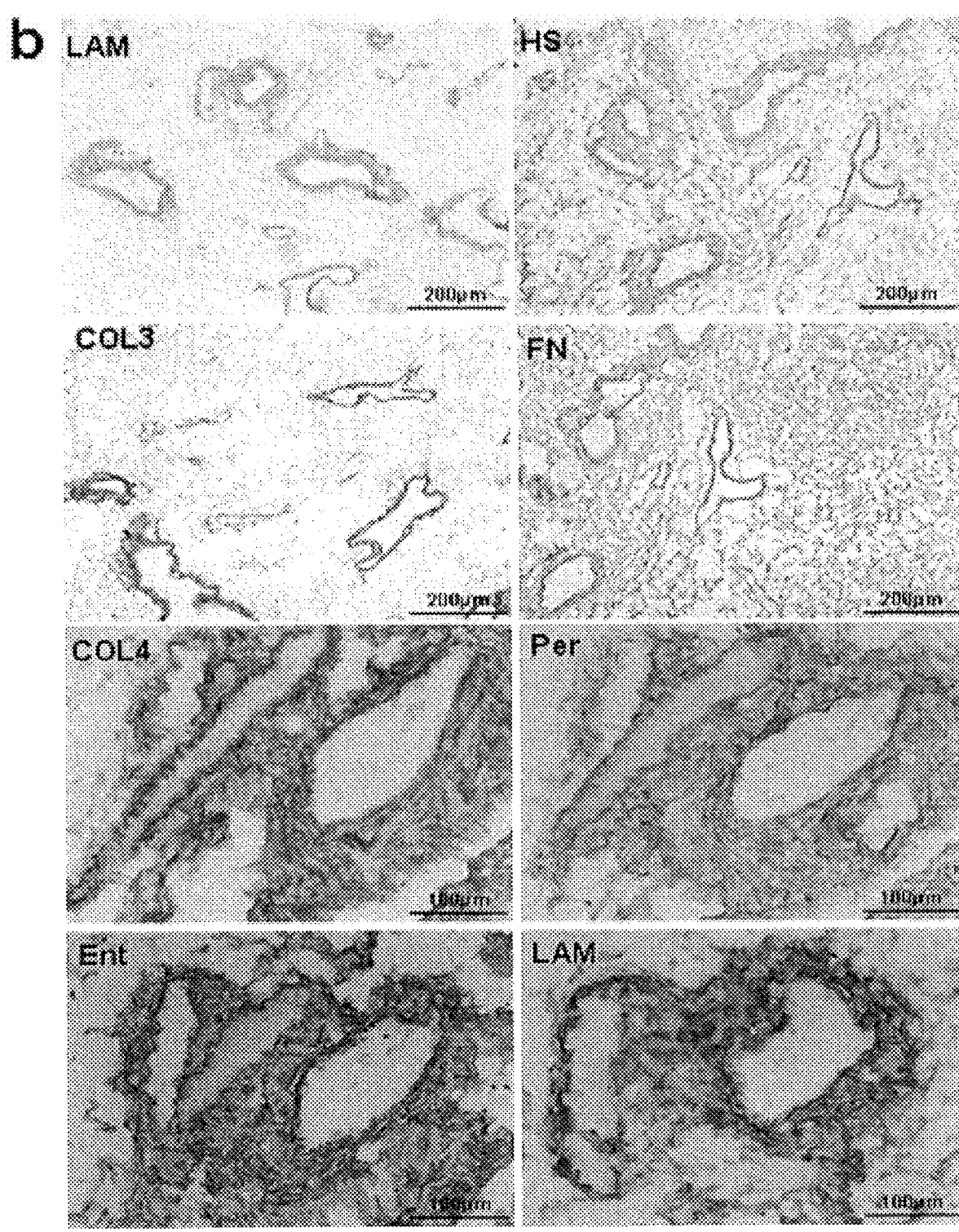

When sectioned, the scaffolds retain the histological structure of the original tissue, including the recognizable remnants of major histological entities such as the blood vessels, bile ducts, and Glisson's capsule (GC) (FIG. 1). Compare FIGS. 1B1 and 1D1, in which a section of the liver tissue is contrasted with that of a biomatrix scaffold. The matrix remnants of the muralia of parenchymal cells consisted of a lace-like network (FIGS. 1D2-1D3).

Collagen, Collagen Associate Proteins and Bound Cytokines are Maintained in the Biomatrix Scaffolds.

Figure 9:
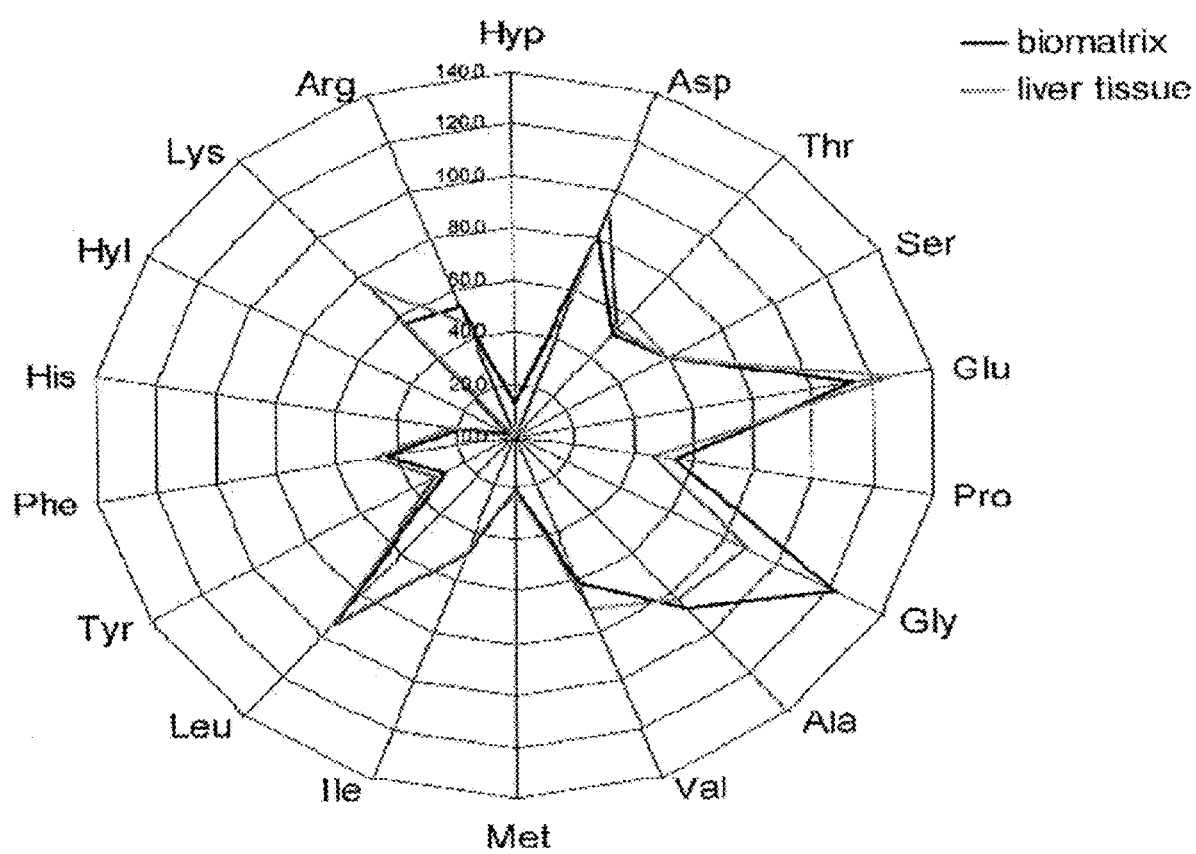
FIG. 9. Analysis of the collagen composition of rat livers versus rat liver biomatrix scaffolds. The amino acid composition of biomatrix (black) and whole liver (light grey) presented in the form of a Rose Diagram. A three-letter abbreviation is used for each amino acid analyzed. Tryptophan and cysteine were not analyzed. The numbers indicate the amino acid residues/1,000.
Figure 10:
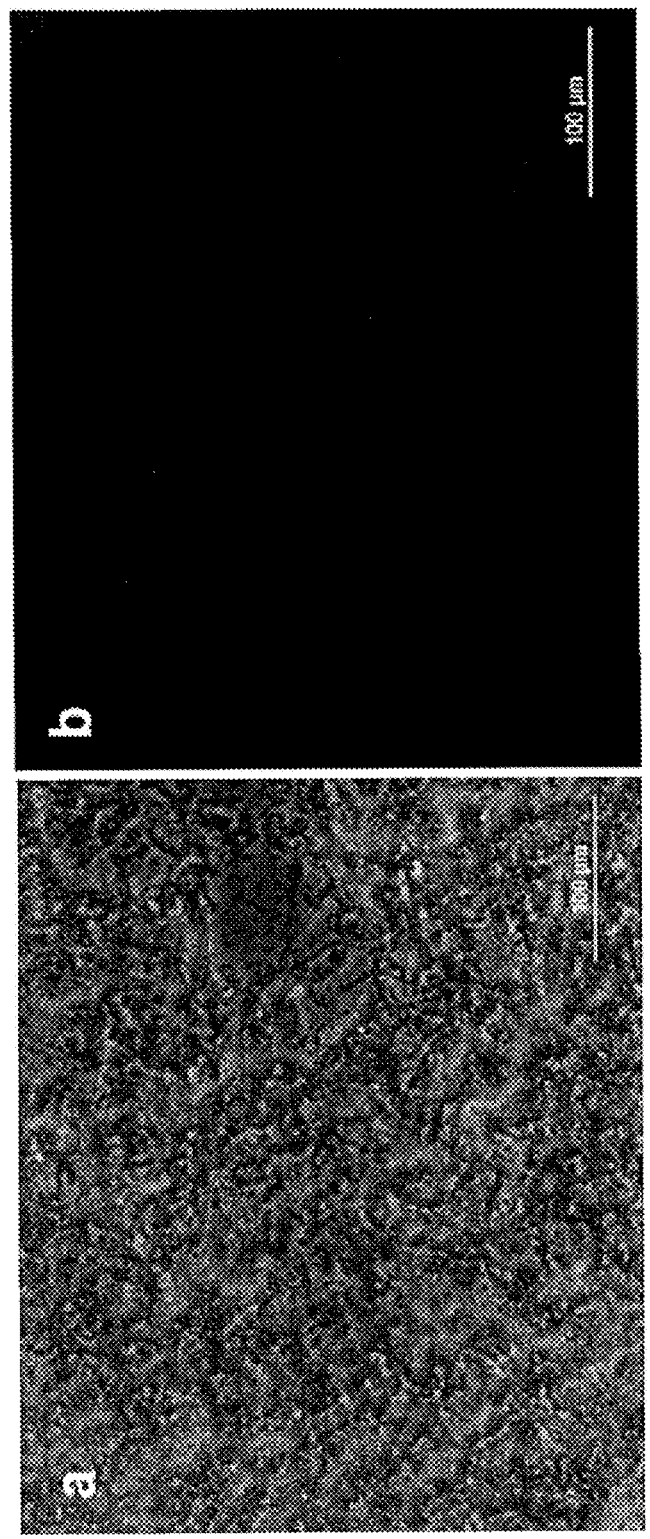
FIG. 10, Panels A-C. Nucleic acid analysis of rat liver biomatrix scaffold. Phase contrast photo (A) and fluorescent DAPI staining (B) of the liver biomatrix slide, and quantitative assays on total DNA and RNA from rat fresh liver tissue versus biomatrix scaffold (C).

The amount of collagen in biomatrix scaffolds was evaluated by amino acid analysis by methods used previously[25]. Because hydroxyproline (Hyp) is unique to collagens and collagenous proteins, the collagen composition relative to total protein was expressed as residues of Hyp per 1,000 amino acids. The results demonstrated that the collagen content increased from almost undetectable levels, i.e., less than 0.2 residues of hydroxyproline (Hyp)/1,000 in liver, to 13 residues of Hyp/1,000 in biomatrix scaffolds. This indicates that delipidation and the high salt washes, described above, did not remove collagens, leaving almost all of the collagens in the biomatrix scaffolds. Detection of significant levels of hydroxylysine (Hyl), another collagen-associated amino acid, and higher levels of glycine (Gly) in biomatrix scaffold support our conclusion that collagen is markedly enriched in biomatrix scaffolds (FIGS. 2A, 9 and Table 2).

Using immunohistochemical and ultrastructural studies, we were able to identify in the scaffolds all known forms of collagens found in liver in situ including fibrillar collagens (collagen types I, III and V, 10-30 nm in diameter for fibrils and 500-3,000 nm for assembled fibers) and beaded filaments (possibly type VI). Those fibers and filaments are present in the subcapsular connective tissue layer lying beneath the mesothelial layer. Although typical structures of basement membranes were not found along the sinusoids from portal triads to central veins, we found that collagen type IV and some bound small fibrils form net-like, porous 3D lattices, serving as scaffolding for the parenchymal cells (FIG. 2). Collagen type I bundles can be viewed as the principal structure of the scaffolds to which other collagen types, glycoproteins, and proteoglycans are attached. In the space of Disse we found small bundles of collagen type I and fibers of collagen types III and VI as well as some type V, which is more abundant near portal triads and central veins. Representative immunohistochemistry data are presented in FIG. 3B, and a summary of matrix components and their location in normal liver tissue versus those in the biomatrix scaffolds are listed in FIG. 4D. Early studies in the development of the protocols for biomatrix scaffold preparation indicated that the bulk of the cytoskeletal components are lost in the washes. Still, we assessed the scaffolds by immunohistochemistry and found no evidence for tubulin, desmin or actin, trace amounts of cytokeratins 18 and 19, and low levels of vimentin scattered throughout the scaffolds. The matrix associated with the bile ducts and portions of the hepatic vascular systems (arterial and venous vessels) consists of typical basement membrane structures and so is quite distinctive from the thin layers of the matrix associated with the vascular structures found in the IO sinusoids. Laminin, entactin/nidogen, perlecan and collagen type IV are found in the portal triad, whereas only perlecan and some collagen type IV are found in the Space of Disse. Enormous amounts of hydrophobic, wavy elastin are present; it cross-links together and forms sheets and fibers restricted primarily to the subcapsular connective tissue, portal regions, and arterial walls. Fibronectins are ubiquitous and prevalent throughout the hepatic matrix and are especially abundant in the Space of Disse, where they form either fine filaments or granular deposits (FIGS. 2 and 3).

Immunohistochemistry indicates that the known proteoglycans in the tissue are preserved in the biomatrix scaffolds (FIGS. 3B, 4D). Among heterogeneous proteoglycans identified, syndecan was found intercalated and continuously along the sinusoids, and perlecan is more punctuate in the space of Disse. The forms of HS-PGs and CS-PGs are found throughout the remnants of the sinusoids in the biomatrix scaffolds and in patterns correlating with the known zonation of the liver tissue.

Proteoglycans and other matrix components are important reservoirs for cytokines and growth factors that bind tightly to their GAGs[26]. Most of the growth factors and hormones are found in the biomatrix scaffolds near to the concentrations found in the original tissue. In Table 6 the data are given from the lysates of rat livers versus rat liver biomatrix scaffolds, and in Table 3, parallel data are provided from human bile duct tissue versus bile duct biomatrix scaffolds. Interestingly, there were a few examples (e.g., bFGF) that were strongly enriched in liver biomatrix scaffolds over that found in liver lysates. The growth factors and cytokines bound are distinct qualitatively and quantitatively between the scaffolds of the liver versus bile duct tissue, implicating either tissue-specificity or species-specificity. Alternatively, it may be due, in part, to the fact that the bile duct scaffolds were prepared, from necessity, by shaking the tissue in the buffers on a rocker and not by perfusion through vasculature.

The Chemistry of the Biomatrix Scaffolds Correlates with Histology.

Figure 4A:
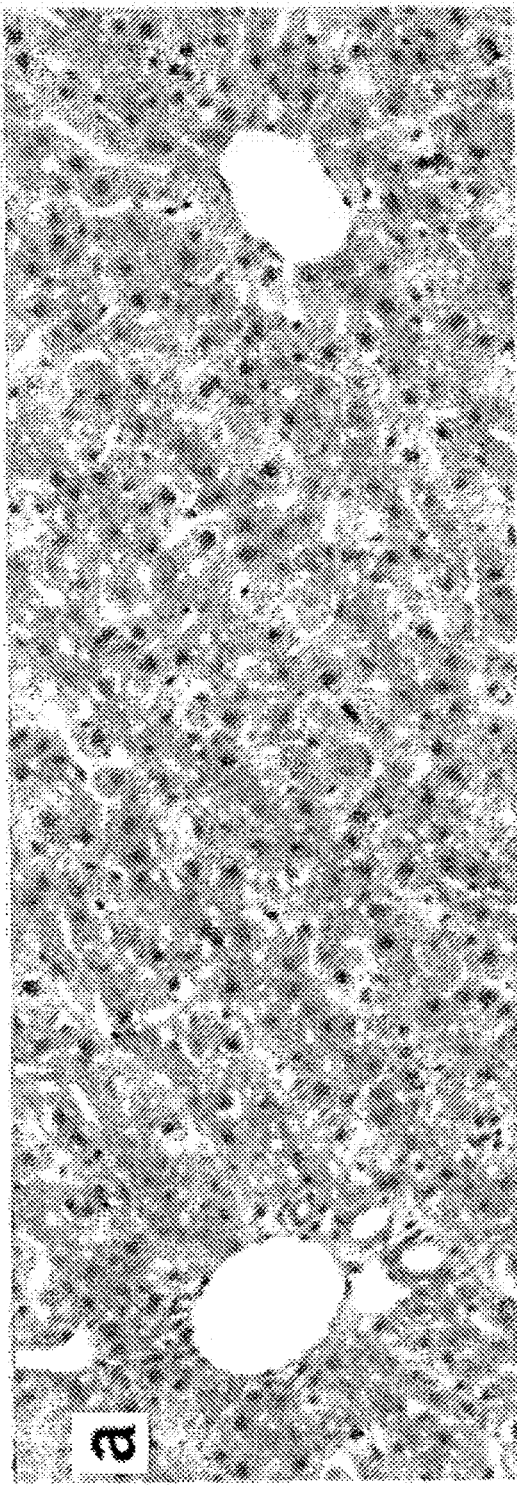
Figure 4B:
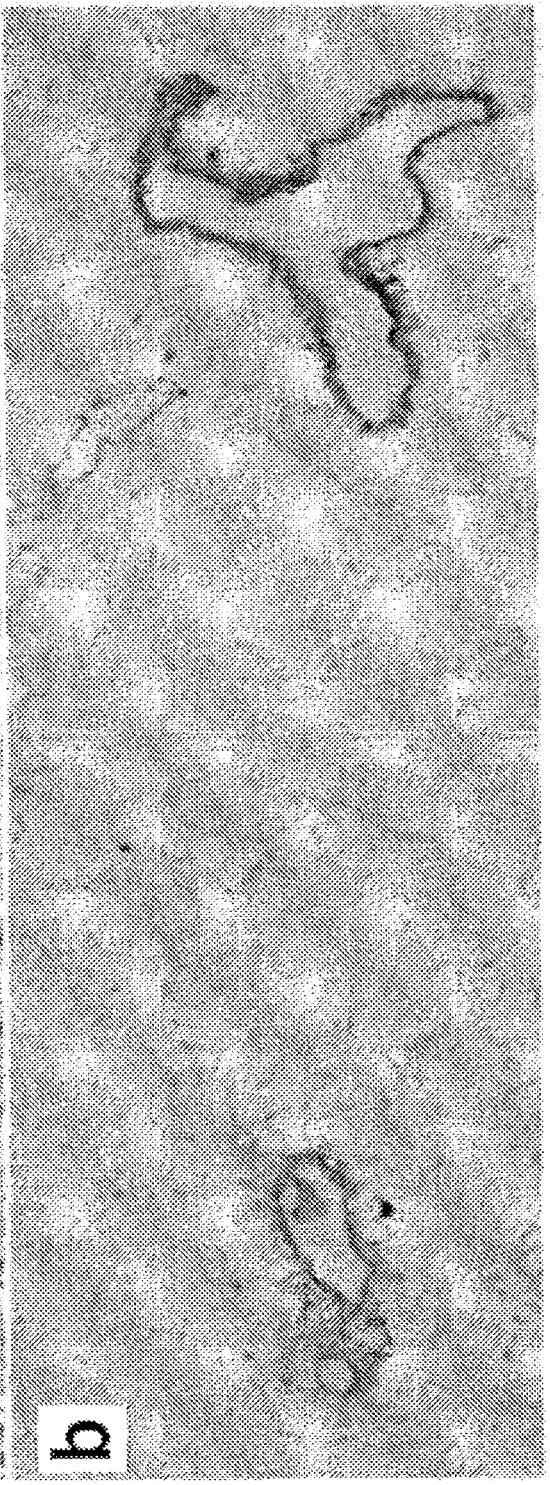
Figure 4C:
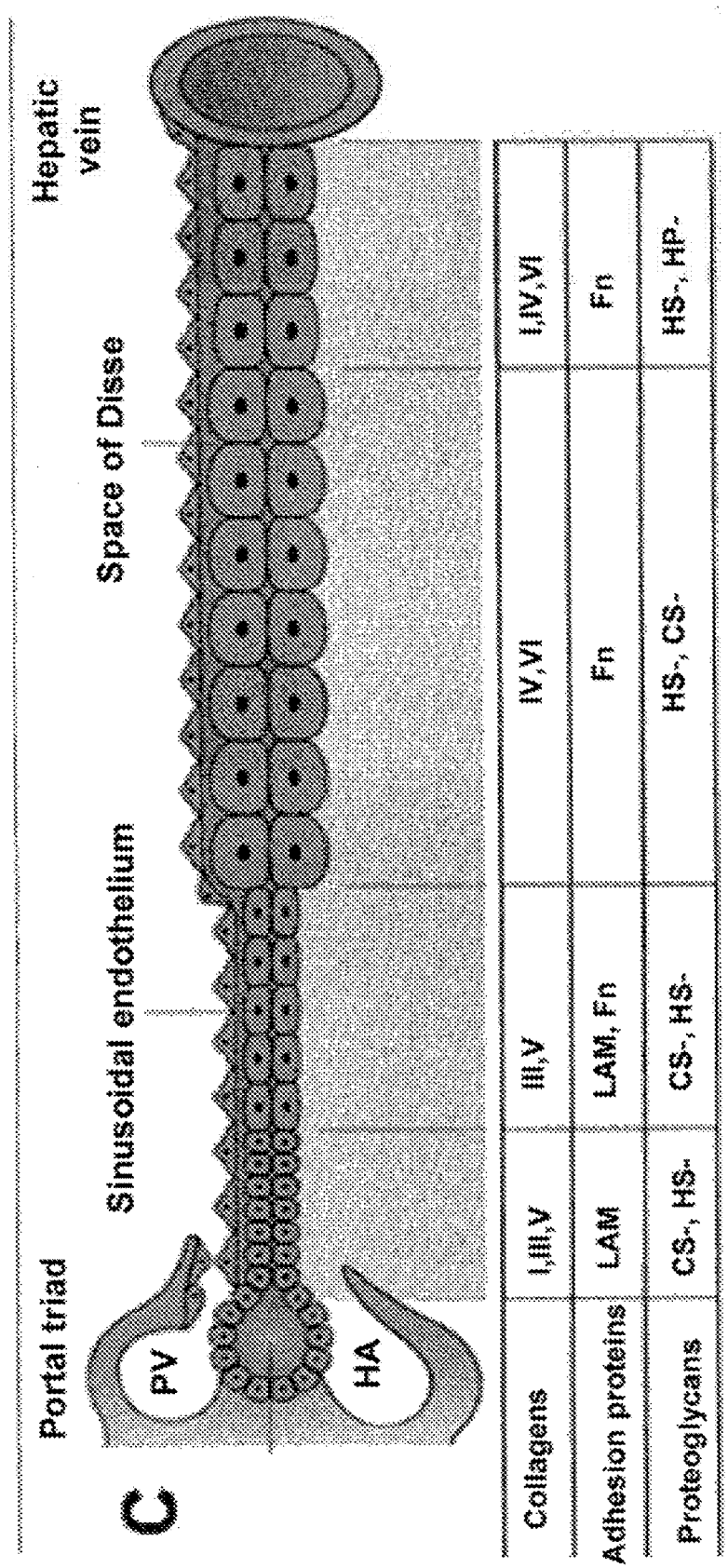

A significant feature of this new protocol is the retention of the matrix chemistry in patterns correlating with the hepatic acinar zones 1-3 from portal triad to central vein and with histological entities such as vascular channels and Glisson's Capsule (GC) as shown in FIGS. 4A-C. The matrix chemistry peripmially in zone 1 is similar to that found in fetal livers and consists, in part, of type III collagen, laminin, and forms of CS-PGs. It transitions to a different matrix chemistry in the mid-acinar (zone 2) and pericentral zones (zone 3) ending with a very stable matrix with high levels of type IV collagen and HP-PGs[27].

Myriad proteins (e.g., growth factors and hormones, coagulation proteins, various enzymes) are known to bind to the matrix and to be held stably via binding to the discrete and specific sulfation patterns in the GAGs or to other matrix components[24]. Thus, the matrix chemistry transitions from its start point in the stem cell niche having labile matrix chemistry associated with high turnover and minimal sulfation to stable matrix chemistries and having increasing amounts of sulfation with progression towards the pericentral zone. We expect that the maintenance of the natural architecture and matrix chemistry correlating with histology will facilitate recellularization in tissue engineering processes by guiding cells to specific sites on the biomatrix scaffolds and/or providing the proper mix of signals to drive expansion and/or differentiation into mature cells.

Biomatrix Scaffold can be Prepared from Different Tissues and Species.

The biomatrix scaffolds can be easily prepared from any tissue, normal or diseased and from any species. In FIGS. 13-16 we show biomatrix scaffolds from human pancreas, biliary tree, and duodenum and from rat and porcine pancreas. In FIGS. 5-7 and FIG. 12 are shown effects of bovine or of rat liver biomatrix scaffolds on hepatic cells. In addition, biomatrix scaffolds have been prepared from human abdominal aorta, iliac vein and from rat and pig intestine. Histological, ultrastructural, and immunohistochemical studies on the biomatrix scaffolds indicate a marked tissue specificity, but not species specificity, in their structure, chemical composition, and functions.

Biomatrix Scaffolds Induced and/or Maintained Differentiation of Cells.

Figure 5:
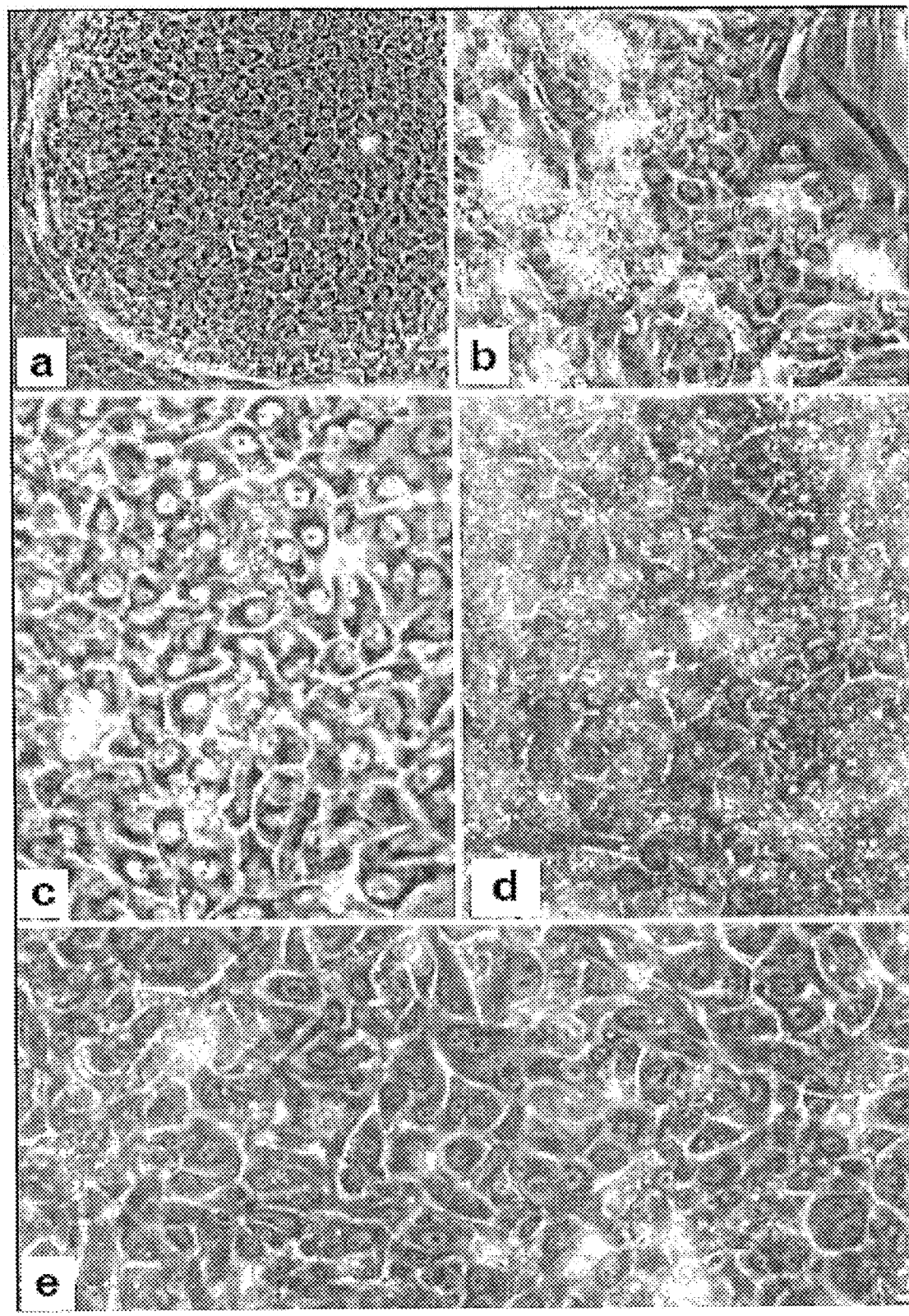
FIG. 5, Panels A-I. Characterization of hHpSCs on liver biomatrix scaffolds versus on type I collagen. Phase-contrast images (A-D) show the morphologic changes of hHpSC colonies derived from the same liver and cultured in serum-free Kubota's medium and on tissue culture plastic (A), one of the conditions for self-replication, versus in the differentiation conditions of the serum-free differentiation medium for liver, and on type I collagen (B) versus on bovine liver biomatrix scaffolds (C-E). Functional and fully viable cultures did not last more than 2 weeks on type I collagens. By contrast, those on the liver biomatrix scaffolds were viable and healthy and with a full repertoire of functions lasting at least a month. The cultures transitioned to cells by days 7-12 with increased cytoplasmic/nuclear ratio and marked glycogen expression (C) and then to ones with classic polygonal hepatocyte morphology interspersed by clear bile canaliculi (D), a culture morphology that persisted thereafter, as indicated in the representative culture at day 24 (E). RT-PCR assays show gene expression changes of hHpSCs under self-replication conditions on culture plastic (F) versus on rat liver biomatrix scaffolds on day 7 (G). We compared expression of hHpSC markers, including CXCR4 and EpCAM; early hepatocytic genes including CK19 (KRT19), HNF6, FOXA2, APP and low levels of albumin; mature hepatocytic markers including high levels of albumin (ALB), transferrin (TF), CYP450-3A4, tyrosine aminotransferase (TAT), and glucose-6-phoshatase (G6PC) and cholangiocytic genes, including CFTR, gamma glutamyl transpeptidase (GGT1), anion exchange 2 (AE2) and apical sodium-dependent bile acid transporter (ASBT). Biochemical assays measuring urea (H) synthesized in cultures on type I collagen versus on rat liver biomatrix scaffolds and CYP450-3A4 activity (I) in cultures on type I collagen versus on biomatrix scaffolds prepared from either rat or bovine livers. Table 7 provides a summary of quantitative measures comparing attachment, viability, growth, culture life span, and tissue-specific gene expression of hHpSCs freshly isolated, under culture conditions for self-replication (type III collagen), or under conditions for differentiation on collagen I, versus liver biomatrix scaffolds.
Figure 5:
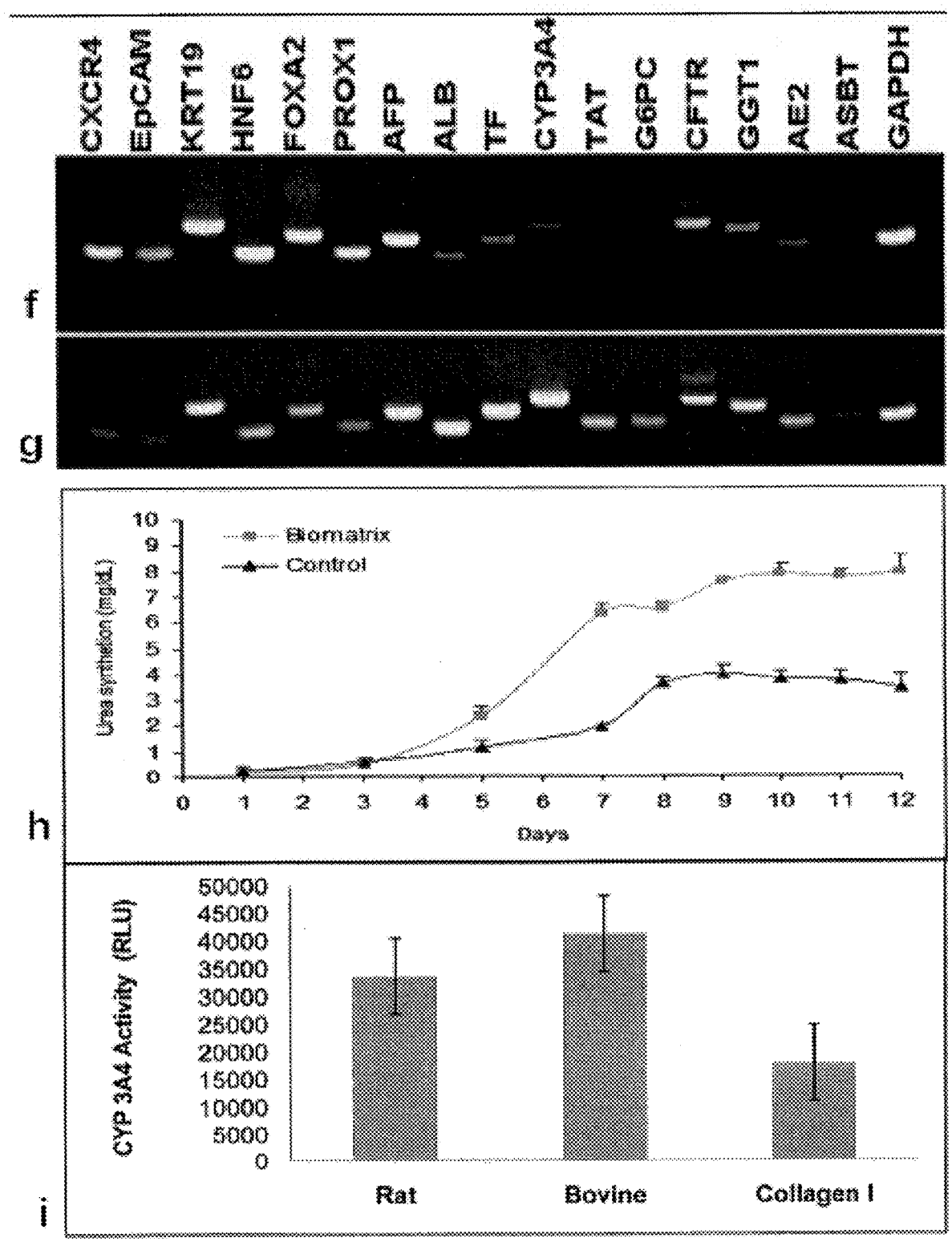
Figure 6:
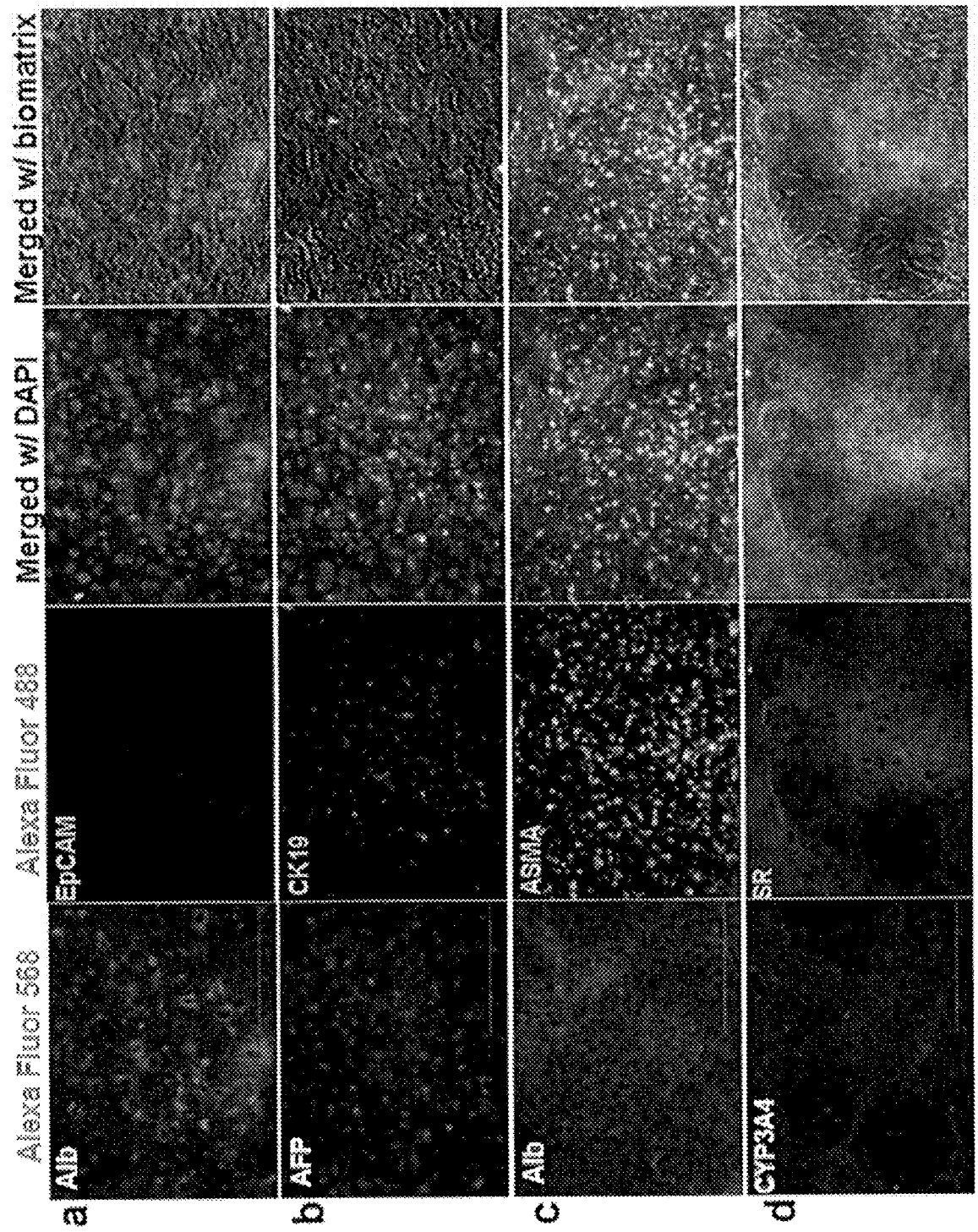
FIG. 6, Panels A-D. Immunofluorescence staining of cells lineage restricted from hHpSCs on biomatrix scaffolds. (A) Stained with hepatic specific marker:albumin (Alb, light grey) and hepatic stem cell surface marker: EpCAM (white). Note that cells plated on biomatrix scaffold do not express EpCAM. Scale bar=200 µm. (B) Stained with early hepatic marker a-fetoprotein (APP, light grey) and with an antibody to human cholangiocyte marker, cytokeratin 19 (CK19, white) that at this level of expression is indicative of mature cholangiocytes. The antibody to CK19 assay is human-specific and did not stain the residue at rat CK19 in the scaffolds not seeded with cells. The APP expression is low but still evident at day 7. Scale bar=200 µm. (C) Stained with Alb (light grey) and hepatic stellate cell marker, a-smooth muscle actin (ASMA, white). The expression of albumin and ASMA is a strong indication that both maturing hepatocytes and stellate cells are present. Scale bar=100 µm. (D) Stained with functional hepatic protein CYP450-3A4 (light grey) and cholangiocyte-specific marker, secretin receptor (SR, white) showing that the maturing hepatocytes and cholangiocytes are functional and express classic markers for these two cell types. Scale bar=200 µm.
Figure 11:
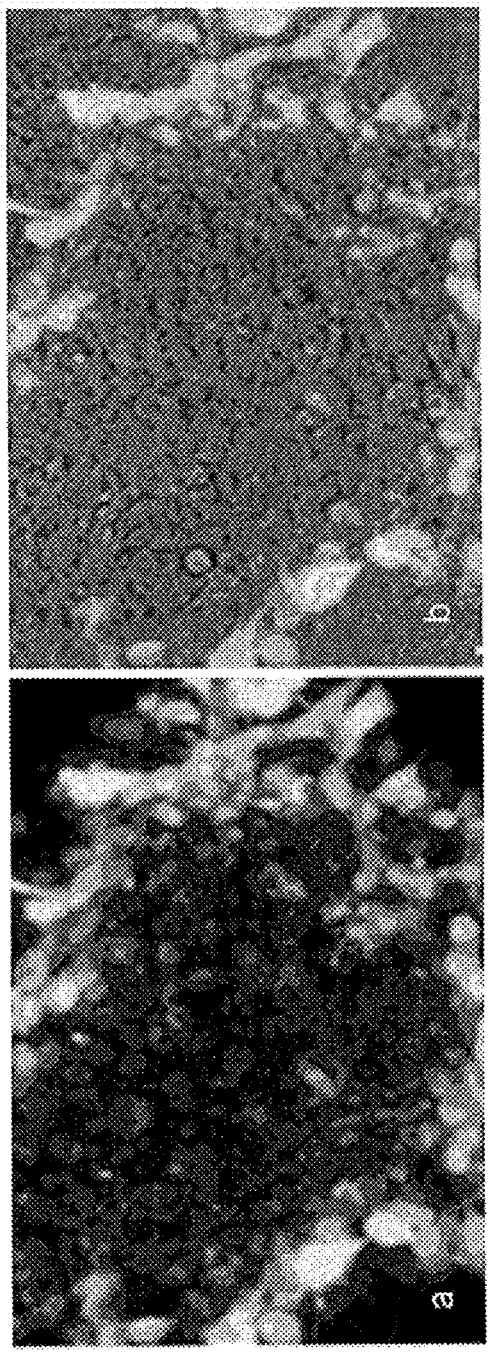
FIG. 11, Panels A-C. Staining of the biomatrix scaffold after plating hHpSCs onto the biomatrix scaffold. Live (calcein-AM, white)/Dead (ethidium bromide or EtD-Br1, light grey) assay indicates hHpSCs colonies were viable on biomatrix scaffold sections but did not take up dye in the middle of the colonies (A,B) for the first few days due to the known pumps in the stem cells (e.g., MDR1) that eliminate the vital dyes. In (B) the fluorescence image is merged with the phase one to indicate that the center of the colony contains cells. By day 7, the cells throughout the colony had differentiated and took up the vital dye in almost all the cells throughout the colony (C).
Figure 11:
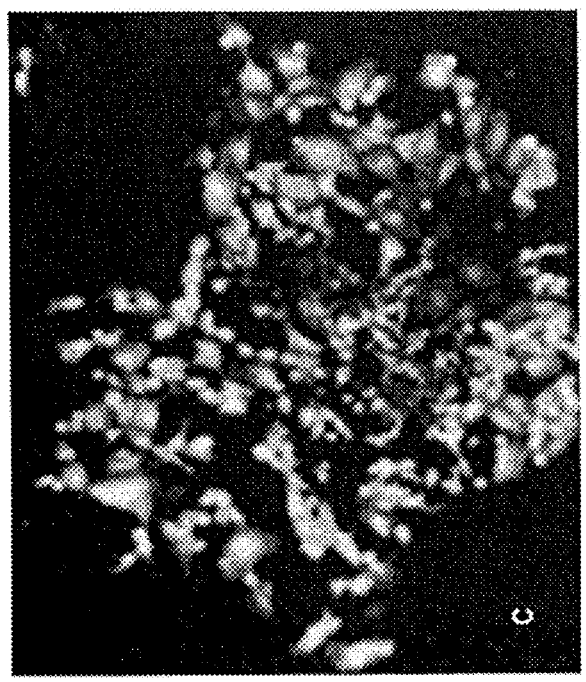

Plating hHpSCs onto dishes with sections of liver biomatrix scaffolds and in HDM tailored for adult liver cells resulted in essentially 100% of the viable cells attached within a few hours onto biomatrix scaffolds; whether intact or after cryogenic pulverization. The colonies of cells that initially formed on the sections of scaffolds retained some of their stem cell phenotype as the cells in the center of the colonies were able to resist staining with dyes (FIG. 11) and expressed classic hepatic progenitor markers, such as chemokine (C-X-C motif) receptor 4 (CXCR4) and epithelial cell adhesion molecule (EpCAM) (FIG. 5). They divided once or twice and then transitioned into cell cycle arrest and into 3-dimensional (3-D) cord-like morphologies typical for cultures of mature parenchymal cells (FIGS. 5 and 6 for stem cell differentiation; compare with FIG. 7 and FIG. 12). The HDM used did not require all the usual cytokines or growth factors, since these are present bound to the biomatrix scaffolds. The transition to growth arrest correlated with staining throughout the colonies with viability dyes (FIG. 12), with loss of expression of EpCAM and CXCR4 and with a steady increase in the expression of adult-specific hepatocytic and cholangiocytic genes such as urea and cytochrome P450 3A4. (FIG. 5).

Figure 7:
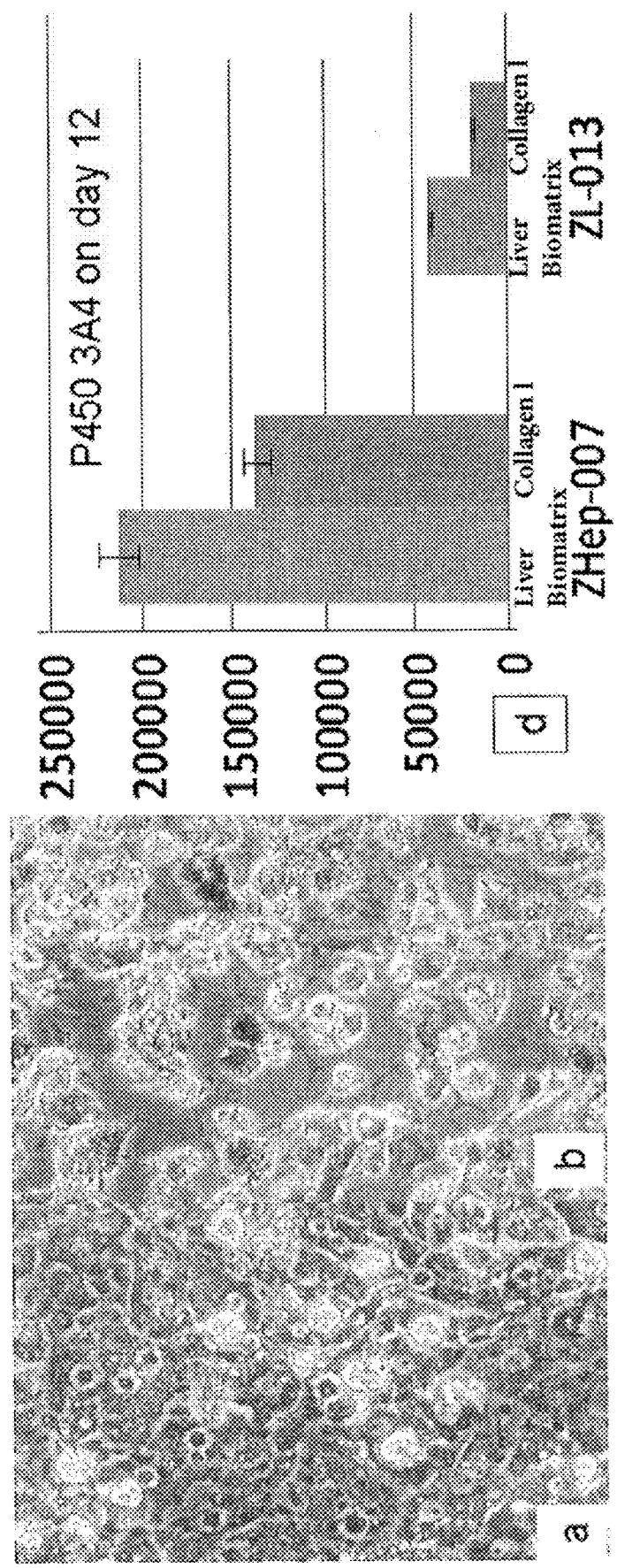
FIG. 7, Panels A-D. Stability of fully functional, mature human hepatocytes on biomatrix scaffolds. Adult human hepatocytes plated in the differentiation medium and onto type I collagen (A,B) versus on bovine liver biomatrix scaffolds (C) that were cryogenically pulverized, dispersed in medium and allowed to sediment onto the plates. Cells on type I collagen are fully viable and at their peak of differentiation from 7-12 days (A-shown at 7 days); they begin to deteriorate after 2 weeks, and by 20 days (B) they are dead, dying and non-functional. By contrast, those plated onto liver biomatrix scaffolds (C) are functional for at least 8 weeks (longer times have not been assessed yet); here is shown after 21 days in culture on pulverized liver biomatrix scaffolds. CYP450-3A4 assays on cultures of two separate preparations of cryopreserved adult human liver cells plated onto biomatrix scaffolds versus on type I collagen and assayed on day 12 (D). The sample ZHep-007 is representative of cryopreserved samples with good attachment after thawing; the sample ZL-013 is representative of those lots that have poor or no attachment after thawing. Thus, even these poorer quality samples are able to attach to biomatrix scaffolds and remain viable long term. In both samples assayed, the levels of P450s are higher when cultured on liver biomatrix scaffolds. With time on the biomatrix scaffolds, the lots of poorer quality cryopreserved cells will improve.
Figure 7:
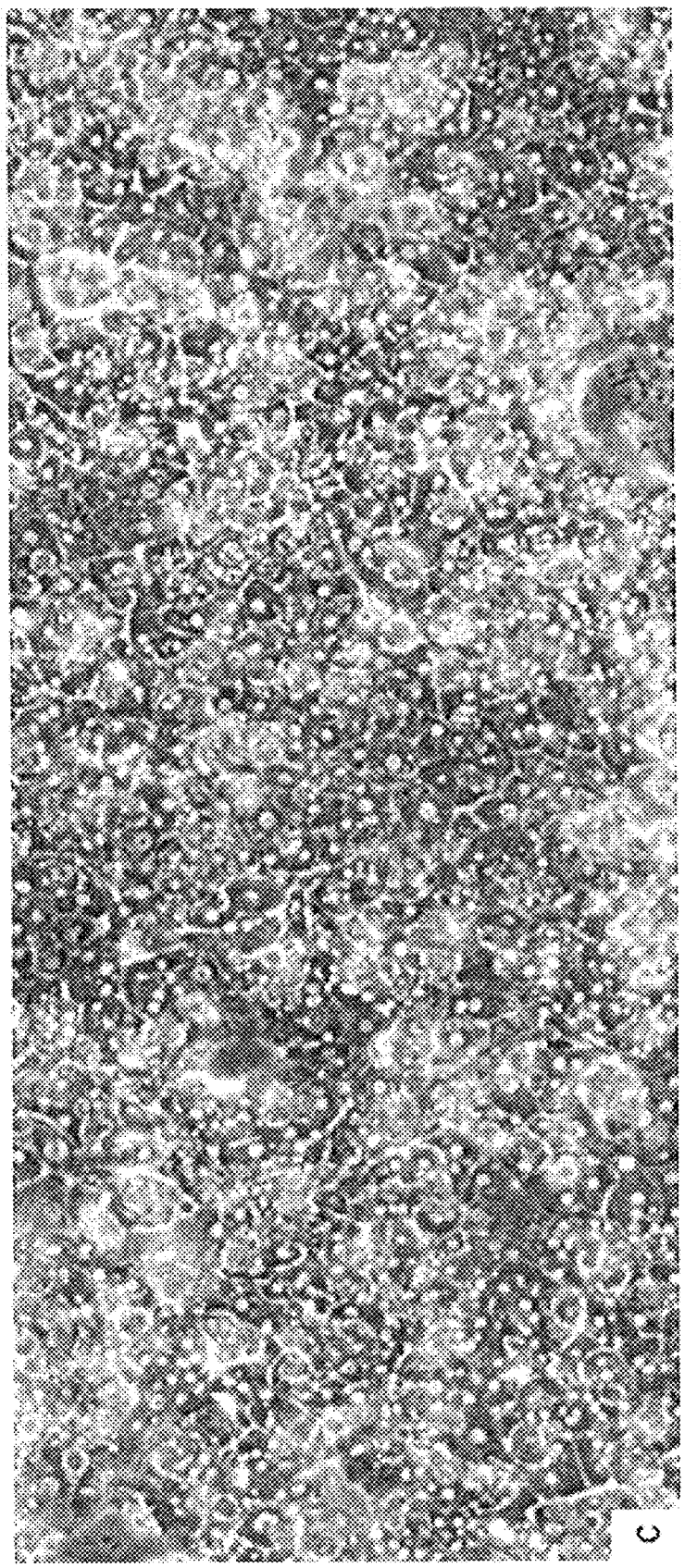
Figure 12:
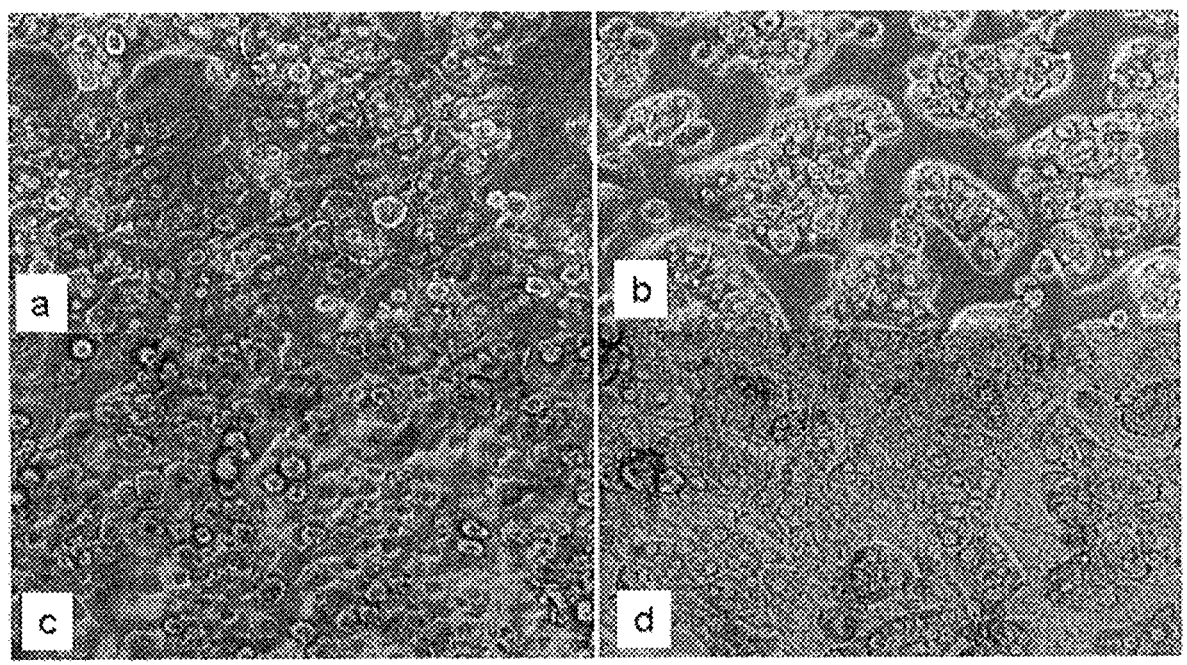
FIG. 12, Panels A-F. Comparison of rat hepatocytes cultured on type I collagen to rat hepatocytes cultured on rat liver biomatrix scaffolds. Adult rat hepatocytes cultured on type I collagen and biomatrix scaffold at day 3 (A,C) and day 10 (B,D). They attached within several minutes on liver biomatrix scaffolds and survived for as long as tested, more than 8 weeks (C,D); longer time periods were not tested. The cultures are very three-dimensional on the biomatrix scaffolds. Urea synthesis (E) and cell viability assay (F) at day 1, 3, 5, 7, 10, 14, 21 and 28, n=3.
Figure 12:
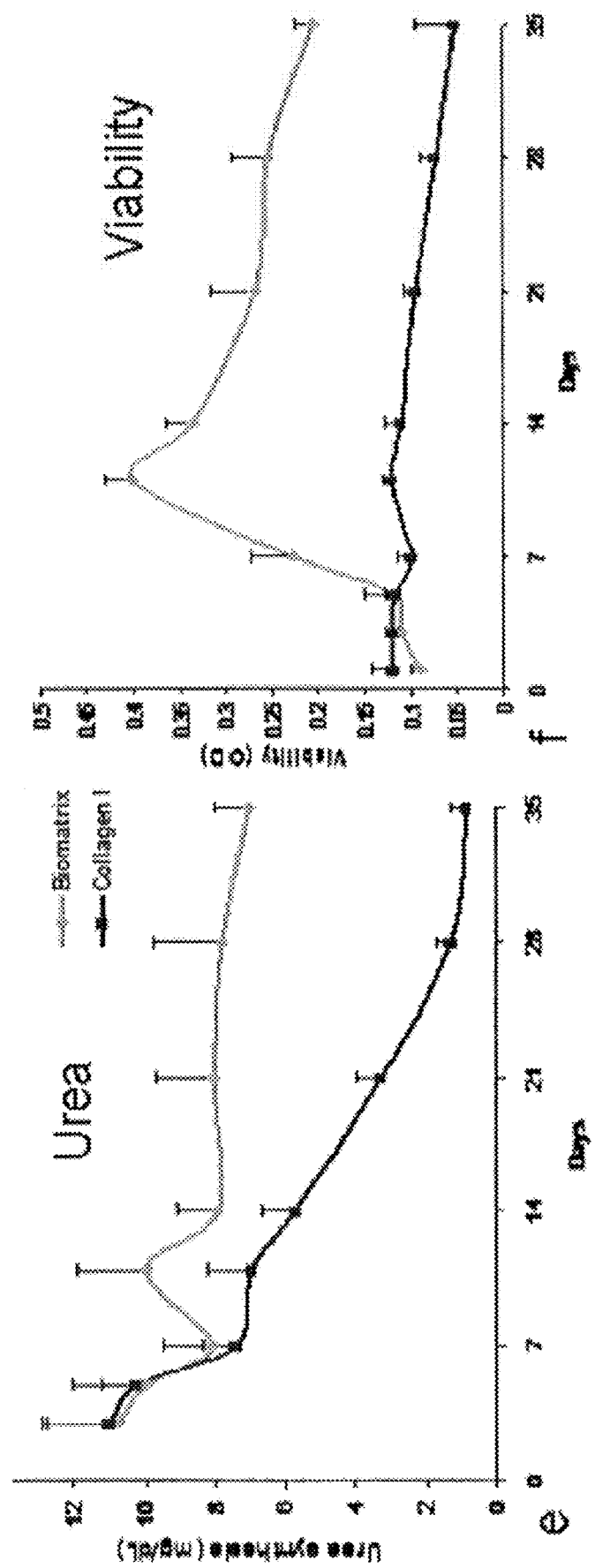
Figure 13:
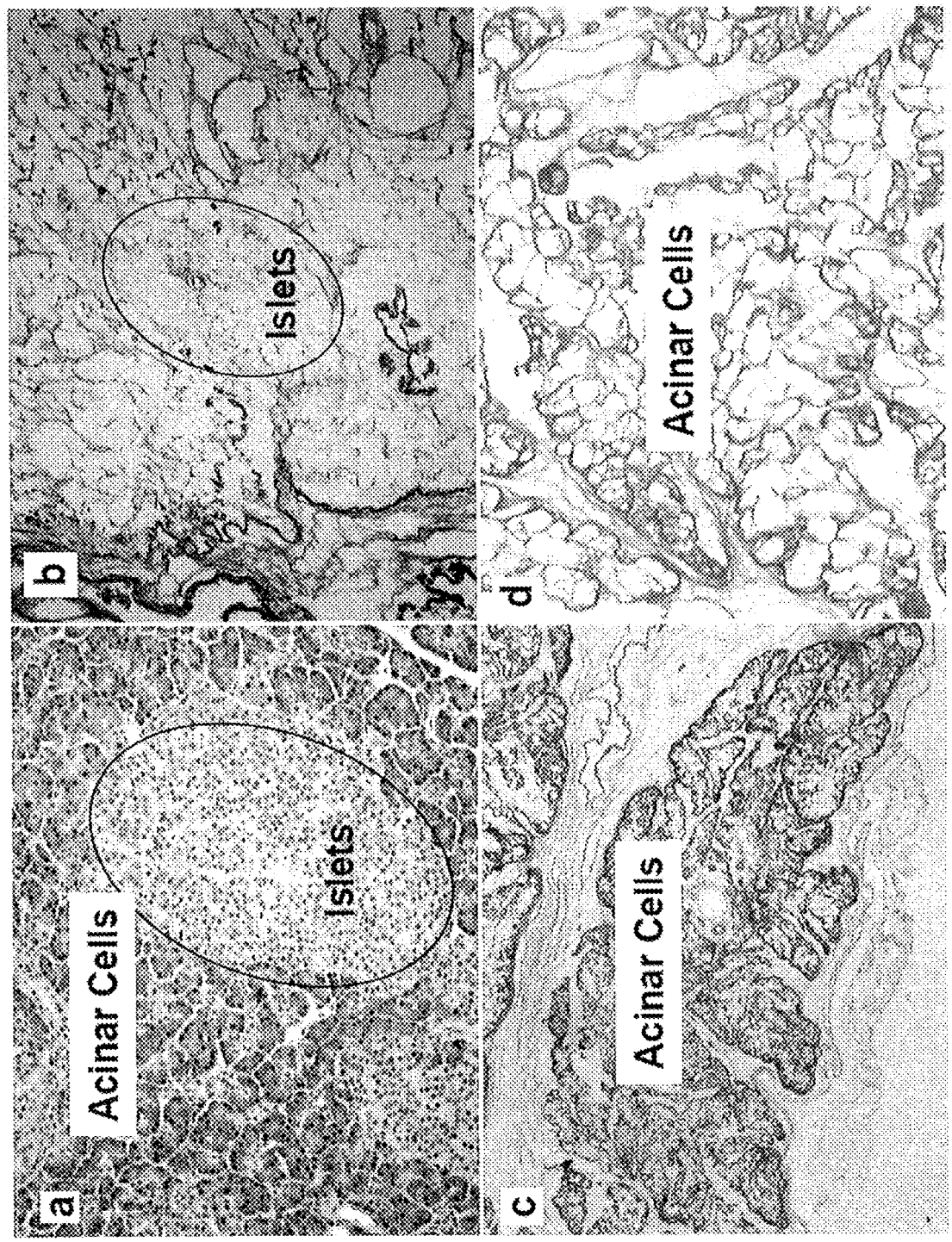
FIG. 13, Panels A-D. Comparison of a human pancreas to a human pancreatic biomatrix scaffold. Human pancreas (A) vs human pancreatic biomatrix scaffold (B-D) embedded in paraffin, sectioned and stained with Hematoxylin and Eosin (H&E). Islet structures have been outlined in B. The acinar regions of pancreatic biomatrix scaffolds are shown in C and D.
Figure 14:
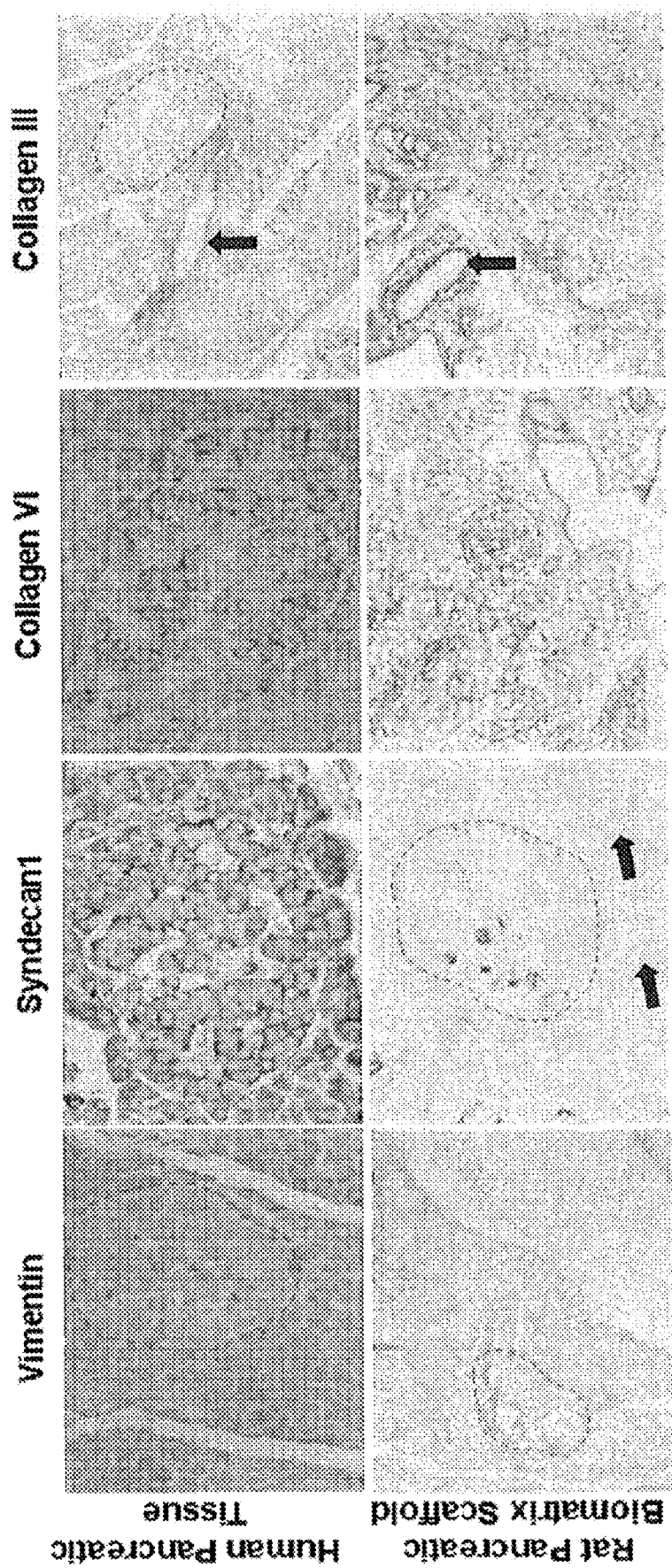
FIG. 14. Comparison of representative matrix components and one cytoskeletal component, vimentin, found in human pancreatic tissue versus rat pancreatic biomatrix scaffolds. Other cytoskeletal components (desmin, tubulin, actin) were not found in detectable amounts or were found in trace amounts (cytokeratins). The dashed lines encircle islets, note that syndecan 1 and collagen type VI are strongly positive in the islets both in pancreas tissue and in biomatrix scaffolds. Syndecan 1 is found only in the islets (dashed line) but not in the acinar cells (arrows); collagen type III is more enriched in acinar cells and around blood vessels (arrows), but not in the islets.
Figure 15:
FIG. 15, Panels A-C and COL1-HS. Histological and immunohistochemistry staining of human duodenum biomatrix scaffold. (A) Outside and lumen side of human duodenum biomatrix scaffold. The multilayer structures between the normal tissue (B) and biomatrix scaffold (C) were compared in H&E stained sections and results show scaffolds retained the villus and blood vessels in the mucosa and submucosa layers. Lower panels COL1-HS show immuohistochemistry staining of human duodenum biomatrix scaffold indicated variable amounts of extracellular matrix proteins retained in the scaffold.
Figure 15:
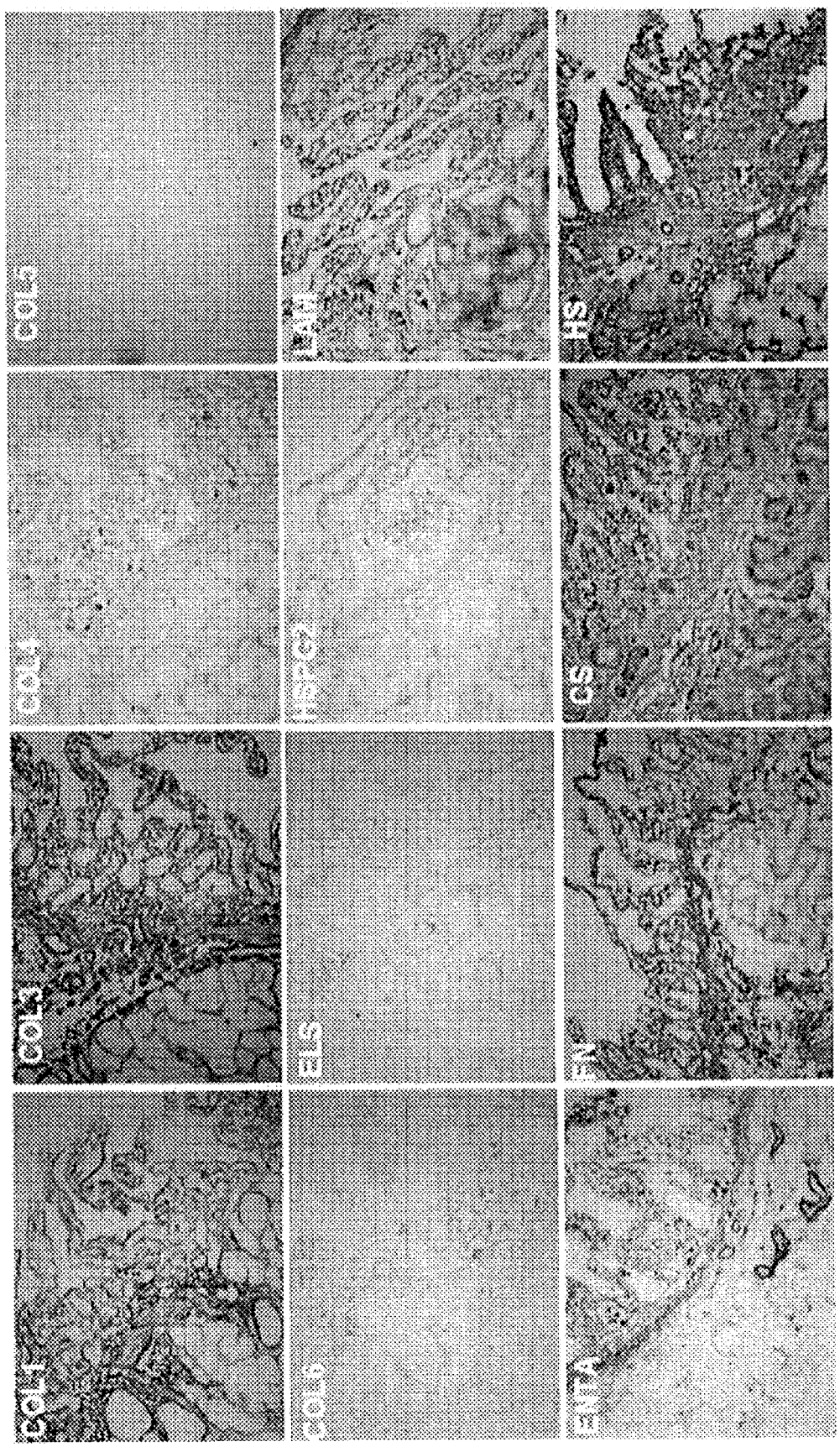
Figure 16:
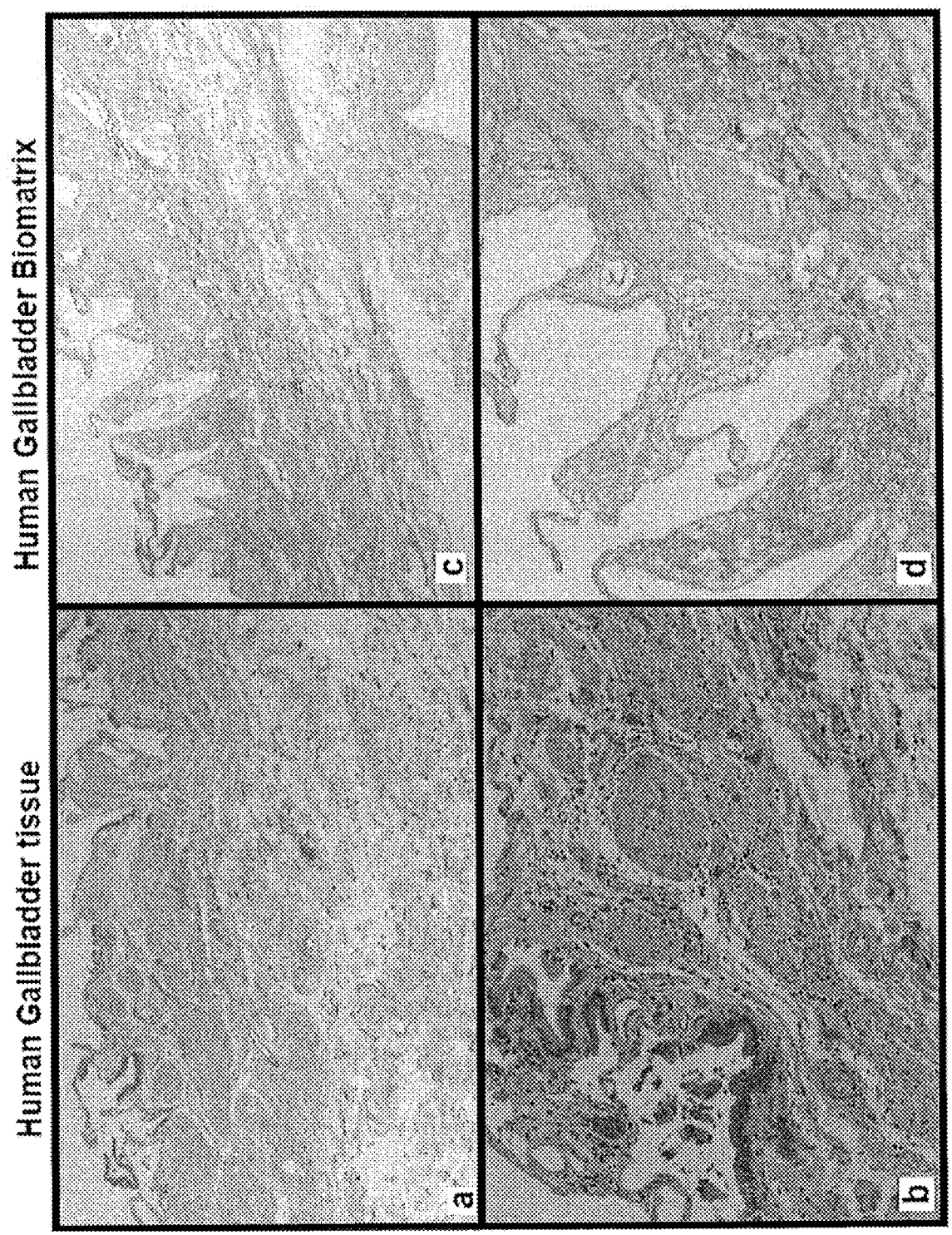
FIG. 16, Panels A-D. Comparison of a human gallbladder tissue to a human gallbladder biomatrix scaffold. Human gallbladder tissue (A,B) versus biomatrix scaffolds (C,D) prepared from it. The tissue and the biomatrix scaffolds were embedded in paraffin, sectioned and stained with hematoxylin and eosin.

Normal adult rat and adult human hepatocytes were plated onto type I collagen or on biomatrix scaffolds from rat or bovine livers and into HDM for adult cells. The adult parenchymal cells were able to attach to scaffolds within 10 minutes (even in serum-free medium) versus within hours on type I collagen, remained in growth arrest from the point of attachment; and remained viable and fully functional for more than more than 8 weeks on scaffolds versus only about 2 weeks on type I collagen. (FIGS. 7 and 12). The levels of functions of the mature liver cells on biomatrix scaffolds for weeks proved to be the same or similar to findings of others of freshly isolated, adult hepatocytes[28]. The dramatic distinctions are that the cultures on type I collagen deteriorate rapidly after 2 weeks, while those on biomatrix scaffolds remained stable morphologically and functionally for as long as the cultures were maintained (so far,._.g weeks).

Biomatrix scaffolds contain most of the tissue's extracellular matrix components and matrix-bound cytokines and growth factors providing a composite set of chemical signals that can be used as an insoluble, stable scaffolding with an extraordinary ability to induce hHpSCs to adult liver fates as well as maintain adult cells fully differentiated for weeks. In comparing the extant types of matrix extracts prepared by investigators with that of biomatrix scaffold of the present invention, it is clear that physical, enzymatic, and chemical treatments have substantial effects on the composition, mechanical behavior, and host responses to biological scaffolds derived from the decellularization of native tissues and organs, and accordingly, have important implications for their in vitro and in vivo applications. All other existing methods for preparation of substrata or scaffolds result in the removal of a large portion of the matrix components either through the use of matrix-degrading enzymes[16] or using buffers that dissolve major portions of the matrix[11]. Physical methods (e.g., snap freezing and agitation) can work to prepare matrix extracts from tissues with a layered structure such as dermis (e.g., SIS, BSM)[29] but are not useful for organs with complex tissue structures such as liver. By contrast, our method for biomatrix scaffolds resulted in loss of most cellular proteins but preserved essentially all or at least most of the collagens and collagen-associated components including the matrix-bound cytokines, hormones and growth factors.

The extracellular matrix is embedded in a mosaic lipid bilayer, which in even the simplest organism is a complex, heterogeneous and dynamic environment. The delipidation method is a critical facet of the protocol. The commonly used methods for decellularization of tissues involve ionic detergents such as SDC and sodium dodecyl sulfate (SDS). SDC is relatively milder than SDS, tends to cause less disruption to the native tissue architecture, and is less effective at solubilizing both cytoplasmic and nuclear cellular membranes[30]. There are no reports of tissue decellularization using SDC alone. Many studies have made use of a harsh non-ionic detergent (e.g., Triton X-100)[31] or zwitterionic detergents (e.g., 3-(3-cholamidopropyl) dimethylammonio]-1-propanesulfonate, CHAPS)[32]. By contrast, our method of using a combination of SDC and PLA2 dilapidated the tissue rapidly and gently.

At least twenty-nine types of collagens (I-XXIX) have been identified so far in vertebrates with functional roles in cell adhesion, differentiation, growth, tissue development and structural integrity[33,34]. The main structural components in the matrix, collagens, are known to remain insoluble in high salt concentrations and at neutral pH[35,36], a finding that is the basis of our strategy in the preparation of biomatrix scaffolds. The strategy has the added advantages that the collagens enable preservation of the matrix components bound to them, such as laminins and fibronectins (FNs), small leucine-rich proteoglycans (PGs) and GAGs that in turn preserve the cytokines, growth factors or cell surface receptors that are bound to them.

The biomatrix scaffolds are unique in their profound ability to induce rapid and consistent differentiation of stem/progenitor cells such as hHpSCs to adult fates and to maintain those lineage-restricted cells and to maintain those lineage-restricted cells or too maintain adult cells plated onto the scaffolds, as viable and fully functional cells for many weeks (>8 weeks).

Differentiation of stem cells, such as embryonic stem (ES) cells, induced pluripotent stem (iPS) cells or varying forms of mesenchymal stem cells (MSC) into fully mature liver cell types requires multiple sets of signals (soluble and matrix) presented in stages, with induction by one set required priming to respond to a different set, and can take many weeks, up to 6 weeks of culture, to generate cells having the adult liver fate[37]. Moreover, lineage restriction of MSCs to liver fates gives inconsistent results with adult cells having mixed hepatocyte and MSC phenotypes. The differentiation of ES cells, iPS cells and MSCs results in hepatocyte-like cells that express some, but never all, of the major liver-specific genes; with variability in which genes are observed; and the protein levels for those hepatic genes expressed are usually low[40] or high for one hepatic gene and negligible for others[41,42]. By contrast, the differentiation of the hHpSCs on biomatrix scaffolds resulted in essentially all of the cells expressing a classic adult phenotype and with urea, albumin and CYP450 activities at levels that are near normal after a week in culture.

The hepatocyte-like cells from any of these precursors and differentiated by protocols other than with biomatrix scaffolds, express some, but never all, of the major liver-specific genes, with variability in which genes are observed, and with the protein levels for hepatic genes being usually low or high for one hepatic gene and negligible for others. For reasons unknown, the results are different from preparation to preparation. It is expected that utilization of the biomatrix scaffolds of this invention should result in more rapid differentiation of these stem cell populations and with greater consistency in achievement of cells with a stable adult phenotype.

Differentiation of determined stem cell populations, such as hHpSCs on biomatrix scaffolds resulted in essentially all cells expressing a classic adult repertoire of genes and with urea, albumin, and CYP450 activities at near normal levels within 1 to 2 weeks in culture and with stability of that phenotype for many weeks. Thus, the biomatrix scaffolds of the present invention have the potential to greatly facilitate differentiation of determined stem cell populations to an adult liver phenotype.

The ability to differentiate stem cells on biomatrix scaffolds to achieve mature and functional cells and tissues offers considerable opportunities for academic, industrial and clinical programs enabling the use of well differentiated cell types for every type of analytical study, and, most excitingly, enabling the generation of implantable, revascularized tissues or even organs that might be used for basic research and clinical programs.

REFERENCES FOR EXAMPLE 1

1. Lanza, R. et al. *Handbook of Stem Cells*, Vol. 2 volumes. (Elsevier Academic Press, New York City; 2004).
2. Vacanti, J. P. & Langer, R. Tissue engineering: the design and fabrication of living replacement devices for surgical reconstruction and transplantation. *Lancet* 354 Suppl 1, SI32-34 (1999).
3. *Schmelzer, E. et al. Human hepatic stem cells from fetal and postnatal donors. *Journal of Experimental Medicine* 204, 1973-1987 [*co-equal first authors;**co-equal senior authors] (2007).
4. Zhang, L., Theise, N., Chua, M. & Reid, L. M. Human hepatic stem cells and hepatoblasts: Symmetry between Liver Development and Liver Regeneration. *Hepatology* 48, 1598-1607 (2008).
5. Kubota, H. & Reid, L. M. Clonogenic hepatoblasts, common precursors for hepatocytic and biliary lineages, are lacking classical major histocompatibility complex class I antigens. *Proceedings of the National Academy of Sciences of the United States of America* 97, 12132-12137 (2000).
6. Wauthier, E. et al. Hepatic stem cells and hepatoblasts: identification, isolation and ex vivo maintenance *Methods for Cell Biology* (*Methods for Stem Cells*) 86, 137-225 (2008).
7. Rhodes, J. M. & Simons, M. The extracellular matrix and blood vessel formation: not just a scaffold. *Journal of Cell and Molecular Medicine* 11, 176-205 (2007).
8. Chen, S. S., Fitsgerald, W., Zimmerberg, J., Kleinman, H. K. & Margolis, L. Cell-cell and cell-extracellular matrix interactions regulation embryonic stem cell differentiation. *Stem Cells* 25, 553-561 (2007).
9. Daley, W. P., Peters, S. B. & Larsen, M. Extracellular matrix dynamics in development and regenerative medicine. *Journal of Cell Science* 21, 255-264 (2008).
10. Chun, S. Y. et al. Identification and characterization of bioactive factors in bladder submucosa matrix. *Biomaterials* 28, 4251-4256 (2007).
11. Huber, J. E., Spievack, A., Simmons-Byrd, A., Ringel, R. L. & Badylak, S. Extracellular matrix as a scaffold for laryngeal reconstruction. *Ann Otol Rhinol Laryngol* 112, 428-433 (2003).
12. Liotta, L. A., Lee, C. W. & Morakis, D. J. New method for preparing large surfaces of intact human basement membrane for tumor invasion studies. *Cancer Letters* 11, 141-152 (1980).
13. Kleinman, H. K., McGarvey, M. L., Hassell, J. R. & Martin, G. R. Formation of a supramolecular complex is involved in the reconstitution of basement membrane components. *Biochemistry* 22, 4969-4974 (1983).
14. Vlodaysky, I., Levi, A., Lax, I., Fuks, Z. & Schlessinger, J. Induction of cell attachment and morphological differentiation in a pheochromocytoma cell line and embryonal sensory cells by the extracellular matrix. *Developmental Biology* (*Orlando*) 93, 285-300 (1982).
15. Gospodarowicz, D., Delgado, D. & Vlodaysky, I. Permissive effect of the extracellular matrix on cell proliferation in vitro. *Proceedings of the National Academy of Sciences of the United States of America* 77, 4094-4098 (1980).
16. Badylak, S. F. The extracellular matrix as a scaffold for tissue reconstruction. *Semin Cell Dev Biol* 13, 377-383 (2002).
17. Gilbert, T. W. et al. Collagen fiber alignment and biaxial mechanical behavior of porcine urinary bladder-derived extracellular matrix. *Biomaterials* 16 (2008).
18. Lee, M., Chang, P. C. & Dunn, J. C. Evaluation of small intestinal submucosa as scaffolds for intestinal tissue engineering. *Journal of Surgical Research* 147, 168-171 (2008).
19. Martin, N. D. et al. In vivo behavior of decellularized vein allografts. *Journal of Surgical Research* 129, 17-23 (2005).

20. Ott, H. C. et al. Perfusion-decellularize matrix using nature's platform to engineer a bioartificial heart. *Nature Medicine* 14, 213-221 (2008).
21. Macchianni, P. et al. Clinical transplantation of a tissue-engineered airway. *Lancet* 372, 2023-2030 (2008).
22. Franklin, M. E., Jr. et al. The use of porcine small intestinal submucosa as a prosthetic material for laparoscopic hernia repair in infected and potentially contaminated fields: long-term follow-up. *Surgical Endoscopy* 22, 1941-1946 (2008).
23. Miller, E. J. & Rhodes, R. K. Preparation and characterization of the different types of collagen. *Methods in Enzymology* 82, Part A, 33-64 (1982).
24. Yayon, A., Klagsbrun, M., Esko, J. D., Leder, P. & Ornitz, D. M. Cell surface, heparin-like molecules are required for binding of basic fibroblast growth factor to its high affinity receptor. *Cell Molecular Life Science* 64, 841-848 (1991).
25. Yamuchi, M. & Shiba, M. Lysine hydroxylation and cross-linking of collagen. *Methods in Molecular Biology* 446, 95-108 (2008).
26. Liu, Y., Cai, S., Shu, X. Z., Shelby, J. & Prestwich, G. D. Release of basic fibroblast growth factor from a crosslinked glycosaminoglycan hydrogel promotes wound healing. *Wound Repair Regen* 15, 245-251 (2007).
27. Martinez-Hernandez, A., Delgado, F. M. & Amenta, P. S. The extracellular matrix in hepatic regeneration. Localization of collagen types I, III, IV, laminin, and fibronectin [published erratum appears in Lab Invest 1991 August; 65(2):257]. *Laboratory Investigation* 64, 157-166 (1991).
28. LeCluyse, E. L. Human hepatocyte culture systems for the in vitro evaluation of cytochrome P450 expression and regulation. *Eur J Pharm Sci* 13, 343-368. (2001).
29. Brown, B., Lindberg, K., Reing, J., Stolz, D. B. & Badylak, S. F. The basement membrane component of biologic scaffolds derived from extracellular matrix. *Tissue Engineering* 12, 519-526 (2006).
30. Seddon, A. M., Curnow, P. & Booth, P. J. Membrane proteins, lipids and detergents, not just a soap opera. *Biochimica Biophysica Acta* 1666, 105-117 (2004).
31. Ozeki, M. et al. Evaluation of decellularized esophagus as a scaffold for cultured esophageal epithelial cells. *Journal of Biomedical Materials. Research A* 19, 771-778 (2006).
32. Rieder, E. et al. Decellularization protocols of porcine heart valves differ importantly in efficiency of cell removal and susceptibility of the matrix to decellularization with human vascular cells. *Journal a/Thoracic Cardiovascular Surgery* 127, 399-405 (2004).
33. Olsen, B. R. & Ninorniya, Y. Collagens: Guidebook to the Extracellular Matrix and Adhesion Proteins. (Oxford University Press, Oxford; 1993).
34. Yurchenco, P. D. & O'Rear, J. J. Basement membrane assembly. *Methods Enzymol* 245, 489-518 (1994).
35. Seyer, J. M., Hutcheson, E. T. & Kang, A. H. Collagen polymorphism in normal and cirrhotic human liver. *J Clin Invest* 59, 241-248 (1977).
36. Traub, W. & Piez, K. A. The chemistry and structure of collagen. *Advances in Protein Chemistry* 25, 243-352 (1971).
37. D'Amour, K. A. et al. Production of pancreatic hormone-expressing endocrine cells from human embryonic stem cells. *Nature Biotechnology* 24, 1392-1401 (2006).
38. Pittenger, M. F. et al. Multilineage potential of adult human mesenchymal stem cells. *Science* 284, 143-147. (1999).
39. Kazemnejad, S. et al. Biochemical and molecular characterization of hepatocyte-like cells derived from human bone marrow mesenchymal stem cells on a novel three-dimensional biocompatible nanofibrous scaffold. *Journal of Gastroenterology and Hepatology* 24, 278-287 (2009).
40. Lysy, P. A., Smets, F., Najimi, M. & Sokal, E. M. Leukemia inhibitory factor contributes to hepatocyte-like differentiation of human bone marrow mesenchymal stem cells. *Differentiation* 76, 1057-1067 (2008).
41. Campard, D., Lysy, P. A., Najimi, M. & Sokal, E. M. Native Umbilical Cord Matrix Stem Cells Express Hepatic Markers and Differentiate Into Hepatocyte-like Cells. *Gastroenterology* 134, 833-848 (2008).
42. Song, Z. et al. Efficient generation of hepatocyte-like cells from human induced pluripotent stem cells. *Cell Research*, In press. Epub on Sep. 8 (2009).
43. Hayes, A., Tudor, D., Nowell, M., Caterson, B. & Hughes, C. Unique forms of chondroitin sulfate proteoglycans in stem cell niches. *Journal of Histochemistry and Cytochemistry* 56, 125-138. (2007).
44. Couvelard, A. et al. Expression of integrins during liver organogenesis in humans. *Hepatology* 27, 839-847 (1998).
45. Lyon, M., Deakin, J. A. & Gallagher, J. T. Liver heparan sulfate structure. A novel molecular design. *Journal of Biological Chemistry* 269, 11208-11215 (1994).
46. Vongchan, P. et al. Structural characterization of human liver heparan sulfate. *Biochim Biophys Acta* 1721, 1-8 (2005).
47. Wauthier, E. et al. Hepatic stem cells and hepatoblasts: identification, isolation and ex vivo maintenance *Methods for Cell Biology (Methodsfor Stem Cells)* 86, 137-225 (2008).
48. Kubota, H. & Reid, L. M. Clonogenic hepatoblasts, common precursors for hepatocytic and biliary lineages, are lacking classical major histocompatibility complex class I antigens. *Proceedings of the National Academy of Sciences of the United States of America* 97, 12132-12137 (2000).
49. *Schmelzer, E. et al. Human hepatic stem cells from fetal and postnatal donors. *Journal of Experimental Medicine* 204, 1973-1987 [*co-equal first authors;* *co-equal senior authors] (2007).
50. Schmelzer, E., Wauthier, E. & Reid, L. M. Phenotypes of pluripotent human hepatic progenitors. *Stem Cell* 24, 1852-1858 (2006).
51. Yamauchi, M. & Shiiba, M. Lysine hydroxylation and cross-linking of collagen. *Methods Molecular Biology* 446, 95-108 (2008).
52. Gilbert et al. Quantification of DNA in biologic scaffold materials. *Journal of Surgical Research* 152:135-139 (2009).

Example 2. Methods for Industrial Scale Dispersal of Biomatrix Scaffolds

Additional methods for dispersing the biomatrix scaffolds onto dishes after pulverization were developed at GigaCyte, LLC (Branford, Conn.). They can be used with biomatrix scaffolds from any tissue including large mammals (e.g., human, porcine and bovine tissues, etc.). Pig and bovine tissues were obtained from a USDA certified meat processing facility, were transported in RPMI 1640). This medium can be any medium with a composition that mimics the constituents of interstitial fluid and with an osmolality that is in the range of 250-350 mOsm/Kg. The tissues are then processed as described herein to generate biomatrix scaffolds.

These methods include further processing of biomatrix scaffolds for reduction to μm sized particles in suspension for coating plates using automation. In one nonlimiting example, the process includes homogenization of the biomatrix scaffold in high salt solution to ensure collagens remain insoluble. A modified delipidating buffer comprised of 36 units/L phospholipase A2 plus 1% sodium deoxycholate and 0.1 mg/ml soybean trypsin inhibitor is added at a ratio of 1:1 buffer:homogenate, which results in the buoyant rise of biomatrix material to the top where it is collected for further processing. The biomatrix material is further processed for removal of the delipidating buffer and washed with nuclease solution to remove nucleases: 5 mg/100 ml RNase, 1 mg/100 ml DNase and 0.1 mg/ml soybean trypsin inhibitor. The biomatrix material is then further processed in high salt (>3.4M NaCl) buffer to ensure removal of all residues, to keep the collagens insoluble and also to minimize protease activity. The biomatrix material is further processed to remove the high concentration of salt to prepare for particle size reduction by washing the biomatrix material in basal medium that contains antimicrobic/antimycotics, gentamicin and HEPES buffer. The biomatrix material is then further processed to reduce the particle size of the biomatrix material to μm sized particles (range 1-100 μm) in suspension, at any dilution, optimally at 1:6, in basal medium that contains antimicrobic/antimycotics, gentamicin and HEPES buffer, frozen at −80° C. and then pulverized by cryogenic grinding. If the biomatrix isn't diluted prior to grinding the matrix is too clumpy for coating plates evenly. This is a key step to allow for grinding and even coating of plates. The biomatrix particles can be in suspension at any dilution but optimally 1:6. The biomatrix particles are thawed and coated onto plates used for differentiation of stem cells. The biomatrix particles can be further diluted to any dilution, optimally 1:24 in basal medium that contains antimicrobic/antimycotics, gentamicin and HEPES buffer and coated onto plates used for long term maintenance of primary freshly isolated, cryopreserved or stem cell-derived terminally differentiated cell types or for differentiating any stem cell source into hepatocytes. Sterilization of the biomatrix coated plates can be done with, e.g., gamma irradiation (5,000 rads) and stored at 4° C. (or frozen at −80° C.) until use. Plating cells onto the biomatrix does not require serum containing medium for attachment but serum-containing medium can be used for applying cells to the biomatrix. The composition of biomatrix particles from any tissue can be used for coating plates and other apparati.

As another example, the present invention provides a method of producing a biomatrix scaffold from biological tissue for industrial scale dispersal onto culture apparatus, comprising: a) producing a biomatrix scaffold according to any of the methods of this invention as described herein, b) diluting the biomatrix scaffold of (a) in basal medium; c) freezing the biomatrix scaffold of (b) at about −80° C.; d) pulverizing the biomatrix scaffold of (c) by cryogenic grinding into biomatrix particles ranging in size from about 1 μm to about 100 μm (e.g., about 1 μm, 2 μm, 5 μm, 10 μm, 15 μm, 20 μm, 25 μm, 30 μm, 40 μm, 50 μm, 60 μm, 70 μm, 80 μm, 90 μm, 95 μm 100 μm, 110 μm, 120 μm, 150 μm, 200 μm, etc.); e) thawing the biomatrix particles of (d) in suspension in basal medium; and f) dispersing the biomatrix particles of step (e) onto a culture apparatus, thereby producing a biomatrix scaffold from biological tissue for industrial scale dispersal onto culture apparatus. In some embodiments, this method can further comprise the step of sterilizing the biomatrix particles, which can be carried out, for example by gamma irradiation.

In some embodiments of the methods described above, the biomatrix scaffold of step (b) can be diluted at about a 1:6 ratio (e.g., 1:3, 1:4, 1:5, 1:6, 1:7, 1:8, 1:9, etc.) in basal medium. In some embodiments, the biomatrix particles of step (e) can be diluted at about a 1:24 (e.g., 1:15, 1:16, 1:17, 1:18, 1:19, 1:20, 1:21, 1:22, 1:23, 1:24, 1:25, 1:26, 1:27: 1:28, 1:29, 1:30, etc) in basal medium.

Outline of Exemplary Protocol Used for Adult Liver

1000× Soybean Trypsin Inhibitor
   Final concentration 0.1 mg/ml
Tissue Transport Solution
   Basal medium such as RPMI 1640 or phosphate buffered saline with calcium and magnesium
   Antibiotic/Antimycotic 1 OO× solution (Gibco #15240-112) Gentamicin (25 ug/ml) (Gibco #15710-072)
Solution 1: Tissue Blending Solution
   3.4M NaCl.
   0.1 mg/ml Soybean Trypsin Inhibitor (Gibco #17075-029)
Solution 2: Delipidation Solution
   A mix of Solution 1 with 1:1 PBS (w/Ca & Mg); alternative ratios being 1:2, 1:3, 1:4) or alternatively a basal medium such as RPMI 1640
   0.1% Sodium Deoxycholate (Sigma D6750-100 g)
   36 u/L Phospholipase A2 (Sigma P9279-25 mg)
   0.1 mg/ml Soybean Trypsin Inhibitor (Gibco #17075-029)
Solution 3: Nuclease Solution
   Basal medium such as RPMI 1640
   5 mg/100 ml RNase (Sigma R6513-1 g)
   1 mg/100 ml DNase (DN25-1 g)
   0.1 mg/ml Soybean Trypsin Inhibitor
Solution 4: High Salt Solution
   3. M NaCl.
Solution 5: Salt Removal & Grinding Solution
   William's E
   Antibiotic/Antimycotic (100×)
   Gentamicin (30 ug/ml)
Steps in Biomatrix Isolation Process for Large Organs
1. Tissue homogenization in high salt
2. Decellularization and Delipidation
3. Nuclease Removal
4. High Salt Wash
5. Salt Removal
6. Biomatrix Particle Size Reduction
7. Coating Plates With Biomatrix Biomatrix Isolation Process 1.0 Tissue Procurement
   1.1 Obtain organ tissue from a USDA certified and inspected facility
   1.2 Transport organ tissue from USDA facility to Giga-Cyte laboratory in plastic container in Tissue Transport Solution
   1.3 Prepare tissue for perfusion or homogenization
      1.3.1 Homogenization is preferred for in vitro application in multi-well plates
2.0 Tissue Homogenization
   2.1 Aseptically, cut tissue into small pieces (3×3 cm) with surgical blade No. 22 and place in Tissue Transport solution to remove blood 2.2 Rinse tissue pieces 3-4 times in Tissue Transport Solution to remove as much blood as possible 2.3 Homogenize 400 g tissue in equal volume of Solution 1 until mixture is homogeneous (3-5 min.)

2.4 Pour homogenized tissue solution into 2 L roller bottle for decellularization 2.5 Repeat for entire batch of tissue pieces 3.0 Decellularization and Delipidation 3.1 Add equal volume of Solution 2 to homogenized tissue in roller bottle 3.2 Mix well by inverting bottle several times then let set for 15-30 minutes 3.3 The buoyant matrix material will rise to the top creating a distinct separation of light matrix material atop of the liver colored solution 3.4 Pipette off the buoyant matrix material and transfer into another roller bottle 3.5 Pool matrix from multiple homogenizations 3.6 Transfer 375 ml matrix material into a 750 ml centrifuge bottle, add equal volume of Solution 2 to each bottle and shake vigorously for 1 minute to ensure complete decellularization and delipidation 3.7 Pellet by centrifugation at high (3750 RPM) speed for 10 minutes, then remove supernatant 3.8 Repeat this process 1 more times (2 times total)

4.0 Nuclease Removal 4.1 Remove supernatant after final decellularization wash, taking care not to disturb the biomatrix pellet 4.2 Add equal volume of Solution 3 to each bottle and shake vigorously for 1 min. to ensure all material is in suspension and complete removal of nucleases 4.3 Pellet by centrifugation at high (3750 RPM) speed for 10 minutes, then remove supernatant 4.4 Repeat this process 1 more times. (2 times total)

5.0 High Salt Wash 5.1 Remove supernatant after final nuclease wash, taking care not to disturb the biomatrix pellet 5.2 Add equal volume of Solution 4 to each bottle and shake vigorously taking care to ensure all material is in suspension 5.3 Pellet by centrifugation at high (3750 RPM) speed for 10 minutes, then remove supernatant 5.3.1 At this phase biomatrix doesn't pellet well and is buoyant after centrifugation.

5.3.2 Pipette supernatant off and run through nylon filter to collect buoyant material 5.3.3 Return buoyant matrix collected to the centrifuge bottle 5.4 Repeat this process at least 2 times before stopping 5.4.1 Supernatant is slightly tan to clear in color after final salt wash 5.5 After 2° d high salt wash is a good stopping point if it is late in the day.

5.6 Pour the contents of all centrifuge bottles into one roller bottle and top off with Solution 4 then put biomatrix into 4° C. over night.

5.7 Next day continue remaining salt washes 5.8 Shake biomatrix bottle vigorously to mix well biomatrix material then transfer biomatrix into the centrifuge bottles and continue 3-4 more salt washes 5.9 Condense biomatrix into as few bottles as possible filling each a maximum of half full to allow for Salt washes 6.0 Salt Removal 6.1 Remove supernatant after final salt wash taking care not to disturb the biomatrix pellet 6.2 Add equal volume of Solution 5 and shake vigorously to ensure all biomatrix material is in suspension 6.3 Pellet by centrifugation at high (3750 RPM) speed for 10 minutes 6.4 Remove supernatant and add equal volume of Solution 5 then shake vigorously.

6.5 Repeat 2 times (3 times total) to ensure supernatant is clear 6.5.1 Biomatrix will pellet more tightly with each spin 6.5.2 Supernatant should be clear without any color following final wash 6.6 After final Solution 5 wash record volume of matrix pellets from each bottle 6.7 Transfer and pool all biomatrix pellets into new roller bottle 6.8 Measure volume of biomatrix material 6.9 Dilute the pooled biomatrix 1:6 with Solution 5

6.9.1 Calculate amount of Solution 5 required 6.9.1.1. Example: 200 ml biomatrix×6=1,200

6.9.1.2. Add 1 L Solution 5 to 200 ml biomatrix for a 1:6 biomatrix suspension 6.10 Aliquot 30 ml biomatrix 1:6 suspension into pre-labeled freezer bags 6.11 Freeze bags of biomatrix at −80° C. and store until grinding 6.12 Prepare "biomatrix lot grinding data sheet" for the new biomatrix lot 6.12.1.1. Record the number of bags produced from this new batch 6.12.1.2. Each bag is a separate grind from the same lot 6.13 The biomatrix material produced from this batch is considered one lot 6.14 Assign lot number to the batch 7.0 Biomatrix Particle Size Reduction 7.1 Prepare the grinding mill (Spex Sample Prep 6870) with LN2 and chill grinding chamber 7.2 Remove frozen biomatrix bag from freezer 7.3 Break into small pieces 7.4 Transfer frozen biomatrix pieces into pre-chilled grinding mill chamber 7.5 Grind 2 runs (one run is 12×2 minute grinds each followed by 2 minute cool down) 48 minutes each in cryomill 7.6 Transfer ground biomatrix into 100 ml bottle pre-labeled with lot number and bag number (bag number identifies grind date)

7.7 Keep frozen at −80° C. until ready for coating plates 8.0 Preparing Biomatrix for Coating Plates 8.1 Thaw one bottle of biomatrix rapid thaw method in 37° C. water-bath 8.2 Measure thawed biomatrix suspension (should be 30 ml±2 ml)

Figure 17:
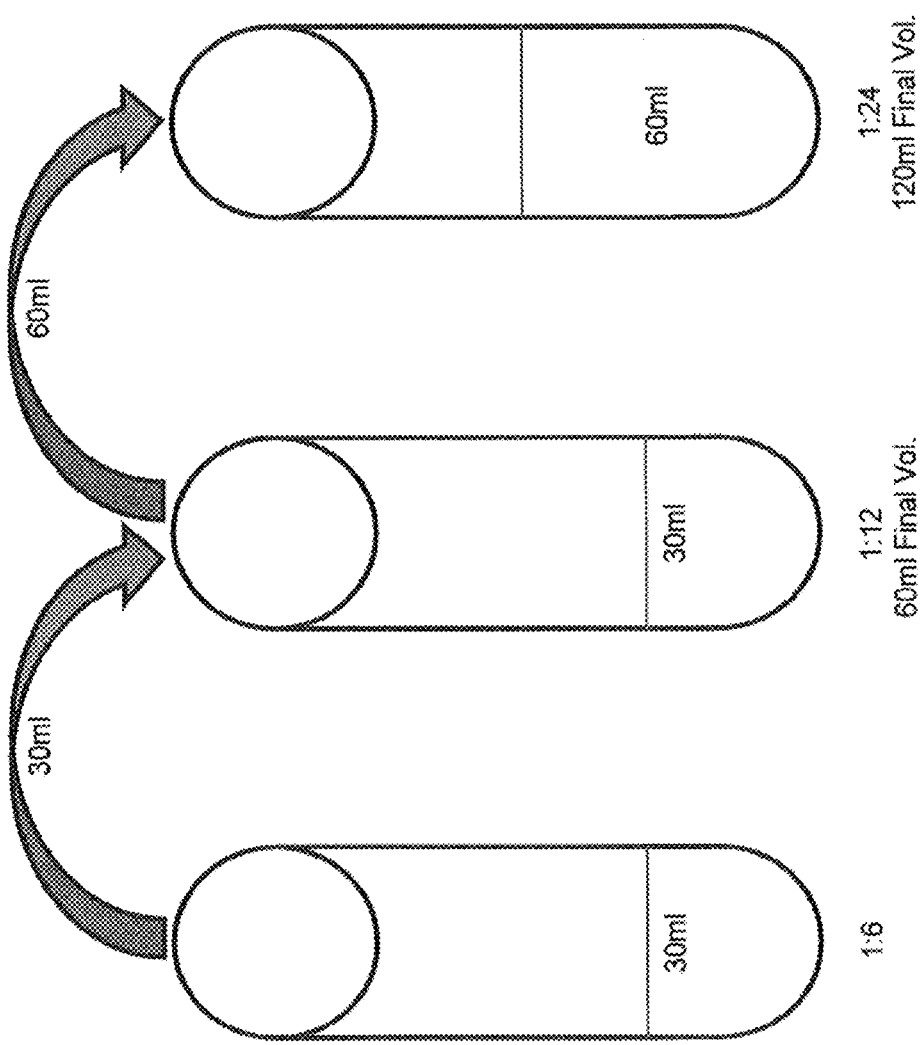
FIG. 17. Example of preparation of biomatrix solution for 1:24 dilution. 30 ml×3=90 ml. 30 ml biomatrix+90 ml Solution 5=120 ml biomatrix solution for 1:24 dilution.

8.3 Dilute to 1:24 with Solution 5 (see FIG. 17)

8.3.1 Calculate volume of Solution 5 to add to the 1:6 biomatrix suspension 8.3.1.1. Multiply biomatrix suspension volume×3

8.3.1.2. Add that volume to the 1:6 suspension for 1:24 dilution 8.4 8.4 Coat plates immediately (letting diluted biomatrix set will result in clumping)

9.0 Coating Plates with Biomatrix 9.1 Determine the number of plates to be coated. Refer to Table 8 for plating volumes 9.1.1 Remove plates from packaging aseptically and organize in the laminar flow hood 9.1.2 Transfer appropriate volume of biomatrix suspension into each well using a multichannel pipettor where appropriate. Refer to Table 1 for plating volume
9.1.3 Ensure that the suspension is evenly distributed across well-tap plate if necessary but don't remove from flat surface of hood.
9.1.4 Let plates remain undisturbed overnight
9.1.5 First thing the next day remove solution from each well
   9.1.5.1. Handle plates carefully so matrix coating isn't disturbed
   9.1.5.2. Tilt plate toward you without removing plate edge from hood surface. This stabilizes plate to prevent jerky movements that will make biomatrix come off the plate
   9.1.5.3. Using suction apparatus with fine tip pipette aspirate entire solution from each well. DO NOT TOUCH MATRIX SURFACE WITH PIPETTE!!!
   9.1.5.4. Gently lay plate back down, remove lid and allow to dry completely (2 hours)
   9.1.5.5. Moving plate while wet disturbs the biomatrix coating
   9.1.5.6. Do not move plates until matrix is dry
   9.1.5.7. When completely dry replace lid and examine for quality
   9.1.5.8. Place plates that have smooth coating into plate pouch
   9.1.5.9. Seal pouch and apply label
   9.1.5.10. Sterilize by gamma irradiation (5,000 rads)
   9.1.5.11. Store coated plates in 4° C.
   9.1.5.12. Ship coated plates in packs of 5 on ice pack
10.0 Using Biomatrix Plates
10.1 Remove plate from packaging aseptically and place in biological safety cabinet
10.2 Add media to each well and place in incubator for at least 2 hours prior to use
10.3 When ready to plate cells, remove rehydration media and wash with tissue culture media once
10.4 Add cells The foregoing is illustrative of the present invention, and is not to be construed as limiting thereof. The invention is defined by the following claims, with equivalents of the claims to be included therein. All publications, patent applications, patents, patent publications, sequences identified by GenBank® Database and/or SNP accession numbers, and other references cited herein are incorporated by reference in their entireties for the teachings relevant to the sentence and/or paragraph in which the reference is presented.

TABLE 1

Molar concentration ranges of NaCl. for Collagen Types 1-V.

| Collagen Type | Source | Molar Concentration range of NaCl. for precipitation (therefore, insolubility at the concentration specified and/or at concentrations above that listed) | |
|---|---|---|---|
| | | Acidic pH | Neutral pH |
| I | Skin | 0.7-0.9 | 2.6 |
| I Trimer | Skin | 0.7-0.9 | 4.0 |
| III | Skin | 0.7-.09 | 1.5-1.7 |
| IV | Placenta | 1.2 | 1.7-2.0 |
| V | Amnion and chorion; placenta | 1.2 | 3.6-4.5 |

Reference:
Paul Bornstein and Helene Sage (1980) Structurally Distinct Collagen Types. *Annual Review of Biochemistry*. 49: 957-1003.

These data are representative of conditions for insolubility of types of collagens. One has to identify the collagen types within a tissue and then use the highest salt concentration identified for those collagens in the tissue and as that for the buffers used for preparing the biomatrix scaffolds. For example, for skin, one would use a buffer at neutral pH and with a salt concentration of 4.0M, a salt concentration that would keep insoluble type I and III collagens. By contrast, for placenta, one would use a buffer at neutral pH and 4.5M salt to keep insoluble both type IV and type V collagen.

The types of collagens present in a tissue are distinct at different ages of a host. For example, fetal livers have high levels of type III, IV and V collagens (requiring salt concentrations above 4.0M), whereas adult livers have a mix of type I, III, IV, V, VI and XVIII collagens (requiring lower salt concentrations). Thus, the salt concentration needed for a biomatrix scaffold preparation is dictated by the repertoire of collagens that are dominant in the tissue. See reference 23 of Example 1 for further details.

TABLE 2

Analyses of Collagen Content in Liver Biomatrix Scaffold

| | BIOMATRIX SCAFFOLDS (N = 4) | | | | | | LIVER TISSUE (N = 3) | | | | |
|---|---|---|---|---|---|---|---|---|---|---|---|
| Amino acids | Sample 1 Res/ 1000 | Sample 2 Res/ 1000 | Sample 3 Res/ 1000 | Sample 4 Res/ 1000 | AVER- AGE Res/ 1000 | SD Res/ 1000 | Sample 1 Res/ 1000 | Sample 2 Res/ 1000 | Sample 3 Res/ 1000 | AVER- AGE Res/ 1000 | SD Res/ 1000 |
| Hyp | 10.0 | 13.8 | 15.3 | 12.1 | 12.8 | 2.3 | 0.0* | 0.0* | 0.0* | 0.0* | 0.0* |
| Asp | .82.7 | 77.1 | 78.4 | 85.5 | 80.9 | 3.9 | 93.0 | 94.5 | 90.8 | 92.8 | 1.8 |
| Thr | 52.6 | 51.1 | 45.6 | 52.4 | 50.4 | 3.3 | 52.2 | 51.0 | 53.7 | 52.3 | 1.3 |
| Ser | 56.5 | 53.7 | 61.9 | 62.4 | 58.6 | 4.2 | 57.7 | 57.0 | 62.0 | 58.9 | 2.7 |
| Glu | 112.0 | 107.0 | 117.4 | 118.1 | 113.6 | 5.2 | 123.9 | 122.0 | 130.1 | 125.4 | 4.2 |
| Pro | 52.3 | 52.2 | 55.7 | 51.6 | 52.9 | 1.9 | 46.6 | 45.9 | 46.4 | 46.3 | 0.4 |
| Gly | 118.7 | 134.0 | 125.4 | 109.4 | 121.9 | 10.4 | 88.2 | 84.6 | 89.1 | 87.3 | 2.4 |
| Ala | 88.3 | 86.1 | 89.5 | 83.6 | 86.9 | 2.6 | 79.0 | 78.2 | 90.6 | 82.6 | 7.0 |
| Val | 64.3 | 57.2 | 54.8 | 65.9 | 60.6 | 5.4 | 71.6 | 71.3 | 70.1 | 71.0 | 0.8 |
| Met | 21.7 | 20.6 | 20.7 | 20.4 | 20.8 | 0.6 | 21.4 | 21.4 | 21.7 | 21.5 | 0.2 |
| lie | 51.8 | 47.7 | 47.4 | 41.7 | 47.2 | 4.2 | 49.6 | 50.1 | 42.3 | 47.3 | 4.3 |

TABLE 2-continued

Analyses of Collagen Content in Liver Biomatrix Scaffold

| | BIOMATRIX SCAFFOLDS (N = 4) | | | | | | LIVER TISSUE (N = 3) | | | | |
|---|---|---|---|---|---|---|---|---|---|---|---|
| Amino acids | Sample 1 Res/1000 | Sample 2 Res/1000 | Sample 3 Res/1000 | Sample 4 Res/1000 | AVER- AGE Res/1000 | SD Res/1000 | Sample 1 Res/1000 | Sample 2 Res/1000 | Sample 3 Res/1000 | AVER- AGE Res/1000 | SD Res/1000 |
| Leu | 92.7 | 83.8 | 109.7 | 87.5 | 93.4 | 11.5 | 93.8 | 95.1 | 92.7 | 93.9 | 1.2 |
| Tyr | 30.8 | 26.9 | 22.4 | 28.1 | 27.0 | 3.5 | 31.8 | 32.1 | 27.5 | 30.5 | 2.6 |
| Phe | 45.5 | 40.7 | 42.4 | 42.8 | 42.8 | 2.0 | 47.8 | 51.0 | 43.7 | 47.5 | 3.7 |
| His | 21.0 | 18.8 | 13.2 | 21.8 | 18.7 | 3.9 | 21.8 | 21.5 | 24.1 | 22.5 | 1.4 |
| Hyl | 1.0 | 1.8 | 1.6 | 4.3 | 2.2 | 1.5 | 0.0** | 0.0** | 0.0** | 0.0** | 0.0** |
| Lys | 40.6 | 70.0 | 49.8 | 66.2 | 56.7 | 13.8 | 74.6 | 78.5 | 73.0 | 75.3 | 2.8 |
| Arg | 57.5 | 57.6 | 48.7 | 46.1 | 52.5 | 6.0 | 47.0 | 46.0 | 42.1 | 45.0 | 2.6 |

Note:
*less than 0.2 res/1,000;
**not detected.

TABLE 3

Analyses of Growth Factors Bound to Bile Duct Biomatrix Scaffolds

| NAME | CYTOKINE FULL NAME | Human Bile Ducts | Human Bile Duct Biomatrix Scaffolds | % |
|---|---|---|---|---|
| bFGF | Basic fibroblast growth factor | 58299 | 126 | 0% |
| b-NGF | Nerve growth factor (beta polypeptide) | 516 | 81 | 16% |
| EGF | Epidermal growth factor | 91 | 108 | 119% |
| EGF R | Epidermal growth factor receptor | 479 | 145 | 30% |
| FGF-4 | Fibroblast growth factor-4 | 31 | 36 | 116% |
| FGF-6 | Fibroblast growth factor-6 | 14 | 17 | 121% |
| FGF-7 | Fibroblast growth factor-? | 149 | 23 | 15% |
| GCSF | Granulocyte-colony stimulating Factor | 207 | 233 | 113% |
| GDNF | Glial-derived neurotrophic factor | 53 | 49 | 92% |
| GM-CSF | Granulocyte macrophage-colony stimulating factor | 108 | 97 | 90% |
| HB-EGF | Heparin-binding epidermal growth factor | 28 | 23 | 82% |
| IGFBP-1 | Insulin-like growth factor binding proteins 1 | 431 | 61 | 14% |
| IGFBP-2 | Insulin-like growth factor binding proteins 2 | 255 | 20 | 8% |
| IGFBP-3 | Insulin-like growth factor binding proteins 3 | 77 | 54 | 70% |
| IGFBP-4 | Insulin-like growth factor binding proteins 4 | 81 | 58 | 72% |
| IGFBP-6 | Insulin-like growth factor binding proteins 6 | 783 | 107 | 14% |
| JGF-1 | Insulin-like growth factor-I | 18 | 6 | 33% |
| IGF-1 SR | Insulin-like growth factor-I | 89 | 25 | 28% |
| IGF-11 | Insulin-like growth factor-2 | 2873 | 3945 | 137% |
| M-CSF | Macrophage-colony stimulating factor | 149 | 105 | 70% |
| M-CSF R | Macrophage colony stimulating factor receptor | 358 | 71 | 20% |
| NT-3 | Neurotrophin-3 | 71 | 71 | 100% |
| NT-4 | Neurotrophin-4 | 75 | 58 | 77% |
| PDGF R a | Platelet-derived growth factor receptor alpha | 104 | 63 | 61% |
| PDGF R b | Platelet-derived growth factor receptor beta | 489 | 110 | 22% |
| PDGF-AA | Platelet-derived growth factor AA | 114 | 52 | 46% |
| PDGF-AB | Platelet-derived growth factor AB | 87 | 65 | 75% |
| PDGF-BB | Platelet-derived growth factor BB | 155 | 75 | 48% |
| PIGF | Phosphatidylinositol glycan anchor biosynthesis, class F | 146 | 14 | 10% |
| SCF | Stromal cell-derived factor-1 | 39 | 22 | 56% |
| SCF R | Stramal cell-derived factor receptor | 159 | 31 | 19% |
| TGF-a | Transforming growth factor alpha | 52 | 25 | 48% |
| TGF-b | Transforming growth factor-beta | 234 | 277 | 118% |
| TGF-b 2 | transforming growth factor-beta 2 | 103 | 121 | 117% |
| TGF-b 3 | Transforming growth factor-beta 3 | 28 | 16 | 57% |
| VEGF | Vascular endothelial growth factor | 74 | 35 | 47% |

TABLE 3-continued

Analyses of Growth Factors Bound to Bile Duct Biomatrix Scaffolds

| NAME | CYTOKINE FULL NAME | Human Bile Ducts | Human Bile Duct Biomatrix Scaffolds | % |
|---|---|---|---|---|
| VEGF R2 | Vascular endothelial growth factor receptor 2 | 108 | 33 | 31% |
| VEGF R3 | Vascular endothelial growth factor receptor 3 | 45 | 40 | 89% |

TABLE 4

Antibodies Utilized

| Antibody's name | Host and isotype | Company | Catalog NO. | Dilution |
|---|---|---|---|---|
| *Primary Antibodies to extracellular matrix components* | | | | |
| 1. collagen 1 | mouse lgG1 | Sigma | C2456 | 1/2000 |
| 2. collagen 3A1 | Mouse lgG1 | Sigma | C7805 | 1/2000 |
| 3. collagen 4A1 | Goat lgG | Santa Cruz | sc-9302 | 1/50 |
| 4. collagen 5A1 | Rabbit lgG | Santa Cruz | sc-20648 | 1/50 |
| 5. collagen 6 | Rabbit lgG | Santa Cruz | Sc-20649 | 1/50 |
| 6. chondroitin sulfate | mouse lgM | Sigma | C8035 | 1/200 |
| 7. Elastin | Rabbit lgG | Abeam | ab21610 | 1/200 |
| 8. entactin (nidogen 1) | Rat lgG | GeneTex | GTX72367 | 1/200 |
| 9. heparan sulfate | Mouse lgM | Seiko, Japan | 270426 | 1/200 |
| 10. HS-PG: perlecan | Mouse lgG2a | NeoMarkers | RT-794 | 1/200 |
| 11. HS-PG: syndecan-1 | Goat lgG | R&D | AF2780 | 1/100 |
| 12. Fibronectin | Mouse lgG1 | Sigma | F7387 | 1/200 |
| 13. Laminin | Mouse lgG1 | Sigma | L8271 | 1/1000 |
| *Primary Antibodies to other proteins* | | | | |
| 1. AFP | Rabbit lgG | Novus Biologicals | NB100-1611 | 1/200 |
| 2. Albumin | Rabbit lgG | Novus Biologicals | NB 600-570 | 1/200 |
| 3. ASMA | mouse lgG2a | Sigma | A2547 | 1/300 |
| 4. Ck18 | mouse lgG2b | Sigma | SAB3300016 | 1/400 |
| 5. hCK19 | mouse lgG2a | Abeam | ab7754 | 1/250 |
| 6. CK19 | Rabbit lgG | Abeam | Ab52625 | 1/200 |
| 7. CYP3A4 | Mouse lgG | Abnova | H00001576-B01P | 1/200 |
| 8. Desmin | Rabbit lgG | Abeam | Ab8592 | 1/200 |
| 9. EpCAM | Mouse lgG1 | NeoMarkers | MS-181 | 1/200 |
| 10. secretin receptor | Rabbit lgG | Santa Cruz | sc.:.26633 | 1/100 |
| 11. PAN CK | Mouse lgG1 | Abeam | ab-7753 | 1/300 |
| 12. Tubulin-a | Mouse lgG1 | Neomarkers | MS-581 | 1/1000 |
| 13. Vimentin | Mouse lgG1 | Abeam | Ab8978 | 1/200 |
| *Secondary Antibodies or dyes for florescent cell stain or tissue immunohistochemistry* | | | | |
| 1. Alexa Fluor ® 488/594 goat anti-mouse IgG 1 or 2a or anti rabbit IgG | | Molecular Probes | | 1/500 |
| 2. VECTASTAIN ® ABC system | | Vector Laboratories | | |
| 3. NovaRED ™ SUBSTRATE KIT | | Vector Laboratories | | |
| 4. Phalloidin 488 | | Molecular Probes | | 1/500 |

TABLE 5

Primers Utilized for RT-PCR

| No | Name | Full name | GenBank Accession | Sequence (5'-> 3') | Tm | Amplicon Size |
|---|---|---|---|---|---|---|
| 1 | CXCR-4 | chemokine (C-X-C motif) receptor 4 | AJ224869 | TACACCGAGGAAATGGGCTCA | 63 | 112 |
| | | | | AGATGATGGAGTAGATGGTGGG | 60.4 | |
| 2 | EpCAM | epithelial cell adhesion molecule | NM 002354 | ATAACCTGCTCTGAGCGAGTG | 61.6 | 104 |
| | | | | TGAAGTGCAGTCCGCAAACT | 62.3 | |
| 3 | KRT19 | keratin 19 | NM 002276 | ACCAAGTTTGAGACGGAACAG | 60.2 | 181 |
| | | | | CCCTCAGCGTACTGATTTCCT | 61.3 | |
| 4 | HNF6 | hepatocyte nuclear factor 6, alpha | NM 004498 | ATGTGGAAGTGGCTGCAGGA | 60.7 | 105 |
| | | | | TGTGTTGCCTCTATCCTTCCC | 61.2 | |
| 5 | FOXA2 | forkhead box A2 | NM 021784 | GCGACCCCAAGACCTACAG | 61.7 | 162 |
| | | | | GGTTCTGCCGGTAGAAGGG | 61.7 | |

TABLE 5-continued

Primers Utilized for RT-PCR

| No | Name | Full name | GenBank Accession | Sequence (5'-> 3') | Tm | Amplicon Size |
|---|---|---|---|---|---|---|
| 6 | PROX1 | prospero homeobox 1 | NM 002763 | TTGACATTGGAGTGAAAAGG ACG | 61 | 100 |
|  |  |  |  | TGCTCAGAACCTTGGGGATTC | 61.8 |  |
| 7 | AFP | alpha-fetoprotein | NM 001134 | CTTGCACACAAAAAGCCCAC T | 61.9 | 138 |
|  |  |  |  | GGGATGCCTTCTTGCTATCTC AT | 61.8 |  |
| 8 | ALB | albumin | M12523 | TTTATGCCCCGGAACTCCTTT | 61.4 | 90 |
|  |  |  |  | ACAGGCAGGCAGCTTTATCA G | 62.4 |  |
| 9 | TF | transferrin | NM 001063 | CCTCCTACCTTGATTGCATCA G | 60.2 | 137 |
|  |  |  |  | TTTTGACCCATAGAACTCTGC C | 60 |  |
| 10 | CYP3A4 | cytochrome P450, family 3, subfamily A, polypeptide 4 | NM 017460 | AAGTCGCCTCGAAGATACAC A | 60.9 | 174 |
|  |  |  |  | AAGGAGAGAACAC TGCTCGTG | 61.7 |  |
| 11 | TAT | tyrosine aminotransferase | NM 000353 | TTTGGGACCCTGTACCATTGT | 61 | 102 |
|  |  |  |  | GCATTGGACTTGAGGAAGCT C | 61 |  |
| 12 | G6PC | glucose-6-phosphatase, catalytic subunit | NM 000151 | TCAGGGAAAGATAAAGCCGA CC | 61.8 | 105 |
|  |  |  |  | AGGTAGATTCGTGACAGACA GAC | 61.1 |  |
| 13 | CFTR | cystic fibrosis transmembrane conductance regulator | NM 000492 | AAAAGGCCAGCGTTGT CTCC | 63 | 170 |
|  |  |  |  | TGAAGCCAGCTCTCTATCCCA | 62.1 |  |
| 14 | GGT1 | gamma-glutamyl-transferase 1 | J05235 | GGGGAGATCGAGGGCTATGA G | 63 | 150 |
|  |  |  |  | GATGACGGTCCGCTTGTTTTC | 61.8 |  |
| 15 | AE2 | SLC4A2 | NM 003040 | GCCAAGGGCGCAGATTCTT | 63 | 103 |
|  |  |  |  | CCAGGGTGCGGTGAAGTTC | 62.9 |  |
| 16 | ASST | SLC10A2 | NM 000452 | TGTGTTGGCTTCCTCTGTCAG | 62 | 115 |

TABLE 6

Analyses of Growth Factor Bound to Liver Biomatrix Scaffolds

| Name | Cytokine Full Name | Rat Livers | Rat Biometrix Scaffolds | Percent |
|---|---|---|---|---|
| bFGF | Basic fibroblast growth factor | 100.06 | 394.14 | 394 |
| EGF | Epidermal grov.rth factor | 74.81 | 76.02 | 102 |
| EGF R | Epidermal gro'Nth factor receptor | 92.81 | 81.64 | 88 |
| ffiF-4 | Fibroblast growth factor-4 | 15.06 | 1321 | 88 |
| ffiF-6 | Flbroblast gro11.rth factor-6 | 4.81 | 3.77 | 78 |
| FGF-7 | Fi broblast gro'Nth factor-7 | 10.06 | 6.32 | 63 |
| GCSF | Granulocyte-colony stimulating factor | 348.06 | 338.20 | 97 |
| GDNF | Glial-derivecl neurotrophic factor | 81.31 | 43.59 | 54 |
| GM-CSF | Granulocyte macrophage-colorrf stimulating factor | 133.56 | 105.38 | 79 |
| HB-EGF | Heparin-binding epidermal growth factor | 44.56 | 38.23 | 86 |
| lGFBP-1 | lnsulin·Hke growth factor binding proteins 1 | 67.81 | 70.40 | 104 |
| fGFBP-3 | lnsultn-like grOwth factor binding proteins 3 | 140.81 | 201.90 | 143 |
| IGFBP-4 | lnsulin-like growth factor binding proteins 4 | 83.56 | 58.92 | 71 |
| IGFBP-6 | Insulin-I ike growth factor binding proteins 6 | 91.81 | 72.19 | 79 |
| !GF-! | Insulin-like growth factor-I | 1.56 | 1.98 | 127 |
| !GF-1 SR | Insulin-like growth factor-I | 7.31 | 3.51 | 48 |

TABLE 6-continued

Analyses of Growth Factor Bound to Liver Biomatrix Scaffolds

| Name | Cytokine Full Name | Rat Livers | Rat Biometrix Scaffolds | Percent |
|---|---|---|---|---|
| IGF-U | Insulin-like growth factor-2 | 3749.06 | 3482.52 | 93 |
| M-CSF | Macrophage-colony stimulating factor | 170.31 | 134.68 | 79 |
| M-CSF R | Macrophage colony stimulating factor receptor | 70.56 | 50.47 | 72 |
| NT.J | Neurotmphin-3 | 25.56 | 5.03 | 20 |
| NT-4 | Neurotrophin-4 | 55.06 | 43.59 | 79 |
| PDGF R a | Platelet-derived growth factor receptor alpha | 10.56 | 21.11 | 200 |
| PDGF R b | Platelet-derived growth factor receptor beta | 113.81 | 85.46 | 75 |
| PDGF-AA | Platelet-derived growth factor AA | 62.06 | 106.40 | 171 |
| PDGF-AB | Platelet-derived gro11.rth factor AB | 19.31 | 19.34 | 100 |
| PDGF-BB | Platelet-derived1owth factor BB | 9.56 | 1423 | 149 |
| PIGF | Phosphatidyl1nositol glycan anchor biosynthesis, class F | 4.81 | 8.36 | 174 |
| SCF | Stromal cell-derived factor-1 | 2.06 | 42.56 | 2064 |
| SCF R | Stromal cell-derived factor receptor | 17.06 | 17.80 | 104 |
| TGF-a | Transforming growth factor alpha | 21.31 | 21.63 | 102 |
| TGF-b | Transforming growth fuctor-beta | 330.31 | 342.77 | 104 |
| TGF-b 2 | transforming growth factor-beta 2 | 134.06 | 152.34 | 114 |
| TGF-b 3 | Transforming growth factor-beta 3 | 1.06 | 0.18 | 17 |
| VEGF | Vascular endothelial growth factor | 70.56 | 94.14 | 133 |
| VEGF R2 | Vascular endothelial growth factor receptor 2 | 13.56 | 11.93 | 88 |
| VEGF R3 | Vascular endothelial growth factor receptor 3 | 459.56 | 46.91 | 10 |

TABLE 7

Properties of human hepatic stem cells (hHpSCs) after isolation and in culture

| Properties | hHpSCs-freshly Isolated | Self-Replication Conditions illay 12) KM and TCP or Type ID collagen | Differentiation Conditions (Day 12) DM and Type I Collagen | DM and Biometrix Scaffolds |
|---|---|---|---|---|
| How long to attach | — | 4-5 hours on TCP; -3 hours on type III collagen | 7-12 hours | 3 hours |
| % attachment of viable cells | — | 60-80% on TCP and -100% on type III collagen | 100% | |
| Morphology of colonies | | 2-dimensional (monolayer) colonies | Cords of cells; somewhat cuboidal | Cords of cells; very 3-dimensional |
| Doubling time (division rate) | — | A division every 36 hrs on TCP and 24-26 hours on type III collagen | A division every 40-SO hours transitioning to growth arrest by 7-10 days | Only a few divisions transitioning to growth arrest by s days |
| Duration of Viability | | >6 months (remaining as stem cells) | -2 weeks | >8 weeks as differentiated cells (not tested yet for longer) |
| Percentage of Cells Expressing the Specified Marker | | | | |
| EpCAM | | 100% | Present on membranes of small cholangiocytes; no expression at all in mature hepatocytes | |
| NCAM | | >80% | None | |
| CD133/1 | | 90% | None | |
| SOX 17 | | 100% | None | |
| CK 8/18, E-cadherin | | 100% | 100% | |
| CK19 | | 90% | Present in cholangiocytes but not in hepatocytes | |
| a-fetoprotein | | None; Ifany, then due to contamination with hepatoblasts | Moderate expression in most cells at 10-12 days | Expression in first 2-3 days, decreases dramatically thereafter, no expression from day 7 on. |
| P450s | | None or negligible levels | 100% (-18,000 RLU)* | 100% (35,000 RLU)* |

TABLE 7-continued

Properties of human hepatic stem cells (hHpSCs) after isolation and in culture

| Properties | hHpSCs-freshly Isolated | Self-Replication Conditions illay 12) KM and TCP or Type ID collagen | Differentiation Conditions (Day 12) | |
|---|---|---|---|---|
| | | | DM and Type I Collagen | DM and Biomatrix Scaffolds |
| Urea synthesized | | None | 2.S mgs/dL | 7 mgs/dL |
| Markers: mature hepatocytes | | Most of the cells have none; those expressing do so weakly (e.g. albumin); all express transferrin mRNA but no transferrin protein | albumin, transferrin protein, tyrosine aminotransferase (TAT), glycogen. Weak levels on collagen I versus strong on biomatrix scaffolds | |
| Markers: mature cholangiocytes | | Most none; those expressing any do so weakly: (e.g. CFTR, GGTI, AE2: no expression of ASBT and late aquaporins | Secretin receptor, AE2, ABAT, CFTR, GGTl, AE2, ASBT, but with weak levels on collagen I versus very strong on biomatrix scaffolds | |

KM = Kubota's Medium, a serum-free medium used for hHpSCs and progenitors;
HDM-L = differentiation medium derived from KM and with hormones and factors given in the methods.
TCP = tissue culture plastic.
*See FIG. SF;
**See FIG. SE

TABLE 8

Biomatrix plating volumes for multiwall plates

| Plate Size | Volume/well | Volume/Plate | Plates/Bottle |
|---|---|---|---|
| 384-well | 30 ul | 12.0 ml | 10 |
| 96-well | 50 ul | 5.0 ml | 24 |
| 24-well | 300 ul | 7.5 ml | 16 |
| 12-well | 800 ul | 10 ml | 12 |
| 6-well | 1.5 ml | 9 ml | 13 |

That which is claimed is:

1. A method of producing a plurality of biomatrix particles from a biological tissue for dispersal onto culture apparatus, comprising:
   (a) perfusing or homogenizing the biological tissue with a buffer comprising a salt concentration from about 3.5 M NaCl to about 4.5 M NaCl;
   (b) perfusing the biological tissue or extracting the homogenate of step (a) with a delipidating buffer comprising lipases and detergents in a serum free first medium, having a neutral pH and an osmolality from about 250 mOsm/kg to about 350 mOsm/kg, wherein the detergents do not comprise sodium dodecyl sulfate or TritonX-100;
   (c) perfusing the biological tissue or extracting the homogenate of step (b) with a buffer at a neutral pH and comprising a salt concentration ranging from about 2.0 M NaCl to about 5.0 M NaCl, the concentration chosen to not lose insoluble collagens identified in the biological tissue;
   (d) perfusing the biological tissue or extracting the homogenate of step (c) with RNase and DNase in a buffer;
   (e) rinsing the biological tissue or homogenate of step (d) with a second medium having a neutral pH, is serum-free and having an osmolality ranging from about 250 mOsm/kg to about 350 mOsm/kg, thereby producing an intact or homogenized biomatrix scaffold from the biological tissue;
   (f) pulverizing the intact or homogenized biomatrix scaffold into a plurality of biomatrix particles ranging in size from about 1 nm to about 100 µm.

2. The method of claim 1, wherein the intact or homogenized biomatrix scaffold comprises at least 95% of the collagens and most collagen-associated matrix components, matrix bound growth factors, hormones, and cytokines of the biological tissue.

3. The method of claim 1, wherein the biological tissue is selected from the group consisting of liver, lung, thyroid, skin, pancreas, blood vessels, bladder, kidneys, brain, biliary tree, duodenum, abdominal aorta, iliac vein, heart and intestines.

4. The method of claim 1, wherein the pulverizing of step (f) comprises cryogenic grinding.

5. The method of claim 1, wherein the detergents are selected from the group consisting of salts of deoxycholic acid, 1-heptanesulfonic acid, N-laurylsarcosine, lauryl sulfate, 1-octane sulfonic acid and taurocholic acid; benzalkonium chloride; cetylpyridinium; methylbenzethonium chloride; decamethonium bromide; alkyl betaines; alkyl amidoalkyl betaines; N-dodecyl-N,N-dimethyl-3-ammonio-1-propanesulfonate; phosphatidylcholine; n-decyl α-D-glucopyranoside; n-decyl β-D-maltopyranoside; n-dodecyl β-D-maltoside; n-octyl β-D-glucopyranoside; sorbitan esters; n-tetradecyl β-D-maltoside; tritons; Nonidet-P-40; Poloxamer 188; sodium lauryl sulfate; and sodium deoxycholate.

6. The method of claim 1, wherein the lipases are phospholipases.

7. The method of claim 1, wherein the serum free first medium is a basal medium selected from the group consisting of RPMI 1640, DME/F12, DME, F12, Waymouth's, and William's medium.

8. The method of claim 1, wherein the second medium comprises at least one of the constituents present in interstitial fluid.

9. The method of claim 1, wherein the delipidating buffer of step (b) comprises from about 20 units/L to about 50 units/L phospholipase A2 and about 1% sodium deoxycholate in the first medium.

10. The method of claim 1, wherein the salt concentration of the buffer of step (c) is from about 3.4 M NaCl to about 3.5 M NaCl when used for scaffold preparation from an adult liver and is from about 4.0 M NaCl to about 4.5 M NaCl when used for scaffold preparation from a fetal liver.

11. The method of claim 1, wherein the buffer of step (c) further comprises a protease inhibitor.

12. The method of claim 11, wherein the protease inhibitor is soybean trypsin inhibitor.

13. The method of claim 1, wherein the buffer of step (d) further comprises a protease inhibitor.

14. The method of claim 13, wherein the protease inhibitor is soybean trypsin inhibitor.

15. The method of claim 1, wherein all media and buffers of steps (a) through (e) are free of a detectable amount of an enzyme that degrades extracellular matrix components.

16. The method of claim 1, wherein the biological tissue is from a mammal.

* * * * *

SEQUENCE LISTING

```
<160> NUMBER OF SEQ ID NOS: 34

<210> SEQ ID NO 1
<211> LENGTH: 21
<212> TYPE: DNA
<213> ORGANISM: Artificial
<220> FEATURE:
<223> OTHER INFORMATION: RT-PCR primer

<400> SEQUENCE: 1
tacaccgagg aaatgggctc a                                            21

<210> SEQ ID NO 2
<211> LENGTH: 22
<212> TYPE: DNA
<213> ORGANISM: Artificial
<220> FEATURE:
<223> OTHER INFORMATION: RT-PCR primer

<400> SEQUENCE: 2
agatgatgga gtagatggtg gg                                           22

<210> SEQ ID NO 3
<211> LENGTH: 21
<212> TYPE: DNA
<213> ORGANISM: Artificial
<220> FEATURE:
<223> OTHER INFORMATION: RT-PCR primer

<400> SEQUENCE: 3
ataacctgct ctgagcgagt g                                            21
```

```
<210> SEQ ID NO 4
<211> LENGTH: 20
<212> TYPE: DNA
<213> ORGANISM: Artificial
<220> FEATURE:
<223> OTHER INFORMATION: RT-PCR primer

<400> SEQUENCE: 4
tgaagtgcag tccgcaaact                                                    20

<210> SEQ ID NO 5
<211> LENGTH: 21
<212> TYPE: DNA
<213> ORGANISM: Artificial
<220> FEATURE:
<223> OTHER INFORMATION: RT-PCR primer

<400> SEQUENCE: 5
accaagtttg agacggaaca g                                                  21

<210> SEQ ID NO 6
<211> LENGTH: 21
<212> TYPE: DNA
<213> ORGANISM: Artificial
<220> FEATURE:
<223> OTHER INFORMATION: RT-PCR primer

<400> SEQUENCE: 6
ccctcagcgt actgatttcc t                                                  21

<210> SEQ ID NO 7
<211> LENGTH: 20
<212> TYPE: DNA
<213> ORGANISM: Artificial
<220> FEATURE:
<223> OTHER INFORMATION: RT-PCR primer

<400> SEQUENCE: 7
atgtggaagt ggctgcagga                                                    20

<210> SEQ ID NO 8
<211> LENGTH: 21
<212> TYPE: DNA
<213> ORGANISM: Artificial
<220> FEATURE:
<223> OTHER INFORMATION: RT-PCR primer

<400> SEQUENCE: 8
tgtgttgcct ctatccttcc c                                                  21

<210> SEQ ID NO 9
<211> LENGTH: 19
<212> TYPE: DNA
<213> ORGANISM: Artificial
<220> FEATURE:
<223> OTHER INFORMATION: RT-PCR primer

<400> SEQUENCE: 9
gcgaccccaa gacctacag                                                     19

<210> SEQ ID NO 10
<211> LENGTH: 19
<212> TYPE: DNA
<213> ORGANISM: Artificial
<220> FEATURE:
<223> OTHER INFORMATION: RT-PCR primer
```

-continued

```
<400> SEQUENCE: 10
ggttctgccg gtagaaggg                                                  19

<210> SEQ ID NO 11
<211> LENGTH: 23
<212> TYPE: DNA
<213> ORGANISM: Artificial
<220> FEATURE:
<223> OTHER INFORMATION: RT-PCR primer

<400> SEQUENCE: 11
ttgacattgg agtgaaaagg acg                                             23

<210> SEQ ID NO 12
<211> LENGTH: 21
<212> TYPE: DNA
<213> ORGANISM: Artificial
<220> FEATURE:
<223> OTHER INFORMATION: RT-PCR primer

<400> SEQUENCE: 12
tgctcagaac cttggggatt c                                               21

<210> SEQ ID NO 13
<211> LENGTH: 21
<212> TYPE: DNA
<213> ORGANISM: Artificial
<220> FEATURE:
<223> OTHER INFORMATION: RT-PCR primer

<400> SEQUENCE: 13
cttgcacaca aaagcccac t                                                21

<210> SEQ ID NO 14
<211> LENGTH: 23
<212> TYPE: DNA
<213> ORGANISM: Artificial
<220> FEATURE:
<223> OTHER INFORMATION: RT-PCR primer

<400> SEQUENCE: 14
gggatgcctt cttgctatct cat                                             23

<210> SEQ ID NO 15
<211> LENGTH: 21
<212> TYPE: DNA
<213> ORGANISM: Artificial
<220> FEATURE:
<223> OTHER INFORMATION: RT-PCR primer

<400> SEQUENCE: 15
tttatgcccc ggaactcctt t                                               21

<210> SEQ ID NO 16
<211> LENGTH: 21
<212> TYPE: DNA
<213> ORGANISM: Artificial
<220> FEATURE:
<223> OTHER INFORMATION: RT-PCR primer

<400> SEQUENCE: 16
acaggcaggc agctttatca g                                               21

<210> SEQ ID NO 17
<211> LENGTH: 22
```

```
<212> TYPE: DNA
<213> ORGANISM: Artificial
<220> FEATURE:
<223> OTHER INFORMATION: RT-PCR primer

<400> SEQUENCE: 17
cctcctacct tgattgcatc ag                                              22

<210> SEQ ID NO 18
<211> LENGTH: 22
<212> TYPE: DNA
<213> ORGANISM: Artificial
<220> FEATURE:
<223> OTHER INFORMATION: RT-PCR primer

<400> SEQUENCE: 18
ttttgaccca tagaactctg cc                                              22

<210> SEQ ID NO 19
<211> LENGTH: 21
<212> TYPE: DNA
<213> ORGANISM: Artificial
<220> FEATURE:
<223> OTHER INFORMATION: RT-PCR primer

<400> SEQUENCE: 19
aagtcgcctc gaagatacac a                                               21

<210> SEQ ID NO 20
<211> LENGTH: 21
<212> TYPE: DNA
<213> ORGANISM: Artificial
<220> FEATURE:
<223> OTHER INFORMATION: RT-PCR primer

<400> SEQUENCE: 20
aaggagagaa cactgctcgt g                                               21

<210> SEQ ID NO 21
<211> LENGTH: 21
<212> TYPE: DNA
<213> ORGANISM: Artificial
<220> FEATURE:
<223> OTHER INFORMATION: RT-PCR primer

<400> SEQUENCE: 21
tttgggaccc tgtaccattg t                                               21

<210> SEQ ID NO 22
<211> LENGTH: 21
<212> TYPE: DNA
<213> ORGANISM: Artificial
<220> FEATURE:
<223> OTHER INFORMATION: RT-PCR primer

<400> SEQUENCE: 22
gcattggact tgaggaagct c                                               21

<210> SEQ ID NO 23
<211> LENGTH: 22
<212> TYPE: DNA
<213> ORGANISM: Artificial
<220> FEATURE:
<223> OTHER INFORMATION: RT-PCR primer

<400> SEQUENCE: 23
```
tcagggaaag ataaagccga cc                                            22

<210> SEQ ID NO 24
<211> LENGTH: 23
<212> TYPE: DNA
<213> ORGANISM: Artificial
<220> FEATURE:
<223> OTHER INFORMATION: RT-PCR primer

<400> SEQUENCE: 24
aggtagattc gtgacagaca gac                                           23

<210> SEQ ID NO 25
<211> LENGTH: 20
<212> TYPE: DNA
<213> ORGANISM: Artificial
<220> FEATURE:
<223> OTHER INFORMATION: RT-PCR primer

<400> SEQUENCE: 25
aaaaggccag cgttgtctcc                                               20

<210> SEQ ID NO 26
<211> LENGTH: 21
<212> TYPE: DNA
<213> ORGANISM: Artificial
<220> FEATURE:
<223> OTHER INFORMATION: RT-PCR primer

<400> SEQUENCE: 26
tgaagccagc tctctatccc a                                             21

<210> SEQ ID NO 27
<211> LENGTH: 21
<212> TYPE: DNA
<213> ORGANISM: Artificial
<220> FEATURE:
<223> OTHER INFORMATION: RT-PCR primer

<400> SEQUENCE: 27
ggggagatcg agggctatga g                                             21

<210> SEQ ID NO 28
<211> LENGTH: 21
<212> TYPE: DNA
<213> ORGANISM: Artificial
<220> FEATURE:
<223> OTHER INFORMATION: RT-PCR primer

<400> SEQUENCE: 28
gatgacggtc cgcttgtttt c                                             21

<210> SEQ ID NO 29
<211> LENGTH: 19
<212> TYPE: DNA
<213> ORGANISM: Artificial
<220> FEATURE:
<223> OTHER INFORMATION: RT-PCR primer

<400> SEQUENCE: 29
gccaagggcg cagattctt                                                19

<210> SEQ ID NO 30
<211> LENGTH: 19
<212> TYPE: DNA
<213> ORGANISM: Artificial

```
<220> FEATURE:
<223> OTHER INFORMATION: RT-PCR primer

<400> SEQUENCE: 30
ccagggtgcg gtgaagttc                                                   19

<210> SEQ ID NO 31
<211> LENGTH: 21
<212> TYPE: DNA
<213> ORGANISM: Artificial
<220> FEATURE:
<223> OTHER INFORMATION: RT-PCR primer

<400> SEQUENCE: 31
tgtgttggct tcctctgtca g                                                21

<210> SEQ ID NO 32
<211> LENGTH: 22
<212> TYPE: DNA
<213> ORGANISM: Artificial
<220> FEATURE:
<223> OTHER INFORMATION: RT-PCR primer

<400> SEQUENCE: 32
ggcagcatcc tataatgagc ac                                               22

<210> SEQ ID NO 33
<211> LENGTH: 23
<212> TYPE: DNA
<213> ORGANISM: Artificial
<220> FEATURE:
<223> OTHER INFORMATION: RT-PCR primer

<400> SEQUENCE: 33
catgagaagt atgacaacag cct                                              23

<210> SEQ ID NO 34
<211> LENGTH: 22
<212> TYPE: DNA
<213> ORGANISM: Artificial
<220> FEATURE:
<223> OTHER INFORMATION: RT-PCR primer

<400> SEQUENCE: 34
agtccttcca cgataccaaa gt                                               22
```

UNITED STATES PATENT AND TRADEMARK OFFICE
CERTIFICATE OF CORRECTION

PATENT NO. : 10,640,747 B2
APPLICATION NO. : 15/952094
DATED : May 5, 2020
INVENTOR(S) : Marsha Lynn Roach et al.

Page 1 of 1

It is certified that error appears in the above-identified patent and that said Letters Patent is hereby corrected as shown below:

In the Specification

In Column 1, replace Lines 20-27 with the following paragraph:
-- This invention was made with government support under Grant Numbers DK065933, DE019569, DK034987, AA014243 and CA016086 awarded by the National Institutes of Health. The government has certain rights in the invention. --

Signed and Sealed this
Seventh Day of July, 2020

Andrei Iancu
*Director of the United States Patent and Trademark Office*